(12) United States Patent
Fujita et al.

(10) Patent No.: US 10,136,850 B2
(45) Date of Patent: Nov. 27, 2018

(54) BIOLOGICAL STATE ESTIMATION DEVICE, BIOLOGICAL STATE ESTIMATION SYSTEM, AND COMPUTER PROGRAM

(75) Inventors: Etsunori Fujita, Hiroshima (JP); Yumi Ogura, Hiroshima (JP); Shinichiro Maeda, Hiroshima (JP); Naoki Ochiai, Hiroshima (JP)

(73) Assignee: Delta Tooling Co., Ltd., Hiroshima-shi (JP)

( * ) Notice: Subject to any disclaimer, the term of this patent is extended or adjusted under 35 U.S.C. 154(b) by 1757 days.

(21) Appl. No.: 13/501,903

(22) PCT Filed: Oct. 14, 2010

(86) PCT No.: PCT/JP2010/068068
§ 371 (c)(1),
(2), (4) Date: Jun. 26, 2012

(87) PCT Pub. No.: WO2011/046178
PCT Pub. Date: Apr. 21, 2011

(65) Prior Publication Data
US 2012/0259181 A1 Oct. 11, 2012

(30) Foreign Application Priority Data
Oct. 14, 2009 (JP) .................................. 2009-237802

(51) Int. Cl.
*A61B 5/18* (2006.01)
*A61B 5/00* (2006.01)
*B60W 40/08* (2012.01)

(52) U.S. Cl.
CPC .............. *A61B 5/18* (2013.01); *A61B 5/4035* (2013.01); *A61B 5/4809* (2013.01);
(Continued)

(58) Field of Classification Search
CPC ....... A61B 5/02; A61B 5/024; A61B 5/02405; A61B 5/0255; A61B 5/18; A61B 5/4806;
(Continued)

(56) References Cited

U.S. PATENT DOCUMENTS 3,187,275 A * 6/1965 Stanley ........................ 333/17.1
5,853,005 A * 12/1998 Scanlon ........................ 600/459
(Continued)

FOREIGN PATENT DOCUMENTS

EP        2092889 A1 *   8/2009   ............... A61B 5/18
JP     2004 344612      12/2004
(Continued)

OTHER PUBLICATIONS

Extended European Search Report dated Oct. 22, 2014 in Patent Application No. 10823446.9.
(Continued)

*Primary Examiner* — Niketa Patel
*Assistant Examiner* — Nathan A Baldwin
(74) *Attorney, Agent, or Firm* — Oblon, McClelland, Maier & Neustadt, L.L.P.

(57) ABSTRACT

A biological body state estimation device configured such that a homeostatic function level is sorted and acquired in plural stages by using a biological signal obtained from an upper body of a person and each stage of the homeostatic function level is plotted in time series in accordance with a time axis indicated on the lateral axis and displayed as a graph by a display. A highest part on the vertical axis of the graph can be displayed as a highly active state and a lowest part as a function decline state. Therefore, a state of fluctuation due to autonomous nerves as an attempt to maintain homeostasis, progress of a feeling of fatigue, and a state
(Continued)

stimulated by activation of the brain can be captured as a periodic function. Moreover, a sleep prediction phenomenon can be captured.

12 Claims, 35 Drawing Sheets

(52) U.S. Cl.
CPC .......... *A61B 5/7239* (2013.01); *A61B 5/6893* (2013.01); *A61B 5/7242* (2013.01); *A61B 5/742* (2013.01); *A61B 5/744* (2013.01); *B60W 2040/0872* (2013.01)

(58) Field of Classification Search
CPC .... A61B 5/4809; A61B 5/4812; A61B 5/4818
See application file for complete search history.

(56) References Cited

U.S. PATENT DOCUMENTS

| | | | |
|---|---|---|---|
| 6,313,749 B1* | 11/2001 | Horne et al. | 340/575 |
| 6,416,483 B1* | 7/2002 | Halleck et al. | 600/561 |
| 6,575,902 B1* | 6/2003 | Burton | 600/300 |
| 7,496,457 B2 | 2/2009 | Fujita et al. | |
| 2002/0165694 A1* | 11/2002 | Chene et al. | 702/182 |
| 2004/0044293 A1 | 3/2004 | Burton | |
| 2004/0046666 A1* | 3/2004 | Yasuchi | 340/573.1 |
| 2004/0236235 A1 | 11/2004 | Fujita et al. | |
| 2004/0243013 A1* | 12/2004 | Kawachi et al. | 600/509 |
| 2004/0260440 A1* | 12/2004 | Fujita et al. | 701/36 |
| 2005/0148894 A1* | 7/2005 | Misczynski et al. | 600/513 |
| 2006/0122474 A1 | 6/2006 | Teller et al. | |
| 2006/0155175 A1* | 7/2006 | Ogino et al. | 600/301 |
| 2006/0173363 A1* | 8/2006 | Felder et al. | 600/485 |
| 2007/0078351 A1* | 4/2007 | Fujita | A61B 5/18 600/500 |
| 2007/0080816 A1* | 4/2007 | Haque et al. | 340/576 |
| 2007/0146131 A1* | 6/2007 | Boverie | 340/540 |
| 2007/0173705 A1 | 7/2007 | Teller et al. | |
| 2009/0192364 A1* | 7/2009 | Voto et al. | 600/301 |
| 2010/0174199 A1* | 7/2010 | Young et al. | 600/484 |
| 2010/0187881 A1 | 7/2010 | Fujita et al. | |
| 2012/0179008 A1 | 7/2012 | Burton | |

FOREIGN PATENT DOCUMENTS

| | | |
|---|---|---|
| JP | 2004 344613 | 12/2004 |
| JP | 2007 90032 | 4/2007 |
| JP | 2009 22610 | 2/2009 |
| WO | WO 00/44580 A1 | 8/2000 |
| WO | 2005 039415 | 5/2005 |
| WO | 2005 092193 | 10/2005 |
| WO | WO 2008099537 A1 * | 8/2008 |
| WO | 2008 143249 | 11/2008 |
| WO | 2009 104460 | 8/2009 |

OTHER PUBLICATIONS

Ochiai, N., et al., "The Application to Fatigue and Sleep Prediction, of The Signal of Biological Fluctuation Measured From Noninvasive Sensor," 39th Japan Ergonomics Society Chugoku and Shikoku Branch Convention, Total 2 Pages (Nov. 25, 2006).

Maeda, S., et al., "Trial Manufacture of Car Seat having a Non-Aggression Biological Signal Sensing Function," 39th Japan Ergonomics Society Chugoku and Shkoku Branch Convention, Total 2 Pages, (Nov. 25, 2006).

International Search Report dated Nov. 9, 2010 in PCT/JP10/68068 Filed Oct. 14, 2010.

* cited by examiner

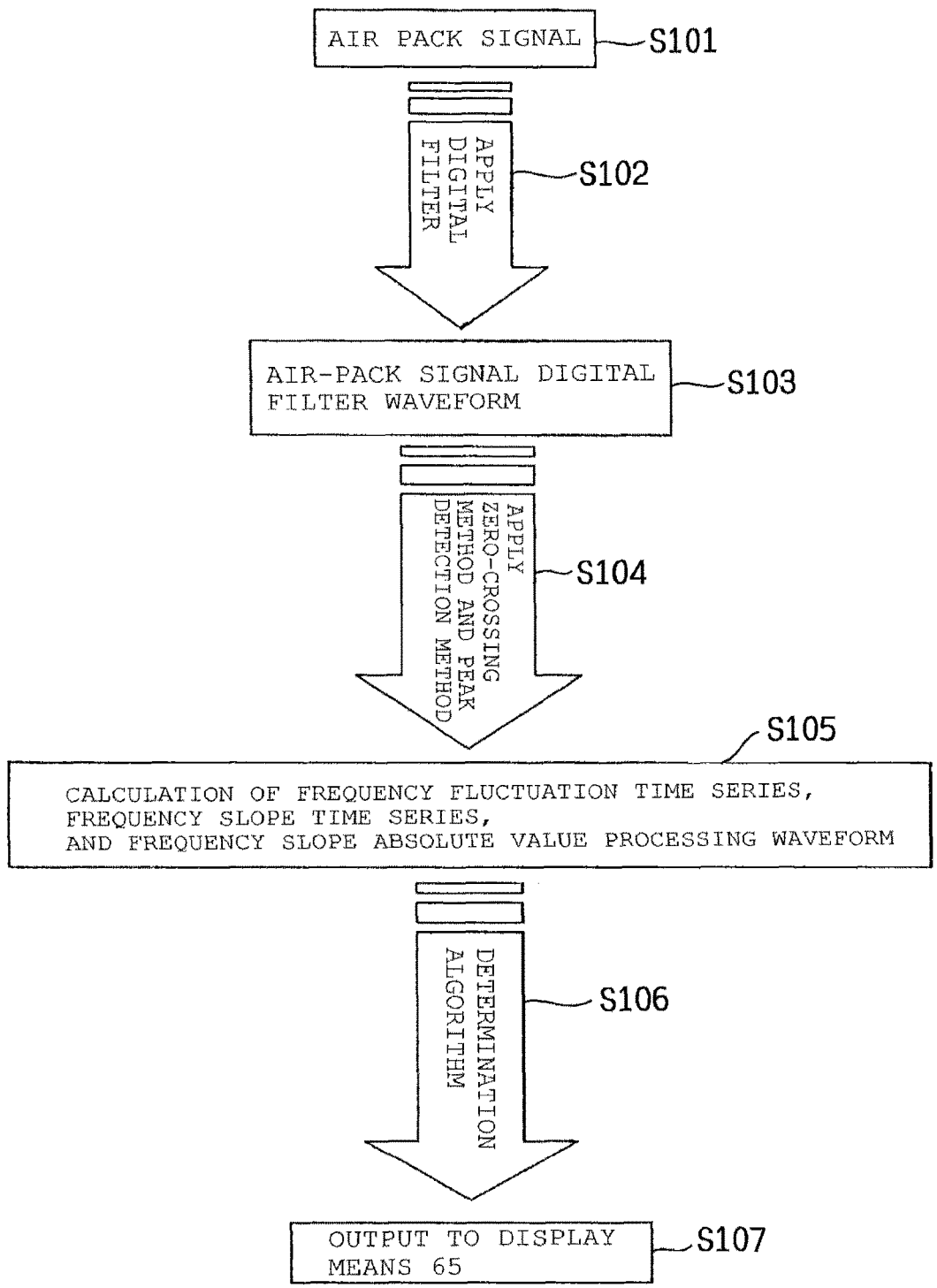

LEVEL HOMEOSTATIC OF FUNCTION

COMPARISON UNDER STATIC EQUIVALENT ENVIRONMENT (IDLING STATE)

COMPARISON DURING DRIVING

CASE 1

ACTIVE STATE

CASE 2

STATE IN WHICH PROGRESS OF FATIGUE IS FOUND

CASE 3

LOOMING STATE FREQUENTS AND HUMAN ERRORS CAN EASILY OCCUR, CARE SHOULD BE TAKEN IN DRIVING

CASE 4

LESS FLUCTUATION, HOMEOSTASIS CANNOT BE MAINTAINED EASILY, AND REST IS REQUIRED

CASE 5

OCCURRENCE OF MICROSLEEP IS PREDICTED

CASE 1
ACTIVE STATE

CASE 2
STATE IN WHICH PROGRESS OF FATIGUE IS FOUND

CASE 3
LOOMING STATE FREQUENTS AND HUMAN ERRORS CAN EASILY OCCUR, CARE SHOULD BE TAKEN IN DRIVING

CASE 4
REST IS REQUIRED

CASE 5
OCCURRENCE OF MICROSLEEP IS PREDICTED

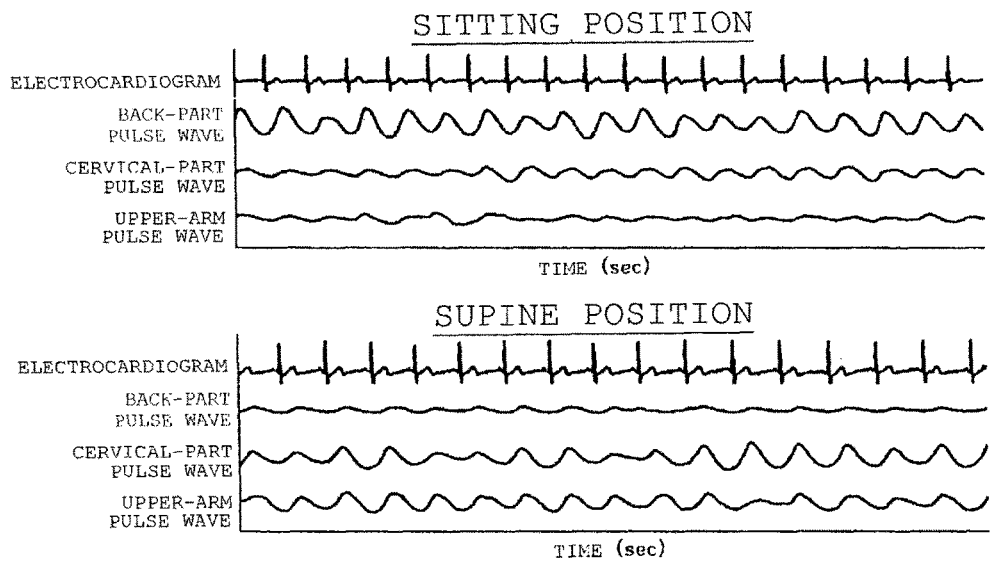
FIG. 14A  ORIGINAL WAVEFORMS OF ELECTROCARDIOGRAM AND PULSE WAVE
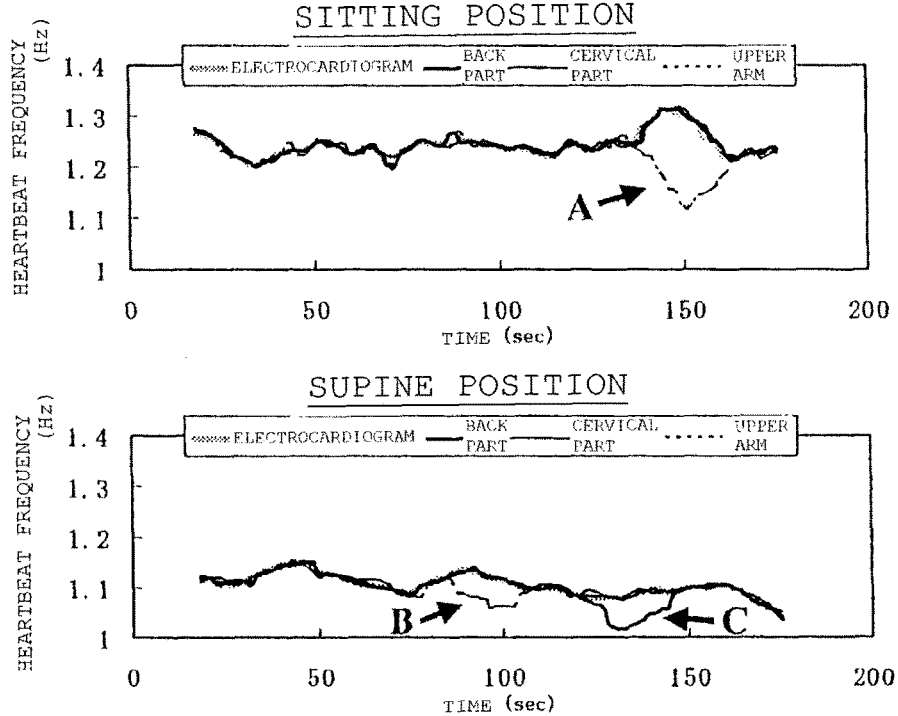
FIG. 14B  COMPARISON OF HEARTBEAT FREQUENCY TIME-SERIES WAVEFORM ns of the power value and the time-series waveform of the maximum Lyapunov exponent has taken phases opposite to each other and a waveform having a large amplitude at a low frequency has occurred in the time-series waveform of the slope of the power value is regarded as the sleep prediction phenomenon. According to this method, when a person sits on a seat, the sleep prediction phenomenon can be captured. Moreover, according to Patent Literatures 5 and 6, the fatigue degree of a person can be acquired.

However, skills are required to determine whether or not the sleep prediction phenomenon has occurred from a change in the waveform, and it is difficult for general drivers to determine the sleep prediction phenomenon by examining

BIOLOGICAL STATE ESTIMATION DEVICE, BIOLOGICAL STATE ESTIMATION SYSTEM, AND COMPUTER PROGRAM

TECHNICAL FIELD

The present invention relates to a technique for estimating a state of a biological body using a time-series waveform of a biological signal obtained from an upper body of a person.

BACKGROUND ART

Monitoring a biological body state of a driver during driving has attracted attention as a preventive measure against an accident or the like in recent years. The present applicant disclosed techniques of disposing a pressure sensor in a seat cushion section, obtaining and analyzing breech pulse waves, and determining a sleep prediction phenomenon in Patent Literatures 1 to 3.

Specifically, a maximum value and a minimum value of a time-series waveform of a pulse wave are obtained by a smoothing differentiation method of Savitzky and Golay, respectively. The maximum value and the minimum value are obtained for each 5 seconds so that their mean values are obtained. Using a square of a difference between the respective mean values of the maximum values and the minimum values obtained as a power value, the power value is plotted for each 5 seconds so that a time-series waveform of the power value is produced. In order to read a global change of the power value from this time-series waveform, a slope of the power value regarding a certain time window Tw (180 seconds) is obtained by least-square method. Next, the slope regarding the next time window Tw is similarly calculated in an overlapped time TI (162 seconds) and the calculation results are plotted. A time-series waveform of the slope of the power value is obtained by repeating this calculation (movement calculation) sequentially. On the other hand, the maximum Lyapunov exponent is obtained by applying Chaos analysis to the time-series waveform of the pulse wave, a maximum value is obtained by a smoothing differentiation like the above, and a time-series waveform of a slope of the maximum Lyapunov exponent is obtained by conducting movement calculation.

Then, the time-series waveform of the slope of the power value and the time-series waveform of the slope of the maximum Lyapunov exponent take phases opposite to each other, and a waveform having a large amplitude at a low frequency in the time-series waveform of the slope of the power value is determined as a characteristic signal indicating a sleep prediction and a point at which the amplitude has become small thereafter is determined as a sleep-onset point.

Further, as Patent Literature 4, a system provided with an airbag (air pack) including a three-dimensional solid fabric inserted therein, where the air pack is disposed at a site corresponding to a waist portion of a person, an air pressure fluctuation in the air pack is measured, a biological signal of the person is detected from the time-series waveform of the air pressure fluctuation obtained, and the biological body state of the person is analyzed is disclosed. Further, in Non-Patent Literatures 1 and 2, trials for detecting a biological signal of a person by disposing an air pack sensor along a lumber iliocostal muscle are reported. This air pressure fluctuation of the air pack is caused by fluctuation in a downward aorta with movement of a heart, and a state change closer to the movement of the heart than use of the breech pulse waves in Patent Literatures 1 and 2 can be captured.

Moreover, the present applicant also proposes the technique of applying absolute value processing to the time-series signal of the slope of the power value to calculate an integral value and obtaining a fatigue degree from the integral value as Patent Literature 5. Furthermore, the applicant proposes a technology in which a fatigue degree closer to sensory evaluation is acquired, to which mental fatigue is added, by considering a compensation action for fatigue by sympathetic nerve activities using time-series data of maximum Lyapunov exponent in addition to the method of mainly acquiring a physical fatigue degree by using time-series data of a power value as Patent Literature 6.

PRIOR ART LITERATURES

Patent Literature

Patent Literature 1: Japanese Patent Application Laid-Open No. 2004-344612
Patent Literature 2: Japanese Patent Application Laid-Open No. 2004-344613
Patent Literature 3: WO2005/092193A1
Patent Literature 4: Japanese Patent Application Laid-Open No. 2007-90032
Patent Literature 5: WO2005/039415A1
Patent Literature 6: Japanese Patent Application Laid-Open No. 2009-295384

Non-Patent Literatures

Non-Patent Literature 1: "APPLICATION OF BIOLOGICAL WANDERING SIGNAL MEASURED BY NON-INVASIVE TYPE SENSOR TO FATIGUE AND SLEEP PREDICTION" by Naoki OCHIAI (and six others), 39th Japan Ergonomics Society Chugoku and Shikoku Branch convention, Collection of Literatures and Papers issued on Nov. 25, 2006 from Japan Ergonomics Society Chugoku and Shikoku Branch Secretariat
Non-Patent Literature 2: "TRIAL PRODUCTION OF VEHICLE SEAT HAVING NON-INVASIVE BIOLOGICAL SIGNAL SENSING FUNCTION" by Shinichiro MAEDA (and four others), 39th Japan Ergonomics Society Chugoku and Shikoku Branch Convention, Collection of Literatures and Papers issued on Nov. 25, 2006 from Japan Ergonomics Society Chugoku and Shikoku Branch Secretariat

SUMMARY OF INVENTION

Technical Problem

As described above, in the techniques described in Patent Literatures 1 to 4 and Non-Patent Literatures 1 and 2, the time where the time-series waveform of the slope of the power value and the time-series waveform of the slope of the maximum Lyapunov exponent has taken phases opposite to each other and a waveform having a large amplitude at a low frequency has occurred in the time-series waveform of the slope of the power value is regarded as the sleep prediction phenomenon. According to this method, when a person sits on a seat, the sleep prediction phenomenon can be captured. Moreover, according to Patent Literatures 5 and 6, the fatigue degree of a person can be acquired.

However, skills are required to determine whether or not the sleep prediction phenomenon has occurred from a change in the waveform, and it is difficult for general drivers to determine the sleep prediction phenomenon by examining the waveform change. Thus, the above Patent Literatures employ means for notification by operating some alarm device (a buzzer sound, vibration in a seatback and the like, for example) when the opposite phase of the time-series waveform occurs or the like. Moreover, the fatigue degree in Patent Literatures 5 and 6 is determined on the basis of a graph in which the fatigue degree steadily increases over time. Therefore, in this case, too, it is not easy for a driver to grasp a degree of his/her own fatigue by examining the graph if this graph is displayed on a monitor mounted on an automobile, for example. It might be different for those who are accustomed to determining the fatigue degree on the basis of this graph, but otherwise, the driver needs to be notified by an alarm of sound or the like at some inflection point such as time when the fatigue degree has reached a certain numerical value or more.

Moreover, the prior-art methods are all based on determination mainly of a state caused by metabolic change of a person. That is, the process during which a body is getting tired one-sidedly as time elapses is mainly examined. However, it is considered that, a contribution rate of mental fatigue is high in a tensed state, while physical fatigue governs the progress of fatigue in a relaxed state. However, in the prior-art methods, suppression of fatigue by activation of a brain function is not considered. In a general driving environment, the brain function is activated regardless of the degree of progress of fatigue. This activation of the brain function includes creativity, curiosity and the like, and they induce awakening. As in Patent Literature 6, the fatigue degree to which the mental fatigue is added is acquired, considering the compensation action for fatigue by the sympathetic nerve activities by using time-series data of the maximum Lyapunov exponent in addition to the method of acquiring the physical fatigue degree, but even in this case, only the process of fatigue increasing one-sidedly and the compensation action by the sympathetic nerve are outputted, and whether or not the brain function has been activated is not captured.

The present invention was made in view of the above and has an object to provide a biological body state estimation device, a biological body state estimation system, and a computer program which can capture not only the activities of autonomous nerves but also the activated state of the brain function and which enables easy visual understanding of a homeostatic function level of a person by examining display means, whereby the degree of progress of fatigue can be also grasped.

Solution to Problem

In order to solve the above problems, a biological body state estimation device of the present invention is a biological body state estimation device for estimating a state of a person using a biological signal obtained from an upper body of a person by using biological signal measuring means and includes homeostatic function level computing means that analyzes the biological signal, and acquires and sorts the homeostatic function level of a person at a predetermined point of time into a plurality of stages and output means that plots the homeostatic function level acquired by the homeostatic function level computing means in a time series by taking each stage of the homeostatic function level on the vertical axis and time on the lateral axis and displays a fluctuation degree of the homeostatic function level on display means as a graph.

It is preferred that the homeostatic function level computing means acquires and sorts the homeostatic function level into a range of 3 to 10 stages from a highly active state to a functional decline state, and the output means sorts and displays the level in a range of 3 to 10 stages on the vertical axis with the highly active state as the highest part and the functional decline state as the lowest part. It is preferred that the homeostatic function level computing means acquires and sorts the homeostatic function level into five stages from the highly active state to the functional decline state and the output means sorts and displays the level into five stages on the vertical axis with the highly active state as the highest part and the functional decline state as the lowest part.

It is preferred that determining means that determines a change in the state of a person from a graph displayed on the display means by the output means is further provided. The determining means preferably has abnormal state determining means that determines an abnormal state if a rapid decline over two stages or more of the homeostatic function level occurs a predetermined number of times or more on the graph displayed on the display means by the output means.

The homeostatic function level computing means preferably includes:

frequency computing means that acquires a frequency of a biological signal obtained by the biological signal measuring means;

frequency slope time-series analyzing and computing means that conducts a movement calculation to acquire a slope of the frequency for each predetermined time window set with a predetermined overlapped time from the frequency of the biological signal obtained by the frequency computing means and acquires a time-series waveform of the slope of the frequency obtained for each time window;

differentiating means that differentiates the time-series waveform of the frequency slope acquired by the frequency slope time-series analyzing and computing means;

integrating means that integrates the time-series waveform of the frequency slope acquired by the frequency slope time-series analyzing and computing means;

rectangular wave calculating means that acquires a rectangular wave from increase/decrease of the time-series waveform of the frequency slope acquired by the frequency slope time-series analyzing and computing means;

describing function calculating means that acquires a describing function and a describing function amplitude value between the frequency slope time-series waveform in an arbitrarily set first time zone and the frequency slope time-series waveform in a second time zone after the first time zone;

absolute value processing means that applies absolute value processing to the time-series waveform of the respective frequency slopes acquired by the frequency slope time-series analyzing and computing means by using a time-series waveform of a frequency of a biological signal using a maximum value of the time-series waveform of the biological signal obtained by the frequency computing means and a time-series waveform of a frequency of a biological signal using a zero-crossing point where the sign of the time-series waveform of the biological signal is switched; and homeostatic function stage calculating means that acquires the stage of the homeostatic function level by using at least one or more of the frequency slope acquired by the frequency slope time-series analyzing and computing means, the differential value acquired by the differentiating means, the integral value acquired by the integrating means, the sign of the rectangular wave acquired by the rectangular wave calculating means, the describing function amplitude value acquired by the describing function calculating means, and two absolute values of the frequency slope time-series waveform acquired by the absolute value processing means.

It is preferred that filtering means that filters the biological signal obtained by the biological signal measuring means in a predetermined frequency band before processing by the homeostatic function level computing means is further provided, and the filtering means is configured to set a frequency band for filtering by acquiring a mean frequency of the biological signal under a static environment measured by the biological signal measuring means and using the mean frequency as a reference value.

The biological signal measuring means is preferably provided with an air pack brought into contact with the back part of a person and whose pressure fluctuates with fluctuation in aorta caused by movement of the heart, and the homeostatic function level computing means preferably uses the pressure fluctuation of the air pack as the biological signal to be analyzed. In the case of application to a vehicle, the air pack is preferably equipped to a seatback section of an vehicle seat, and an onboard monitor can be used as the display means.

Moreover, the biological body state estimation system of the present invention is a biological body state estimation system provided with biological signal measuring means that obtains a biological signal from an upper body of a person and a biological body state estimation device that estimates the state of a person using the biological signal obtained by the biological signal measuring means, and the biological body state estimation device includes homeostatic function level computing means that analyzes the biological signal, and acquires and sorts a homeostatic function level of a person at a predetermined point of time into a plurality of stages and output means that plots the homeostatic function level acquired by the homeostatic function level computing means in a time series with each stage of the homeostatic function level on the vertical axis and time on the lateral axis and displays a degree of fluctuation in the homeostatic function level on display means as a graph.

The biological signal measuring means is preferably provided with an air pack brought into contact with the back part of a person and whose pressure fluctuates with fluctuation in aorta caused by movement of the heart, and the homeostatic function level computing means preferably uses the pressure fluctuation of the air pack as the biological signal to be analyzed. In the case of application to a vehicle, the air pack is preferably equipped to a seatback section of an vehicle seat, and an onboard monitor can be used as the display means.

Moreover, the computer program of the present invention is a computer program incorporated in the biological body state estimation device that estimates the state of a person by using a biological signal obtained from the upper body of a person by the biological signal measuring means and includes a homeostatic function level computing step that analyzes the biological signal, and acquires and sorts the homeostatic function level of a person at a predetermined point of time into a plurality of stages and an output step that plots the homeostatic function level acquired by the homeostatic function level computing step in a time series with each stage of the homeostatic function level on the vertical axis and time on the lateral axis and displays it by the display means as a graph.

The graph displayed by the display means in the output step is preferably a line graph. It is preferred that the homeostatic function level computing step acquires and sorts the homeostatic function level into five stages from the highly active state to the functional decline state, and the output step sorts and displays the homeostatic function level in five stages with the highly active state as the highest part and the functional decline state as the lowest part on the vertical axis.

It is preferred that a determining step that determines a change in the state of a person from a graph displayed on the display means by the output step is further provided. The determining step preferably has an abnormal state determining step that determines an abnormal state if a decline over two stages or more of the homeostatic function level occurs a predetermined number of times or more on the graph displayed on the display means by the output step.

The homeostatic function level computing step preferably includes:

a frequency computing step that acquires a frequency of a biological signal obtained by the biological signal measuring means;

a frequency slope time-series analyzing and computing step that conducts a movement calculation to acquire a slope of the frequency for each predetermined time window set with a predetermined overlapped time from the frequency of the biological signal obtained by the frequency computing step and acquires a time-series waveform of the slope of the frequency obtained for each time window;

a differentiating step that differentiates the time-series waveform of the frequency slope acquired by the frequency slope time-series analyzing and computing step;

an integrating step that integrates the time-series waveform of the frequency slope acquired by the frequency slope time-series analyzing and computing step;

a rectangular wave calculating step that acquires a rectangular wave from increase/decrease of the time-series waveform of the frequency slope acquired by the frequency slope time-series analyzing and computing step;

a describing function calculating step that acquires a describing function and a describing function amplitude value between the frequency slope time-series waveform in an arbitrarily set first time zone and the frequency slope time-series waveform in a second time zone after the first time zone;

an absolute value processing step that applies absolute value processing to the time-series waveform of the respective frequency slopes acquired by the frequency slope time-series analyzing and computing step by using a time-series waveform of a frequency of a biological signal using a maximum value of the time-series waveform of the biological signal obtained by the frequency computing step and a time-series waveform of a frequency of a biological signal using a zero-crossing point where the sign of the time-series waveform of the biological signal is switched; and a homeostatic function stage calculating step that acquires the stage of the homeostatic function level by using at least one or more of the frequency slope acquired by the frequency slope time-series analyzing and computing step, the differential value acquired by the differentiating means, the integral value acquired by the integrating means, the sign of the rectangular wave acquired by the rectangular wave calculating means, the describing function amplitude value acquired by the describing function calculating step, and two absolute values of the frequency slope time-series waveform acquired by the absolute value processing step.

Advantageous Effects of Invention

The present invention has a configuration in which the homeostatic function level is sorted into a plurality of stages and acquired by using a biological signal obtained from the upper body of a person and each stage of the homeostatic function level is plotted in a time series in accordance with a time axis and displayed by the display means as a graph. The highest part on the vertical axis of the graph is preferably displayed as a highly active state and the lowest part as the functional decline state. Therefore, the state of fluctuation to maintain homeostasis by autonomous nerves and the state stimulated by the brain can be captured as a periodic function.

Moreover, if the homeostatic function level is displayed in a time series on a graph as above, when a person visually recognizes it, the decline state of the homeostatic function (progress of fatigue) can be easily grasped without requiring any skills. The act of looking at this graph which shows a change in the homeostatic function is an act to satisfy high-dimensional desire to know the state that cannot be subjectively or objectively grasped by himself/herself, and that activates the brain and can prevent the person from going to sleep. That is, the act of looking at the graph itself induces awakening. Therefore, the present invention is highly effective in promoting activation of the brain and is expected to realize an awakening inducing effect higher than the prior-art methods of stimulating an auditory sense by a buzzer sound, of stimulating a tactile sense/pressure sense such as vibration of the seatback and the like.

Moreover, a biological signal for acquiring the homeostatic function level in the present invention is detected by using a biological reaction of the upper body of a person, and thus, fluctuation in the aorta caused by movement of the heart can be captured. As a result, a homeostatic function which is a life sustaining function can be seen, and the state of a person can be grasped more accurately as compared with the technology for estimating the state of a person by using a digital pulse volume looking at adaptation capability to disturbance.

A cycle of the state change of a person is roughly divided into each state of awakening and sleep and a transitional state between those two states. A person changes from the highly active state to a fatigued state, that is, the function decline state via the transitional state to sleep or a so-called fatigue compensation period. After that, the person returns to the highly active state via the transitional state of a recovery period. In these transitional states, a sleep prediction signal and an awakening prediction signal occur. Also, a human body minimizes the change in energy consumed for metabolism by using circulation of blood in order to maintain homeostasis. The human body varies a frequency of heartbeat (heart rate) and a vessel diameter in order to change the circulation dynamic state of the blood. Therefore, transition of energy used for metabolism can be identified by detecting changes in the frequency fluctuation of the heartbeat and the vessel diameter. When the state of this transition is captured, the transition from the highly active state to the function decline state is captured, thus transition to sleep can be predicted. This state change is induced by the autonomous nerve system. An adaptation state to the external stimulation can be known by capturing this change through a reaction of the peripheral system, and quality and quantity of fatigue can be identified by capturing the reaction of the central system, that is, the fluctuation of the aorta caused by the movement of the heart.

Moreover, the decline of the homeostatic function level over 2 stages or more in the process of the graph indicates a rapid change in the energy level. By using the graph as in the present invention, such rapid drop can be visually recognized, and a person can become aware of a rapid change in the physical condition and try to induce himself/ herself into the highly active state or to actively take a rest. Moreover, it is more preferable to provide means for automatically determining an abnormal state (emergence of a sleep prediction signal) if such a rapid change as above occurs a predetermined number of times or more. If determined to be an abnormal state, stimulation by an auditory sense, pressure sense or the like can be used at the same time, such as emission of an alarm sound.

BRIEF DESCRIPTION OF DRAWINGS

FIG. 7 is a flowchart showing a process of state estimation by the biological body state estimation device;

FIG. 14A is a diagram showing a part of original waveforms of an air pack signal and an electrocardiogram in sitting position and a supine position in a test example 1, and FIG. 14B is a diagram showing a result of comparison between the heartbeat frequency time-series waveform calculated from the air pack signal and the electrocardiogram in a sitting position and a supine position;

DESCRIPTION OF EMBODIMENTS

Figure 1:
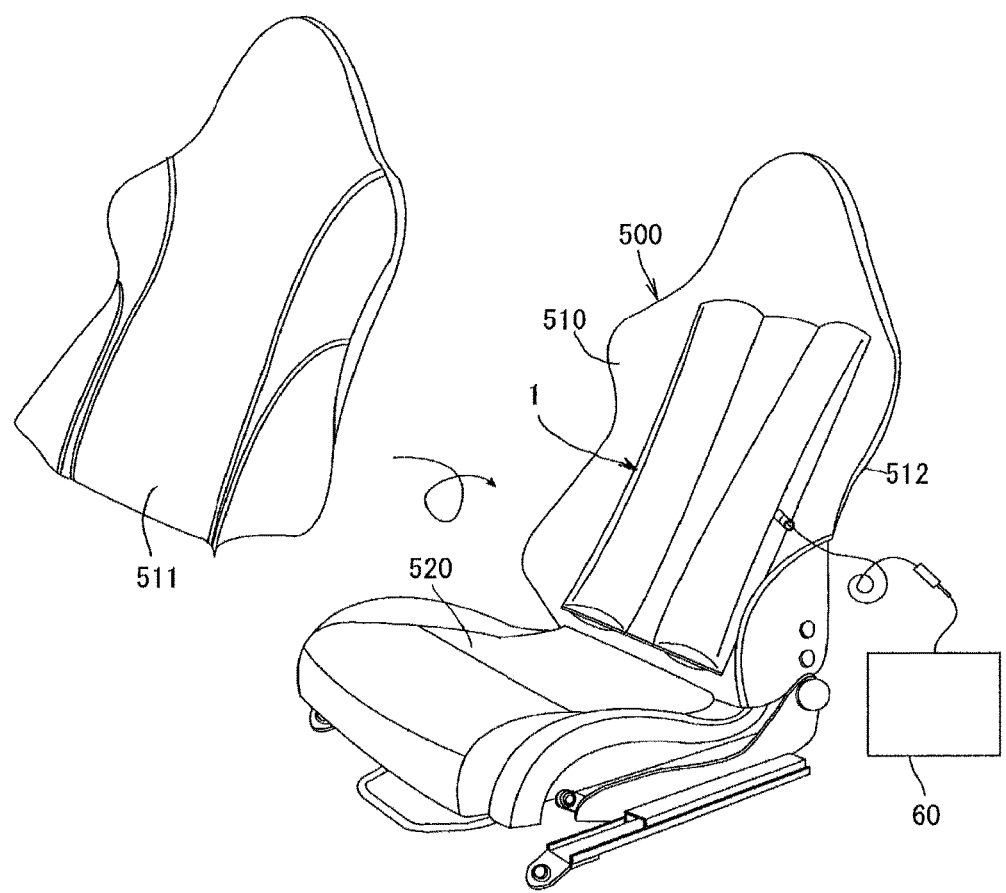
FIG. 1 is a view showing a state where biological signal measuring means according to an embodiment of the present invention is incorporated in a seat.

Hereinafter, embodiments of the present invention will be explained in detail with reference to the drawings. FIG. 1 is a view showing an exterior of an automobile seat 500 incorporating biological signal measuring means 1 obtaining a biological signal to be analyzed by a biological body state estimation device 60 according to this embodiment, that is, pressure fluctuation caused by fluctuation in aorta on the back part caused by movement of the heart. A biological body state estimation system is configured by the biological signal measuring means 1 and the biological body state estimation device 60. The biological signal measuring means 1 is used by being incorporated in a seatback section 510. Here, it is desirable that detection signals of pressure fluctuation obtained by the biological signal measuring means 1 contain less noise signals. Thus, the biological signal measuring means 1 of this embodiment has been designed to reduce noise signals contained in the sensor output signals themselves even under a vibration environment such as in a moving automobile and the like as described below.

The biological signal measuring means 1 is configured to include an air-pack unit 100 and an elastic member 20 made of expanded resin beads. The air-pack unit 100 is configured to include a receiving body 15 and two air packs 10 contained in the receiving body 15. Each of the air packs 10 is formed by connecting three small airbags 111 in the vertical direction, while air communication among these small airbags is prevented. Three-dimensional solid knitted fabrics 112 serving as resilience-imparting members are disposed within the respective small airbags 111.

In this embodiment, the air packs 10 are arranged on the right side and the left side. The arrangement of the air packs 10 on the right side and the left side makes contact with the back of a seated person bilaterally even, so that the person does not feel uncomfortable. Moreover, a sensor mounting tube 111a is provided on one of the small airbags 111 configuring one of the right and left air packs 10 and 10, and a sensor 111b which measures air pressure fluctuation is fixed inside thereof. The sensor mounting tube 111a is sealed. The small airbag 111 preferably has a size within a range of the width of 40 to 100 mm and the length of 120 to 200 mm to sensitively respond to air pressure fluctuation due to a biological signal. A material for the small airbag 111 is not limited, but the small airbag may be formed of a sheet made of, for example, polyurethane elastomer (for example, Product Number "DUS605-CDR" produced by Sheedom Co., Ltd.). As the sensor 111b, one which can measure air pressure within the small airbag 111 can be used, and a capacitive microphone sensor, for example, can be used.

As the size of the entirety composed of three small airbags 111 connected in series, it is preferred that the width and the entire length fall within a range of 40 to 100 mm and a range of 400 to 600 mm, respectively, when they are used in the seatback section 510 of the automobile seat 500. If the length is short, a seated person feels uncomfortable only at a portion close to his/her waist in the seatback section 510, and thus, it is preferred that the length is set to 400 mm or more so that the airbags accommodate the entire back of the seated person as much as possible.

In this embodiment, the sensor 111b which detects air pressure fluctuation is provided in the central small airbag 111 constituting the air pack 10 arranged on the left side of the seated person. The position of this small airbag 111 corresponds to a region where fluctuation in the aorta (particularly the "downward aorta") caused by the movement of the heart on the back of the seated person can be detected. The region where the movement of the aorta on the back is detectable is not uniform due to the body frame of a seated person, but as a result of measuring 20 subjects of various build from a 158-cm-tall Japanese woman to a 185-cm-tall Japanese man, the pressure fluctuation by the movement of the aorta could be detected in all the subjects when an intersecting portion P (See FIG. 2 and FIG. 3) of the side edge of the small airbag 111 (having a width of 60 mm and a length of 160 mm) positioned closer to the center of the seatback section 510 and a lower edge thereof was set such that a length L from an upper face of a seat cushion section 520 along a surface of the seatback section 510 was 220 mm and a distance M from the center of the seatback section 510 was 80 mm. When the size of the small airbag 111 is set such that its width is in a range of 40 to 100 mm and its length is in a range of 120 to 200 mm, it is preferred that the position of the intersecting portion P is set such that the length from the upper face of the seat cushion section 520 along the surface of the seatback section 510 is in a range of 150 to 280 mm and the distance from the center of the seatback section 510 is in a range of 60 to 120 mm.

Figure 2:
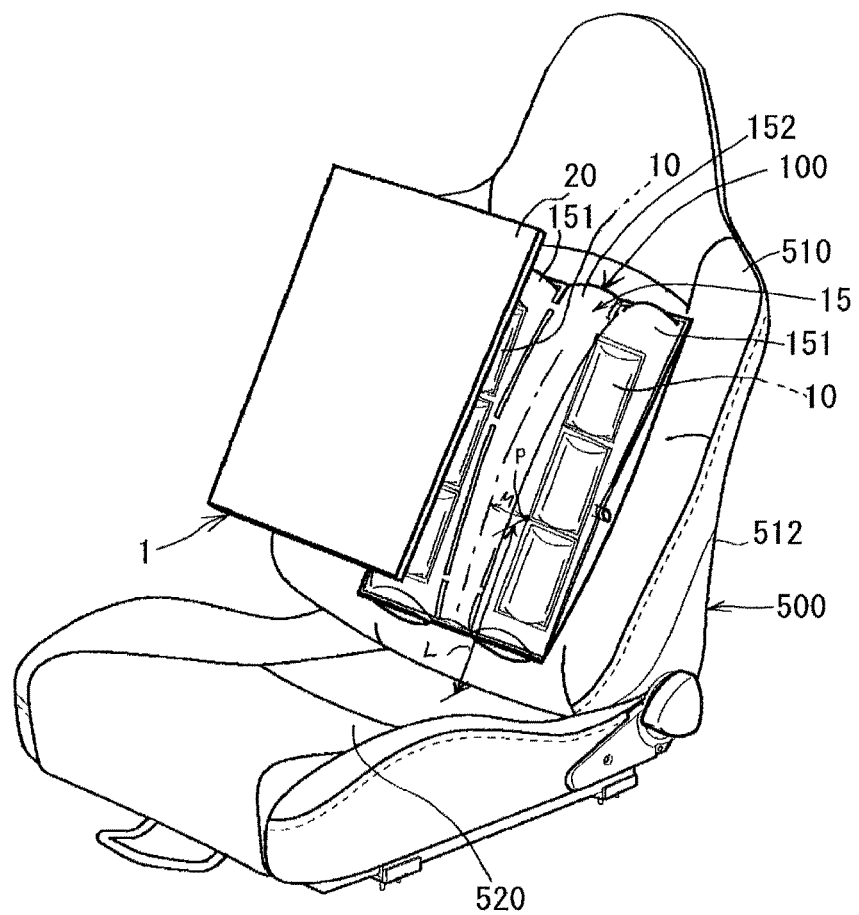
FIG. 2 is a view showing the biological signal measuring means according to the embodiment in more detail.
Figure 3A:
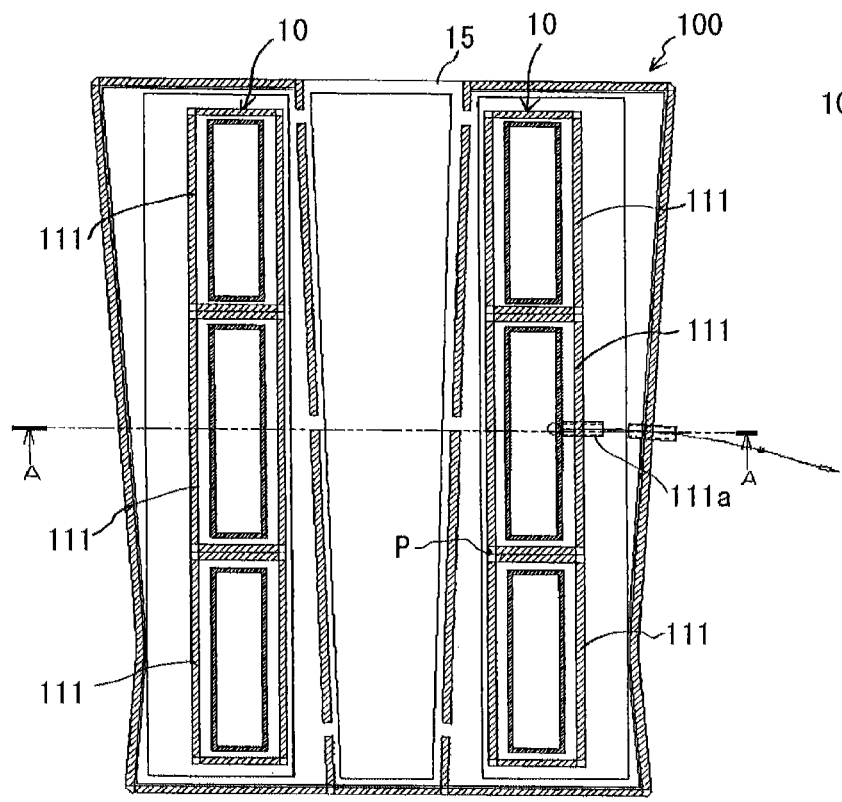
FIGS. 3A to 3D are views showing an air-pack unit, FIG. 3A being a sectional view of the air-pack unit as viewed from the front, FIG. 3B being a side view thereof, FIG. 3C being a bottom view thereof, and FIG. 3D being a sectional view of FIG. 3A taken along a line A-A.
Figure 3B:
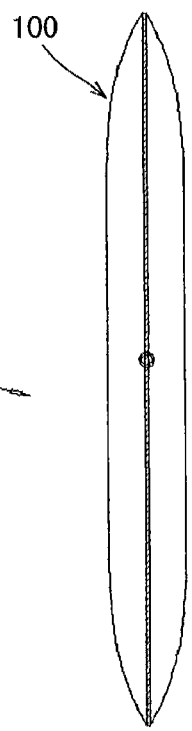
Figure 3C:
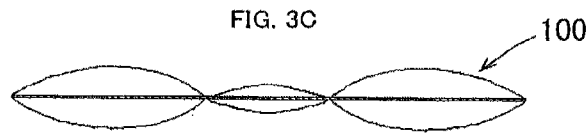
Figure 3D:
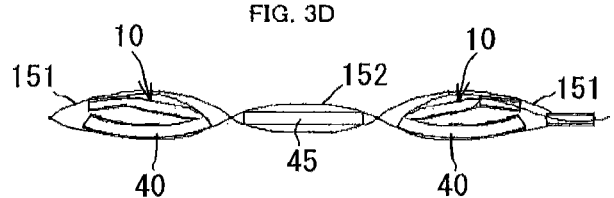
Figure 4:
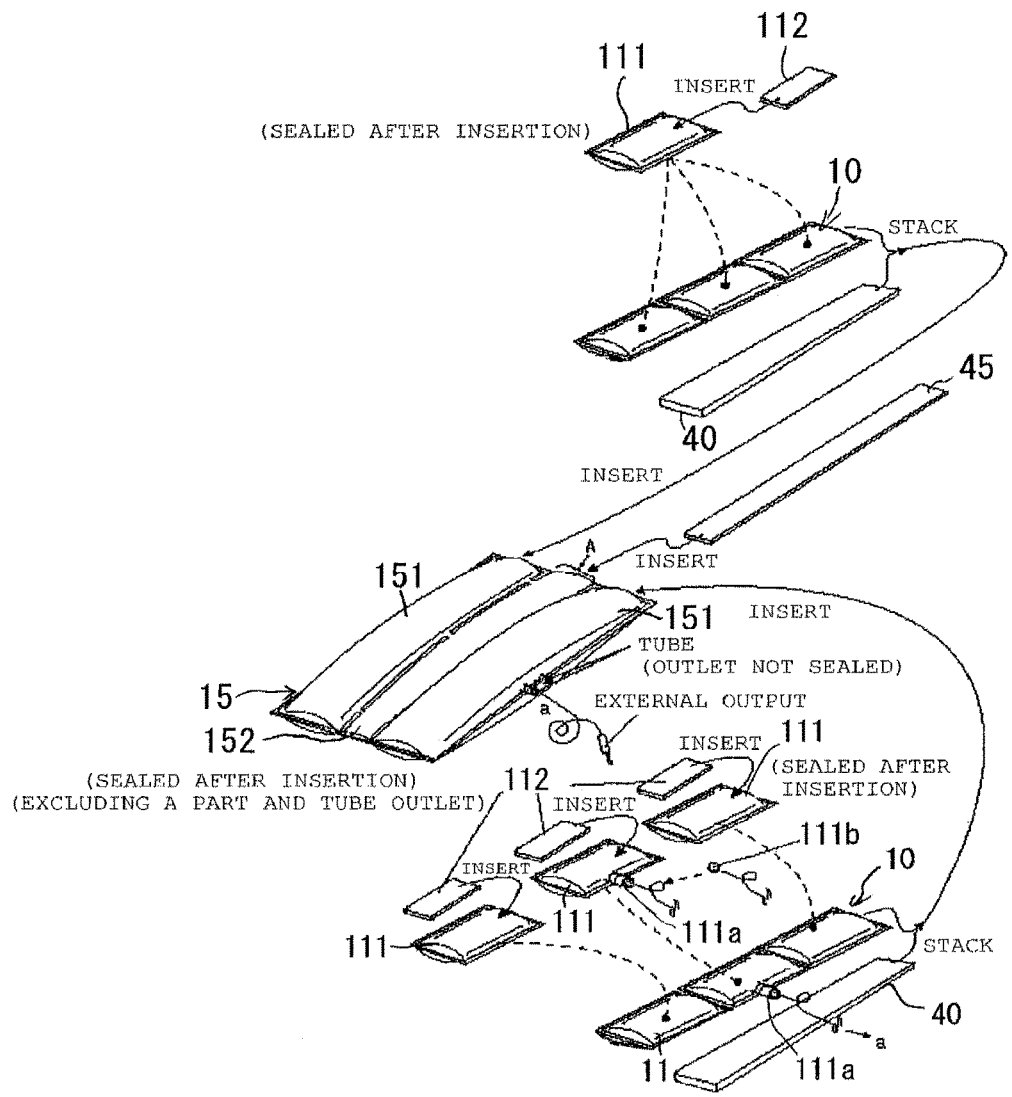
FIG. 4 is an exploded perspective view of the air-pack unit.
Figure 5A:
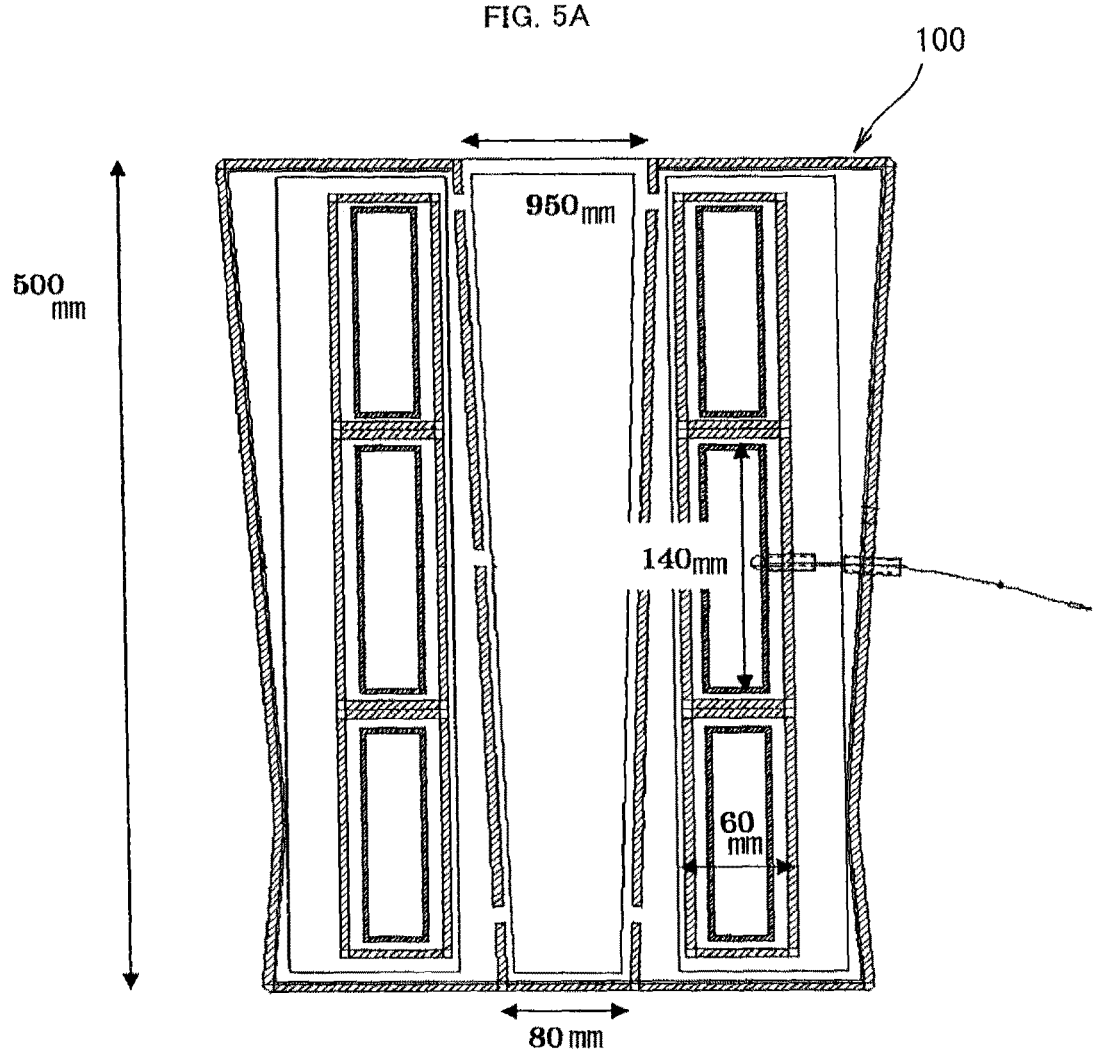
FIGS. 5A and 5B are views for describing a size of an air-pack unit used in a test example.
Figure 5B:
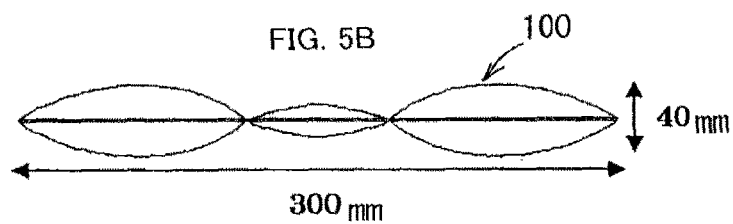

It is preferred that the above-described two air packs 10 are unitized such that they can be easily set at predetermined positions in the seatback section 510. Therefore, it is preferred that an air-pack unit 100 obtained by loading the air packs 10 into a receiving body 15 such as shown in FIG. 2 to FIG. 4 is configured. The receiving body 15 has bag-shaped air pack receiving portions 151 receiving the air pack 10 on both sides and, and it has a connecting portion 152 between two air pack receiving portions 151.

The air packs 10 are inserted into two air pack receiving portions 151, respectively. It is also preferred that a three-dimensional solid knitted fabric 40 with approximately the same size as the air pack 10 is inserted into the air pack receiving portion 151 so as to be positioned on a back face of the back surface side air pack 12 of the air pack 10 in a stacking state (see FIG. 3D). By arranging the three-dimensional solid knitted fabric 40, the air pack 10 is supported in a so-called floating manner by the three-dimensional solid knitted fabric 40, so that transmission of external vibrations from the seatback section 510 as pressure fluctuation in the air pack becomes difficult. That is, by arranging the three-dimensional solid knitted fabric 40, a spring-mass-damper system with a low spring constant is produced within the air pack from piles of the three-dimensional solid knitted fabric 40 and fluctuation of air pressure at an inputting time of high-frequency external vibrations with small amplitude. Then, the spring-mass-damper system serves as filters to low-frequency and high-frequency inputs (a low-pass filter and a high-pass filter) in the air pack 10 housing the three-dimensional solid knitted fabric 40 therein to damp the external vibrations.

The connecting portion 152 may be a member which can support two air packs 151 spaced from each other by a predetermined distance, and it is formed to have a width of about 60 to 120 mm. It is preferred that the connecting portion 152 is formed in a bag shape, so that a three-dimensional solid knitted fabric 45 is inserted therein (see FIG. 3D and FIG. 4). Thereby, vibrations inputted through the connecting portion 152 can also be removed effectively by inserting the three-dimensional solid knitted fabric 45 into the connecting portion 152, so that transmission of external vibrations to the air pack 10 provided with the sensor 111*b* can be suppressed.

Incidentally, as described above, the small airbag 111 can be formed of a sheet made of, for example, polyurethane elastomer (for example, Product Number "DUS605-CDR" produced by Sheedom Co., Ltd.), but it is preferred that the receiving body 15 are also made of the same material as that for the small airbag 111. The respective three-dimensional solid knitted fabrics loaded into the small airbags 111, the air pack receiving portion 151, and the connecting portion 152 are knitted fabrics having a solid three-dimensional structure having a pair of ground knitted fabrics arranged so as to be spaced from each other and many connecting strands reciprocating between the pair of ground knitted fabrics to connect both the ground knitted fabrics, as disclosed in Japanese Patent Application Laid-Open No. 2002-331603.

One of the ground knitted fabrics is formed of, for example, a flat knitted fabric texture (fine mesh) continuous both in a wale direction and in a course direction from strands obtained by twisting monofilaments, while the other ground knitted fabric is formed of, for example, a knitted stitch structure having a honeycomb shape (hexagonal shape) meshes from strands obtained by twisting monofilaments. Of course, the knitted fabric texture is arbitrary, and a knitted fabric texture other than the fine mesh texture or the honeycomb shape can be adopted, and any combination of knitted fabric textures such as adoption of the fine mesh texture in both the ground knitted fabrics can be adopted in both the ground knitted fabrics. The connecting strands are knitted between the two ground knitted fabrics such that one of the ground knitted fabrics and the other are kept away from each other by a predetermined distance.

The elastic member made of expanded rein beads 20 is disposed between a skin member of the seatback section 510 and the receiving body 15 (air-pack unit 100) which has received the air packs 10 therein. It has a length corresponding to the entire length of two air packs 10 and it has a width corresponding to a length between top portions of two air packs 10. Therefore, it is preferred that members having such a size that a length is in a range of 400 to 600 mm and a width is in a range of about 250 to 350 mm are used. Thereby, since two air packs 10 are covered with these members, undulation feeling due to the two air packs 10 is reduced.

The elastic member made of expanded resin beads 20 is composed of an expanded bead body formed in a flat-plate shape and a covering material caused to adhere to an outer face of the expanded bead body. As the expanded bead body, an expanded formation body obtained by a bead method of resin containing at least one of polystyrene, polypropylene, and polyethylene is used. Incidentally, an expansion ratio is set arbitrarily and it is not limited. The covering material is caused to adhere to an outer face of the expanded bead body by adhesive, and it is a material having a high extension percentage and a high recovery rate, so that an elastic fiber nonwoven fabric whose extension percentage is at least 200% and whose recovery rate at 100% extension time is 80% is preferably used. For example, a nonwoven fabric where thermoplastic elastomer elastic fibers have been caused to adhere to one another in a melting manner, which is disclosed in Japanese Patent Application Laid-Open NO. 2007-92217, can be used. Specifically, Trade Name "Espansione" produced by KB SEIREN, LTD. can be used.

Also, as a covering material for covering an outer face of the elastic member made of expanded resin beads 20, for example, a nonwoven fabric made of thermoplastic polyester can be used. Specifically, a biaxial fabric (longitudinal: 20/inch, horizontal: 20/inch) formed from polyethylene naphthalate (PEN) fibers (1100 dtex) produced by TEIJIN LIMITED can be used.

As an expanded bead constituting the elastic member made of expanded resin beads 20, those having a thickness of approximately 5 to 6 mm can be used, and the expanded resin beads are formed by bonding an unwoven cloth made of the above-described elastic fiber or an unwoven cloth made of thermoplastic polyester having a thickness of approximately 1 mm or less. In this embodiment, the above-described "Espansione" (product name) is bonded to the surface opposing the skin member 511 of the elastic member made of expanded resin beads 20 and the opposite surface thereof. As a result, transmission performance of the biological signal is improved.

In the embodiment, the seatback section 510 of the seat 500 configuring a human body supporting unit is provided with the skin member 511 and a cushion supporting member 512 disposed on a back surface side of the skin member 511, and the receiving body 15 (air-pack unit 100) holding the air packs 10 and the elastic members made of expanded resin beads 20 are assembled between the skin member 511 and the cushion supporting member 512. At this time, the receiving body 15 (air-pack unit 100) holding the air packs 10 is first disposed on the side of the cushion supporting member 512, and the elastic member made of expanded resin beads 20 is disposed on a surface side of the receiving body 15, these members are covered with the skin member 511. Incidentally, the cushion supporting member 512 can be formed by stretching a three-dimensional solid knitted fabric between rear end edges of a pair of right and left side frames of the seatback section 510 or can be formed of a synthetic resin plate. The skin member 511 can be provided by stretching, for example, a three-dimensional solid knitted fabric, an artificial leather, a leather, or a laminated body of these members between front edges of the pair of right and left side frames.

In this embodiment, thus, since the configuration where the elastic member made of expanded resin beads 20 which has predetermined sizes is disposed on the back surface side of the skin member 511 in a stacking state and the receiving body 15 (air-pack unit 100) holding the a pair of right and left air packs 10 is further disposed behind them is adopted, a person sitting on the seat is prevented from feeling undulation of the air packs 10 on his/her back, and sitting feeling is improved though the configuration having the air packs 10 for measuring biological signals is adopted. In the above-described explanation, only one sheet of the elastic member made of expanded resin beads 20 is used, but it is also possible to arrange a plurality of stacked sheets.

The above-described biological signal measuring means 1 incorporates the air-pack unit 100 in the seatback section 510 of the seat 500 but the air-pack unit 100 may be incorporated in a cushion for a seat attached later on the surface of the seatback section 510. Moreover, the three small airbags 111 forming the air pack 10 are connected in series but the number of the small airbags 111 may be 2 or 1. Moreover, the biological signal measuring means 1 can be configured only of the air pack 10 made of a single airbag, for example, as long as it can be used by being arranged at a position where fluctuation in the aorta on the back part can be captured. Moreover, the above sizes are an appropriate example when three small airbags 111 connected in series are used, and it is needless to say that the size of the air pack 10 and the size of the air-pack unit 100 are not limited at all as long as the fluctuation of the aorta on the back part can be captured.

Figure 6:
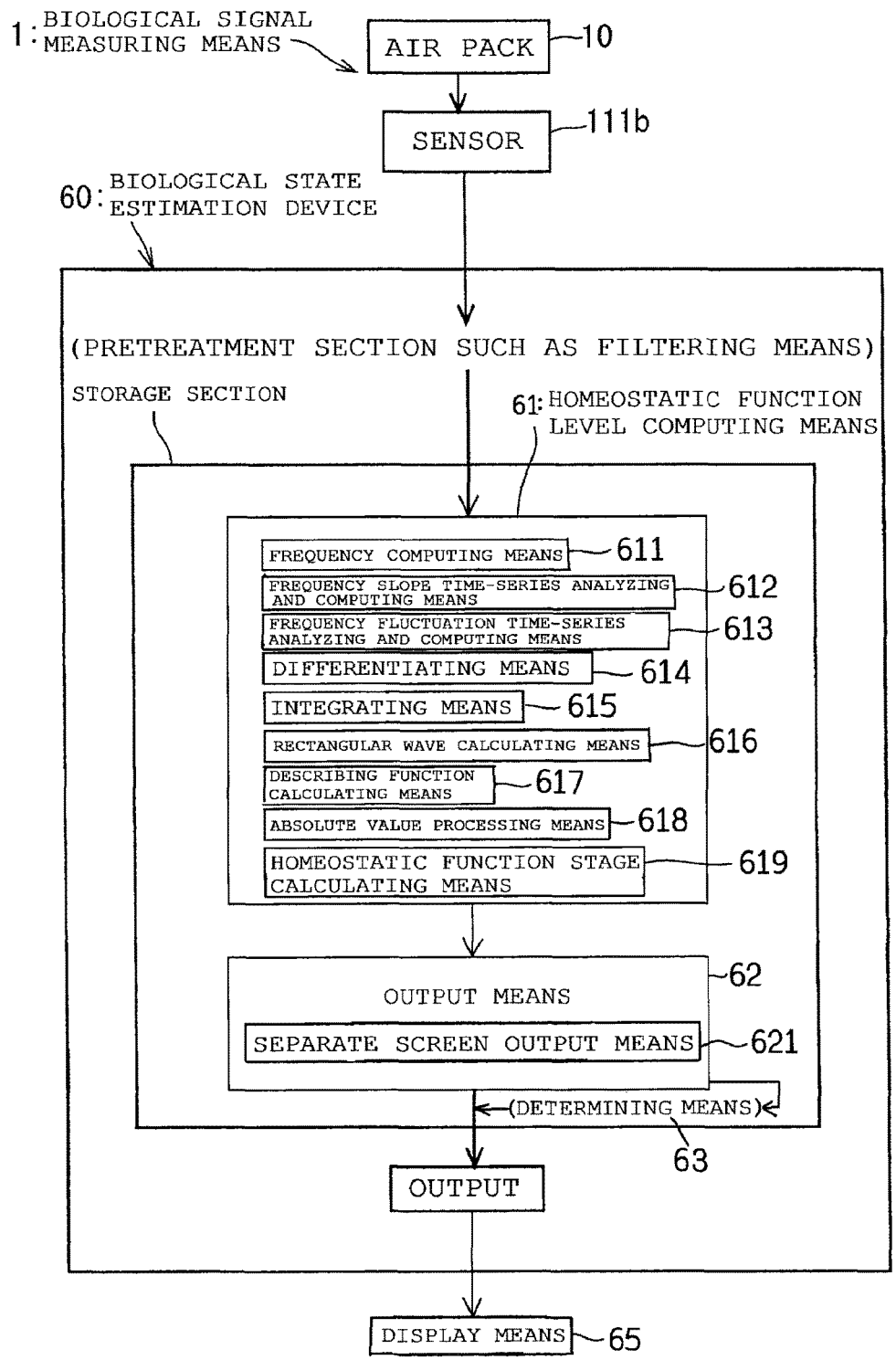
FIG. 6 is a diagram showing a configuration of a biological body state estimation device according to the embodiment.

Subsequently, a configuration of the biological body state estimation device 60 will be described on the basis of FIG. 6. The biological body state estimation device 60 is configured to include homeostatic function level computing means (homeostatic function level computing step) 61 formed of a computer program set in a storage section such as a hard disk and output means (output step) 62. The computer program can be provided by being stored in a recording medium such as a flexible disk, a hard disk, a CD-ROM, a MO (magnetoptic disk), a DVD-ROM, a memory card and the like or can be also transmitted via a communication line.

The homeostatic function level computing means (homeostatic function level computing step) 61 is means for analyzing a state of a person from a time-series waveform of a pressure fluctuation signal (hereinafter referred to as an "air pack signal" depending on a case) caused by movement of the aorta on the back part detected by the biological signal measuring means 1 and sorting the homeostatic function level at a predetermined point of time into a plurality of stages and acquiring the homeostatic function level. The state of a person is roughly divided into a highly active state and a function decline state as described above and a steady state is included between the both, and a transitional state is present between each of these states. However, in this embodiment, the homeostatic function level is divided into five stages from the highly active state to the function decline state. That is, a state in which a person is the most active and does not feel fatigue while he/she is awake (highly active state) to a state in which the person feels fatigue (function decline state) are divided into five stages of the homeostatic function level. The level is divided into five stages in this embodiment, but this is not limiting. However, if the level is divided into two stages, a rapid decline over two stages or more in the homeostatic function level which detects an abnormal state (sleep prediction signal) cannot be indicated, while if the level is divided into 10 stages or more, the stages are too fine to be visually recognized, and thus, division into 3 to 10 stages is preferable. Division into five stages is more preferable. Details of how to acquire the homeostatic function level by the homeostatic function level computing means 61 will be described later.

The output means (output step) 62 displays a plot area having each stage of the homeostatic function level on the vertical axis and time on the lateral axis on display means 65. Then, the homeostatic function level acquired by the homeostatic function level computing means 61 is plotted on this plot area in a time series corresponding to calculated time and displayed as a line graph. By plotting the homeostatic function level in a time series, a periodic function of the state of fluctuation to maintain homeostasis by autonomous nerves and activation by the brain is expressed.

The homeostatic function level on the vertical axis is, as illustrated in FIG. 11, displayed in division into five stages in this embodiment. Specifically, the highly active state (state in which a person is the most active and does not feel fatigue while awake) is displayed on the highest part, while the function decline state is displayed on the lowest part, and three stages of the homeostatic function stages are displayed between the both. Here, the center part (third from the top) is set as a steady state, the second from the top as a state between the highly active state and the steady state, and the second from the bottom is set as a state between the steady state and the function decline state, and images of the states are expressed by figures imitating faces of a person. For convenience of explanation, the highest part which is the most active state is referred to as the homeostatic function stage 1 (highly active state (state in good condition: expressed as "feeling good")), the homeostatic function stage 2 (relatively good state: expressed as "OK" or the like)), the homeostatic function stage 3 (steady (ordinary) state), the homeostatic function stage 4 (slightly functional decline: expressed as "drive carefully" or the like), and the homeostatic function stage 5 (functionally declined state: expressed as "fatigued state" or the like)) in the order downward.

FIGS. 11A to 11E show examples of the homeostatic function level of a driver expressed by line graphs on the display means 65 by the output means 62. These are graphs organizing test data of a plurality of subjects and indicating the tendencies. As the display means 65, an onboard monitor mounted at a position that can be easily seen from a driver's seat on an automobile is preferably used.

Figure 11A:
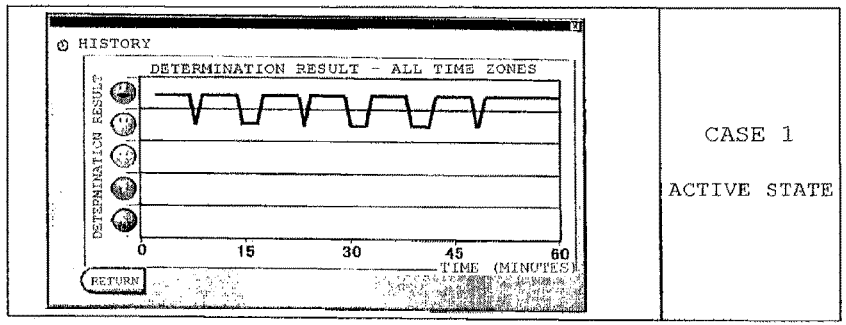
FIGS. 11A to 11E are diagrams showing examples of acquiring a homeostatic function level of a driver and displaying it by line graphs on display means by output means.

The example in FIG. 11A shows that, while the graph is basically drawn within a range of the homeostatic function stage 1 which is the most active state, the state changes to the homeostatic function stage 2 every 5 to 8 minutes and then, returns to the homeostatic function stage 1 repeatedly. If a person continues to maintain the homeostatic function stage 1 for a long time, the active state is maintained with a sense of tension. If a person is in a highly focused state due to tension or relaxed but highly focused, active and comfortable, a waveform fluctuates between the homeostatic function stage 1 and the homeostatic function stage 2 by means of the homeostatic function through action of the autonomous nerves. Between them, if the number of sessions of fluctuation is large, it indicates the relaxed state, while less fluctuation indicates the tensed state.

Figure 11B:
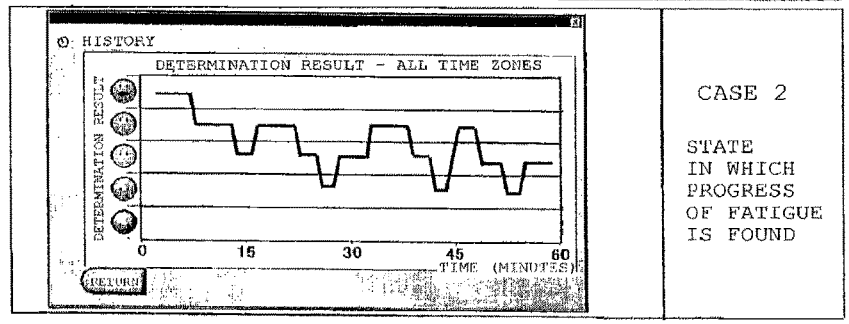

The example in FIG. 11B is a waveform in which the homeostatic function stage 1 changes into the homeostatic function stage 2 and fatigue gradually increases with fluctuation sequentially going back and forth through the homeostatic function stages such as from the homeostatic function stage 3, to the homeostatic function stage 2, the homeostatic function stage 3, the homeostatic function stage 4, the homeostatic function stage 3, and the homeostatic function stage 2. That is, the homeostatic function sequentially lowers with progress of the physical fatigue and a rest with sleep will be needed in the end. This is a case indicating a progress of usual fatigue without an extreme state change.

Figure 11C:
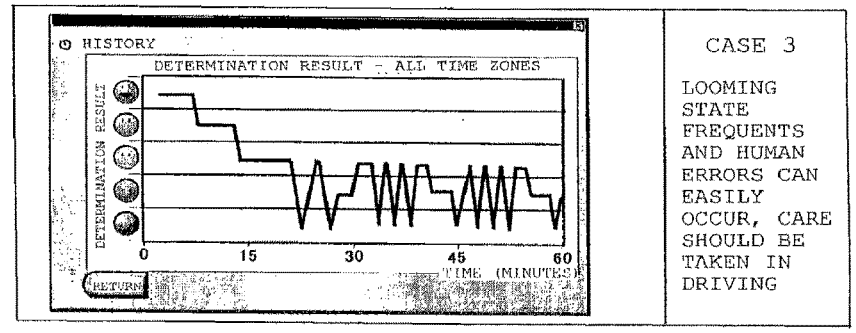

The example in FIG. 11C shows a case in which the fatigue progresses all at once such as from the homeostatic function stage 1 at the start of driving to the homeostatic function stage 2, the homeostatic function stage 3, and the homeostatic function stage 5. Since the fatigue progresses to the homeostatic function stage 5, the function to forcedly return the stage to the homeostatic stage 3 by the action (compensation action) of the sympathetic nerves, but after that, the state changes between the homeostatic function stage 5 and the homeostatic function stage 3 in an extremely short time. This indicates a looming state between sleepiness and a resting state, in which a human error can occur easily, and it is determined to be a state in which the driver should drive carefully.

Figure 11D:
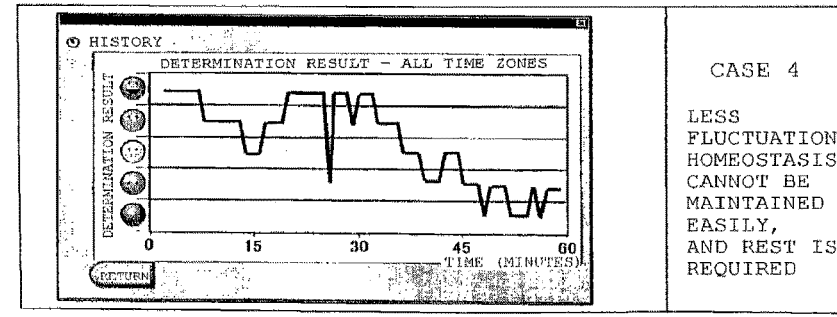

The example in FIG. 11D indicates that the state returns from the homeostatic function stage 3 to the homeostatic function stage 1 by the sympathetic nerve compensation action after 15 minutes, but the state progresses from the homeostatic function stage 1 to the homeostatic stage 5 substantially one-sidedly with little fluctuation after 30 minutes. This indicates that maintenance of the homeostasis becomes increasingly difficult and it can be determined to be a state requiring rest at an early stage.

Figure 11E:
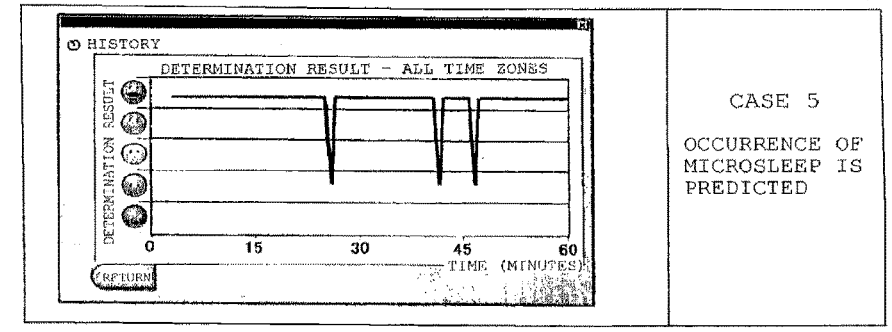
Figure 12A:
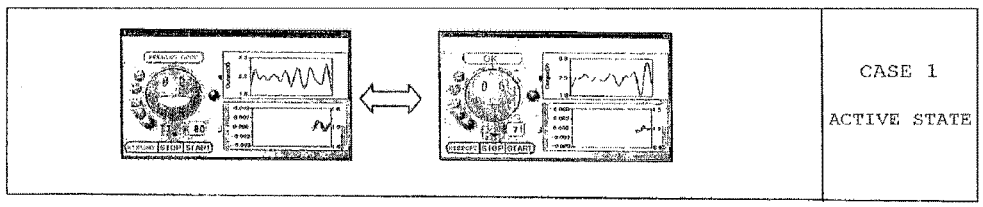
FIGS. 12A to 12E are views showing change examples of images outputted on the display means by separate screen output means.
Figure 12B:
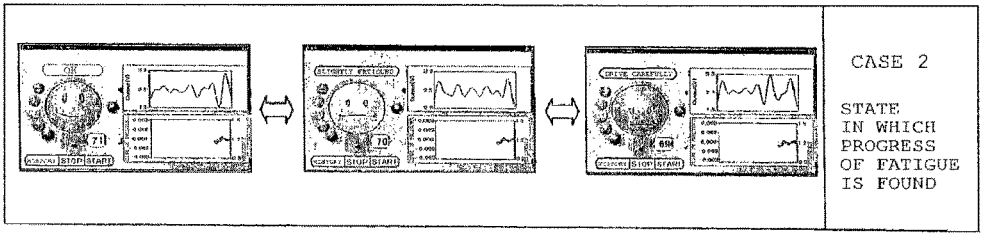
Figure 12C:
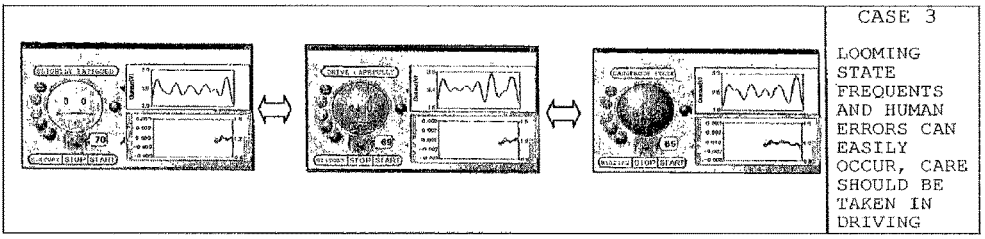
Figure 12D:
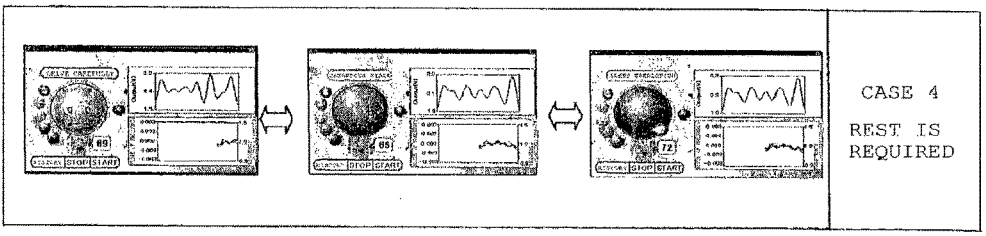
Figure 12E:
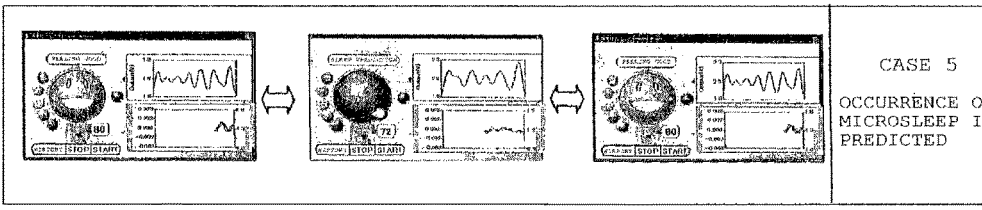

The example in FIG. 11E shows a graph drawn within a range of the homeostatic function stage 1, which is a highly active state with little fluctuation. This indicates a state in which a person's highly focused state continues due to over-tension, and fluctuation becomes less and the air pack does not detect fluctuation, that is, a state with over-tension caused by activation of the brain. However, a sharp protruding line occurs in which the homeostatic function level drops over two stages all at once in several to several tens of seconds (in this example, three stages from the homeostatic function stage 1 to the homeostatic function stage 4) around 25 minutes, 40 minutes, and 47 minutes in the graph in FIG. 11E and returns all at once. This sharp protruding line is a reaction to the continuation of the over-tension and leads to progress of fatigue in the over-tensed state. In this experiment, after the sharp protruding line occurs several times, micro-sleep occurs in the driver. Since this is considered to be a marked drop in the homeostatic function of a biological body, this sharp protruding line is defined to indicate sleep prediction which is a signal immediately before micro-sleep. For more accurate determination of the sleep prediction signal, not only the rapid drop of the homeostatic function level but also predominance of an absolute value acquired by the sign of a rectangular wave and the zero-crossing method is preferably considered as will be described later. Thus, when such a protruding line occurs several times, this is determined to be a sleep prediction signal and a state requiring a rest as soon as possible.

As described above, according to this embodiment, the homeostatic function level can be visually and clearly captured. That is, if the driver visually captures the graph in FIG. 11A, for example, the driver understands that he/she is in a state in which smooth driving is possible, while if he/she visually captures the graph in FIG. 11C, he/she can understand that he/she is in a state in which he/she should have a rest relatively soon while paying attention to driving. If the protruding line as in FIG. 11E is visually recognized, since it is likely to be a sleep prediction signal, the driver can understand that he/she should have a rest relatively early. That is, the display by the graph on the display means 65 can stimulate and activate the brain of the driver, induce the driver to the awakening direction and promote a rest at an earlier stage when the driver looks at the display and grasps his/her own state, though only for a short time.

In this embodiment, when the driver looks at the graph displayed on the display means 65, the driver can easily grasp his/her own state, which promotes stimulation to the brain, and determining means (determining step) 63 for automatically determining whether a rest is needed or not or whether a sleep prediction signal has emerged can also be incorporated.

The determining means 63 monitors movement of a base line in the graph of the above-described homeostatic function stages. If the base line moves into a range of the homeostatic function stages 3 to 5 as in FIGS. 11C and 11D and enters a state in which recovery from fatigue is not found, an alarm by sound or vibration can be emitted. In this embodiment, the brain is activated and induced to the awakening direction by visually grasping the homeostatic function stage, but by including a so-called monitoring system by using the determining means 63, an alarm such as sound and vibration can be used at the same time. Particularly, by providing abnormal state determining means that if a sleep prediction signal as in FIG. 11E emerges three times, for example, it is determined to be an abnormal state, and a larger alarm sound or the like is emitted in the configuration, contribution can be made to more reliable suppression of drowsy driving.

Here, the above-described output means 62 displays the homeostatic function level of a person by a line graph in a time series, but the display means 65 can be configured to be provided with a separate screen output means 621 which outputs display different from the above-described line graph on a different screen. FIGS. 12A to 12E show images outputted to the display means 65 by this separate screen output means 621.

Figure 13:
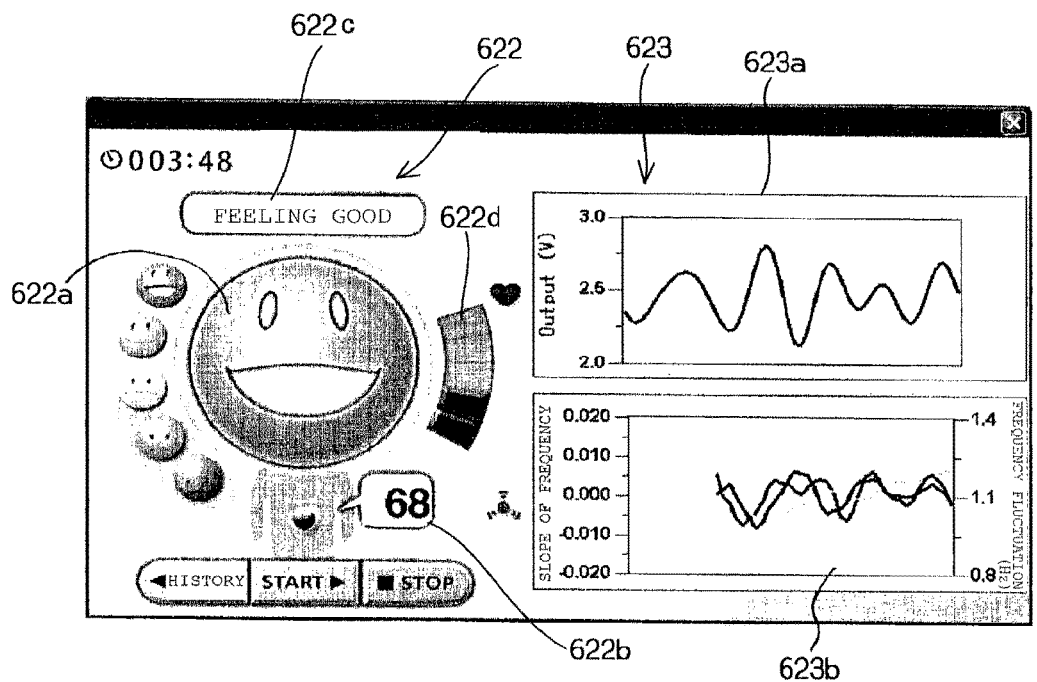
FIG. 13 is an enlarged view showing an image outputted on the display means by the separate screen output means.
Figure 15A:
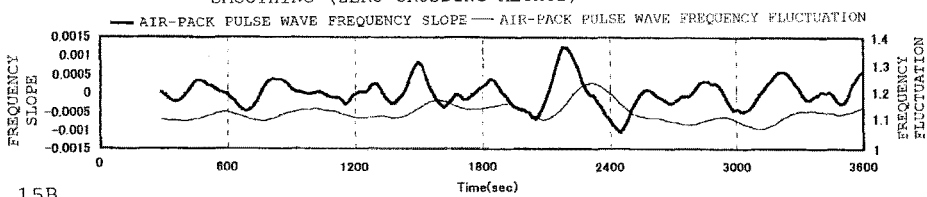
FIGS. 15A to 15G are diagrams showing analysis results of the biological body state estimation device in a test example 2.
Figure 15B:
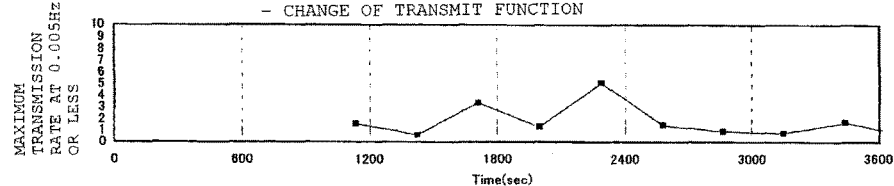
Figure 15C:
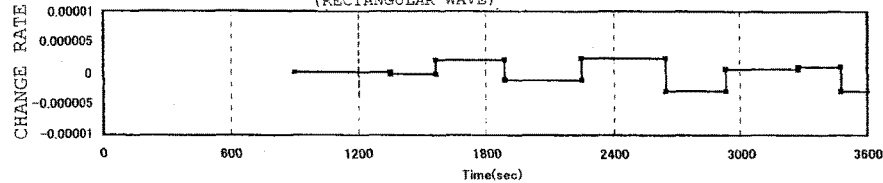
Figure 15D:
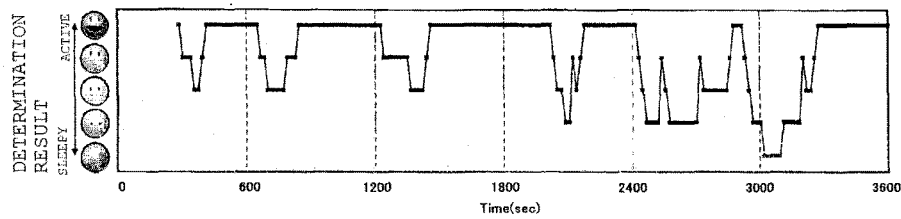
Figure 15E:
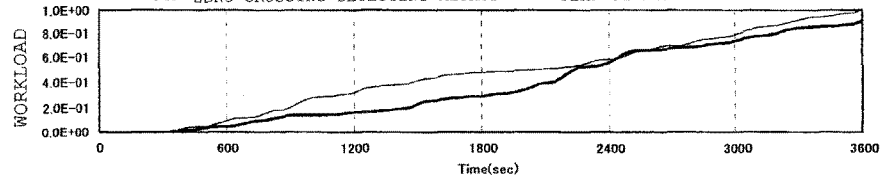
Figure 15F:
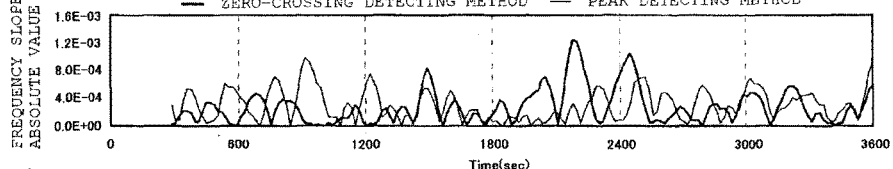
Figure 15G:
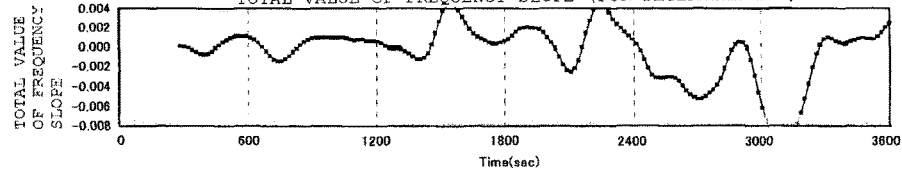
Figure 16A:
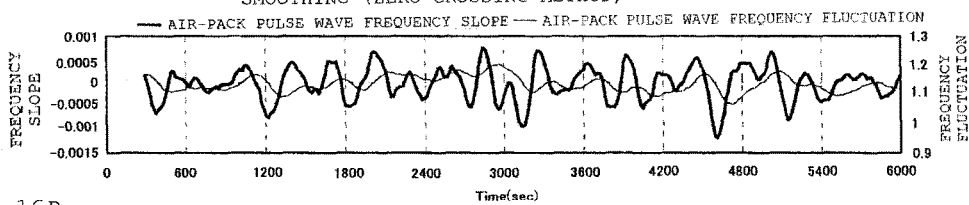
FIGS. 16A to 16G are diagrams showing analysis results of the biological body state estimation device in the test example 2.
Figure 16B:
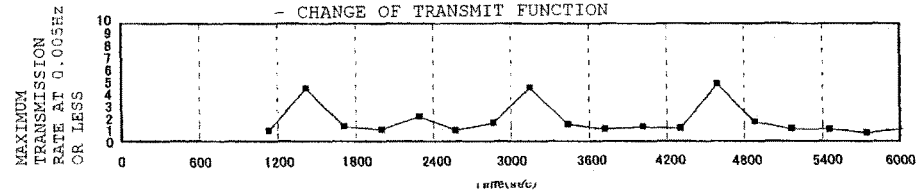
Figure 16C:
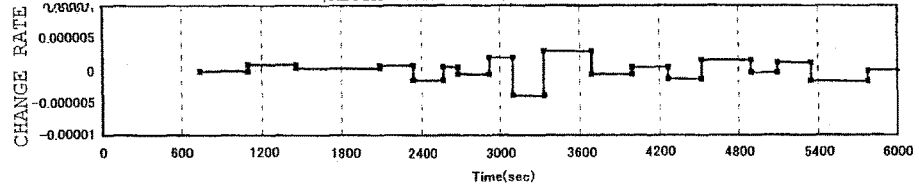
Figure 16D:
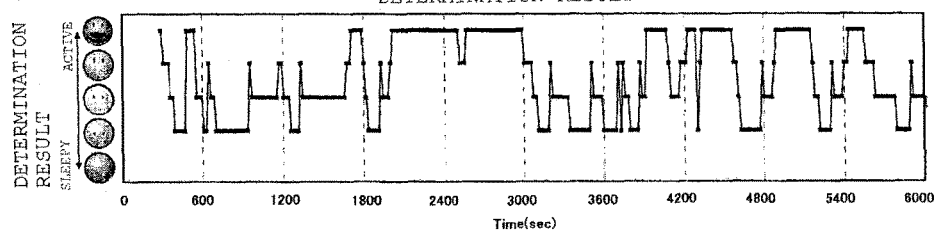
Figure 16E:
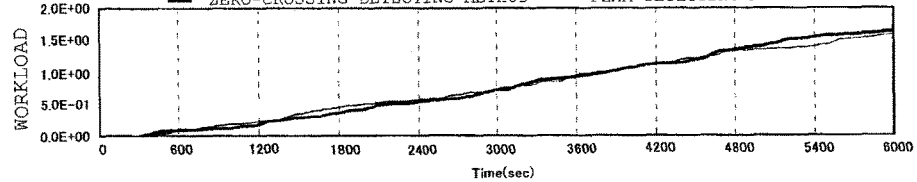
Figure 16F:
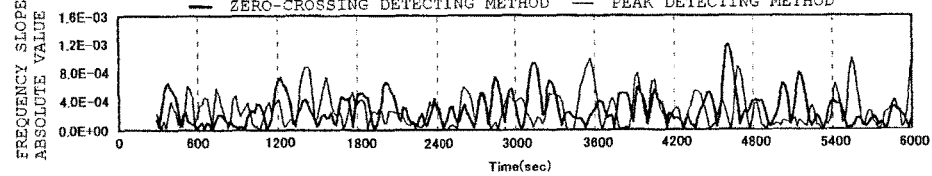
Figure 16G:
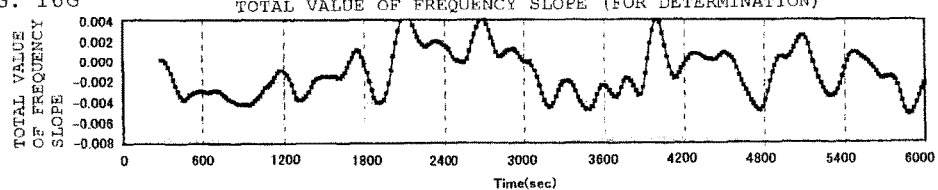
Figure 17A:
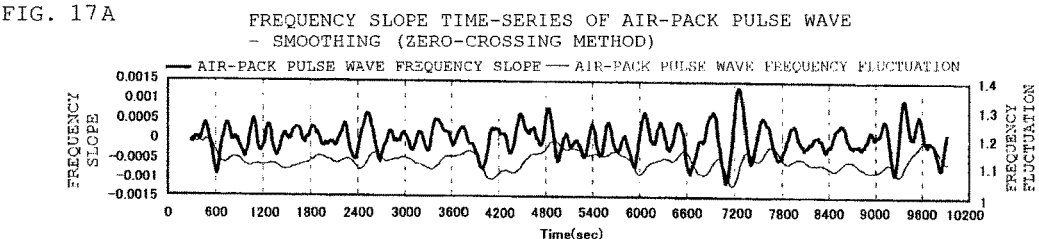
FIGS. 17A to 17G are diagrams showing analysis results of the biological body state estimation device in the test example 2.
Figure 17B:
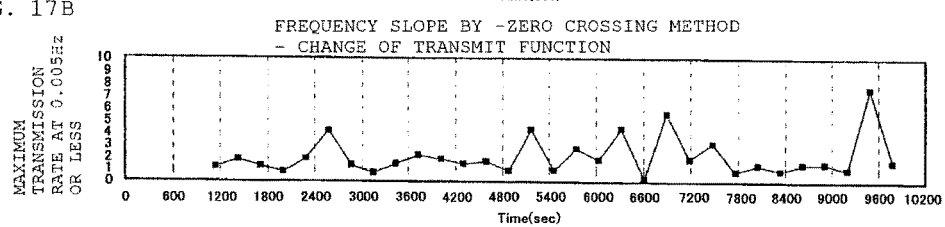
Figure 17C:
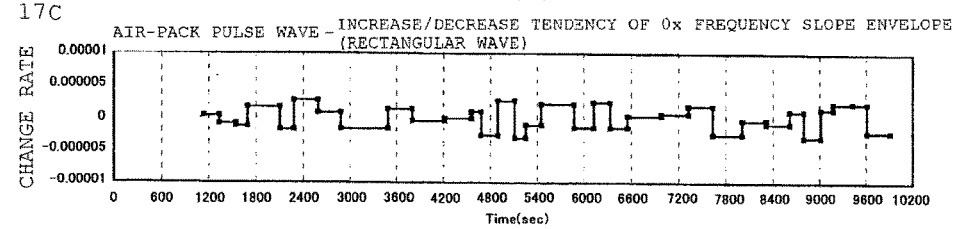
Figure 17D:
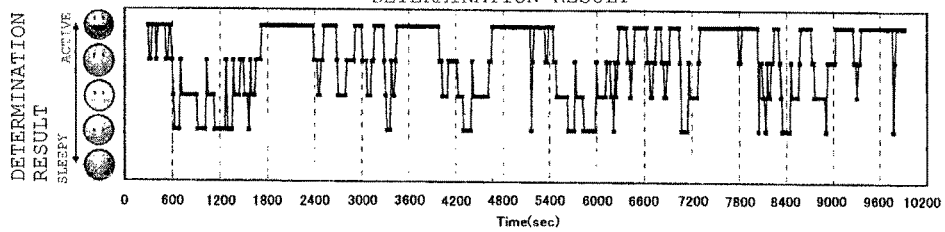
Figure 17E:
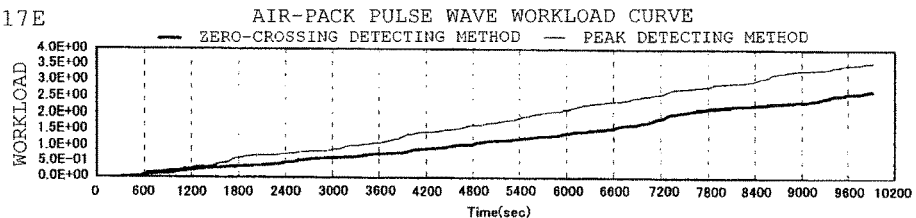
Figure 17F:
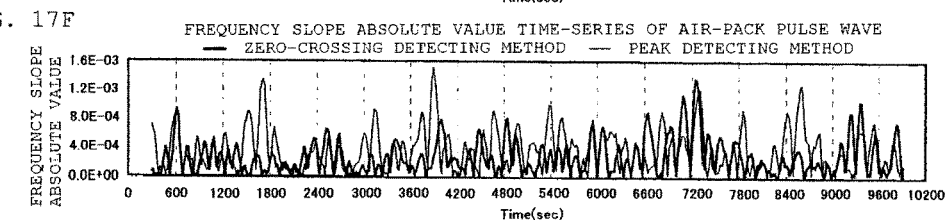
Figure 17G:
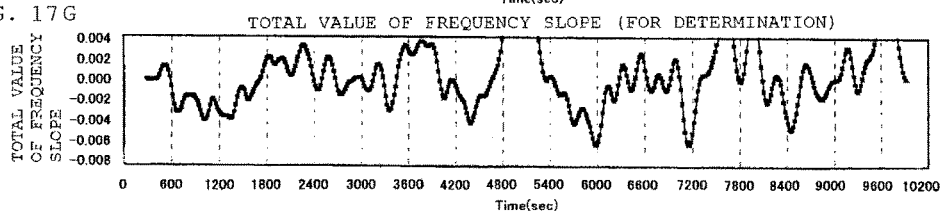
Figure 18A:
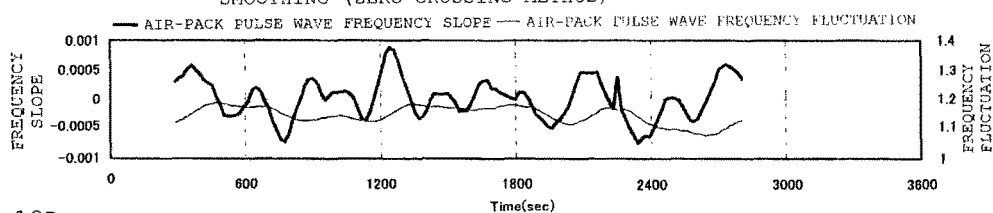
FIGS. 18A to 18G are diagrams showing analysis results of the biological body state estimation device in the test example 2.
Figure 18B:
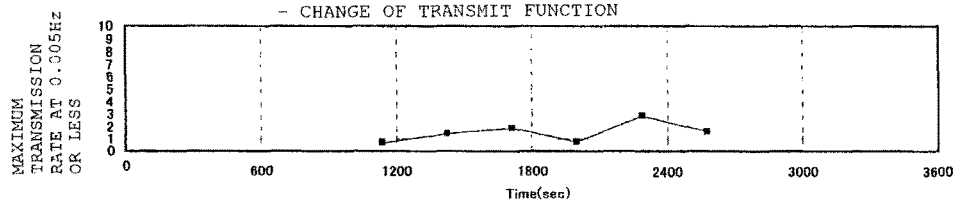
Figure 18C:
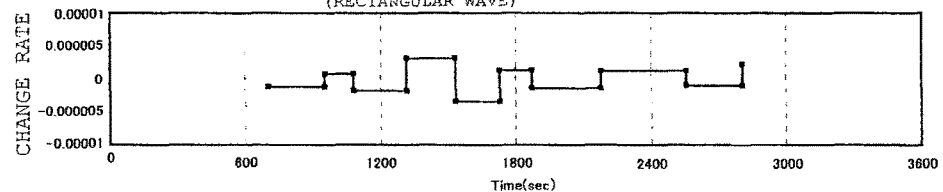
Figure 18D:
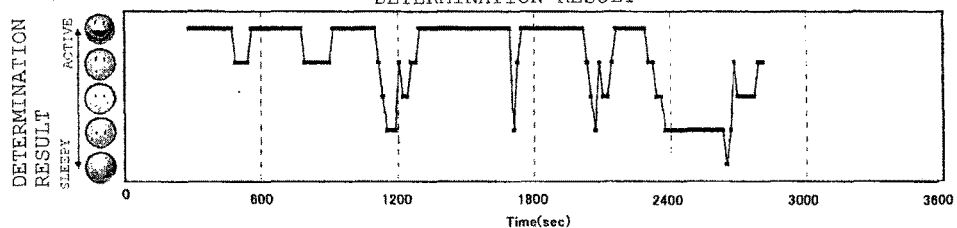
Figure 18E:
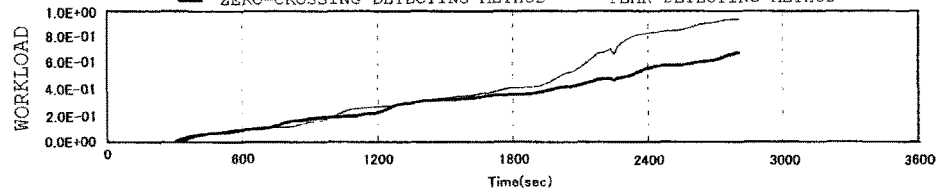
Figure 18F:
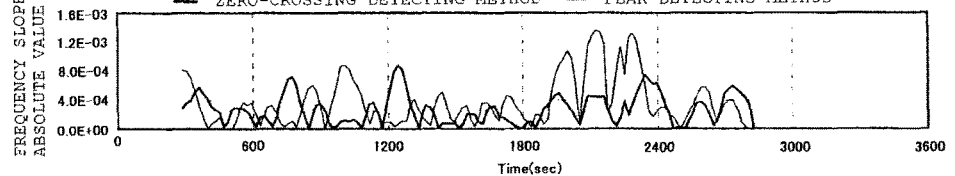
Figure 18G:
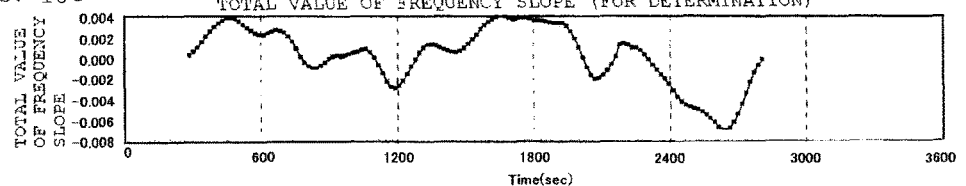
Figure 19A:
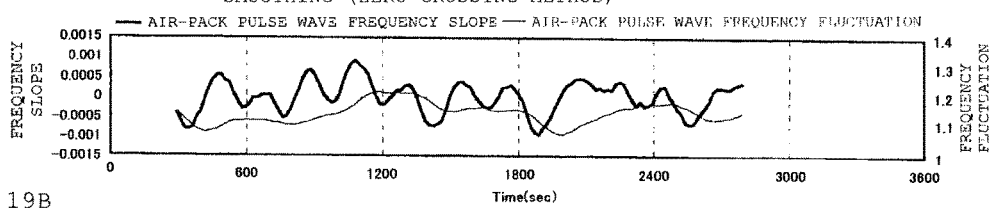
FIGS. 19A to 19G are diagrams showing analysis results of the biological body state estimation device in the test example 2.
Figure 19B:
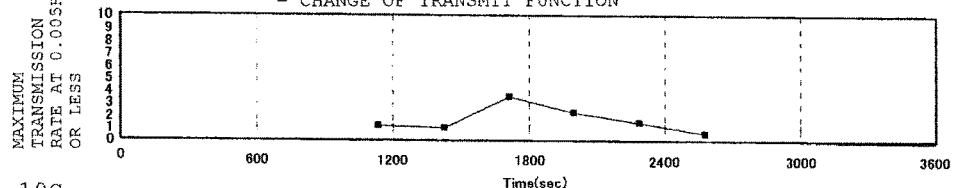
Figure 19C:
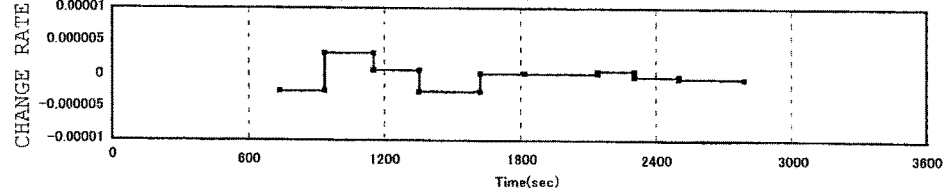
Figure 19D:
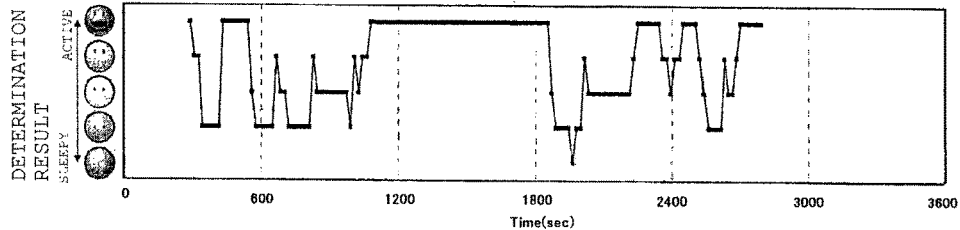
Figure 19E:
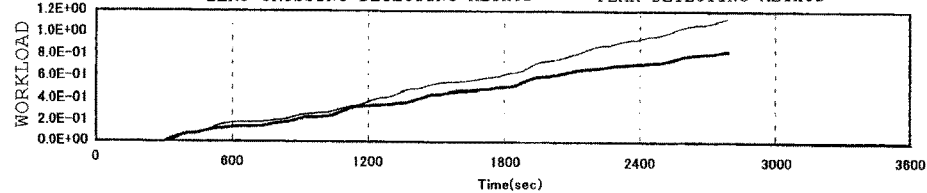
Figure 19F:
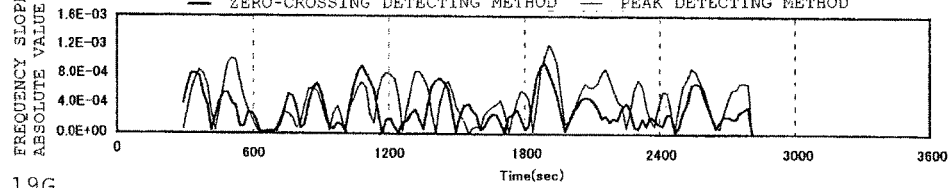
Figure 19G:
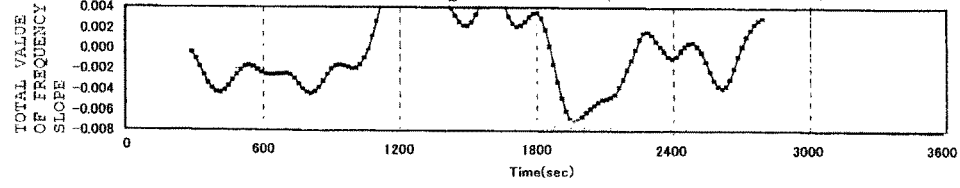
Figure 20A:
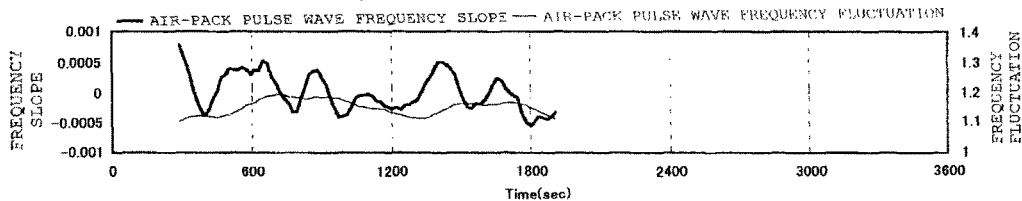
FIGS. 20A to 20G are diagrams showing analysis results of the biological body state estimation device in the test example 2.
Figure 20B:
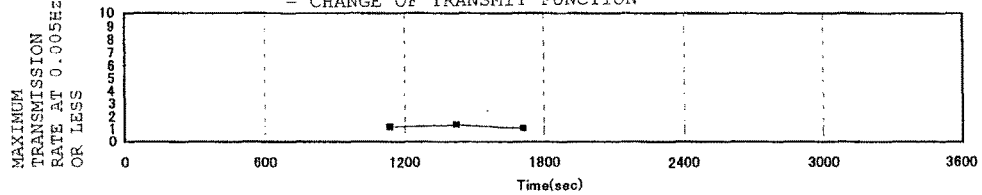
Figure 20C:
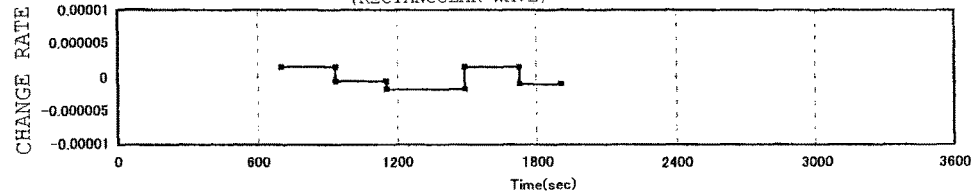
Figure 20D:
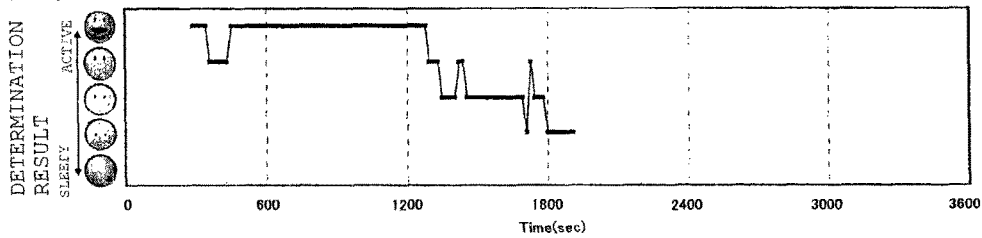
Figure 20E:
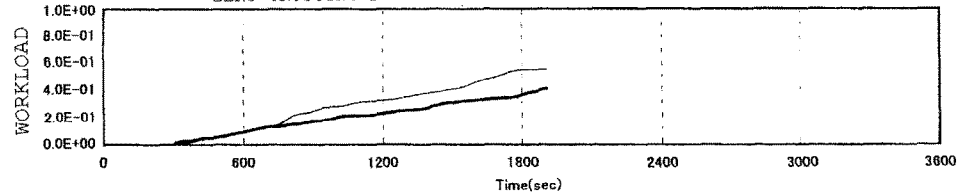
Figure 20F:
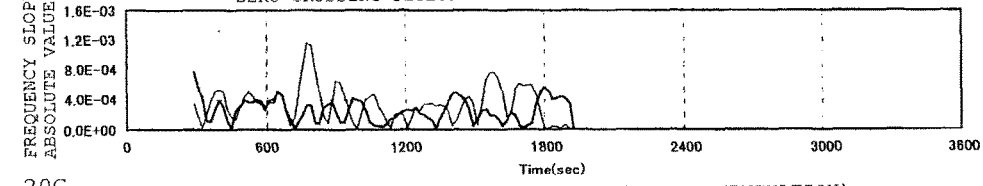
Figure 20G:
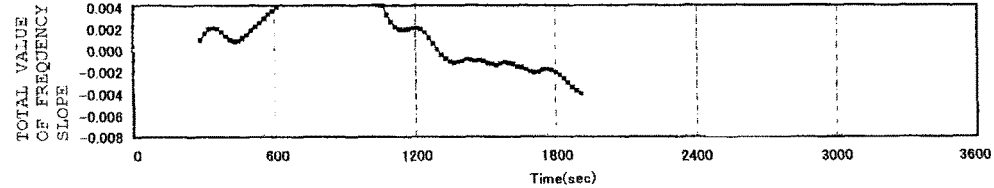
Figure 21A:
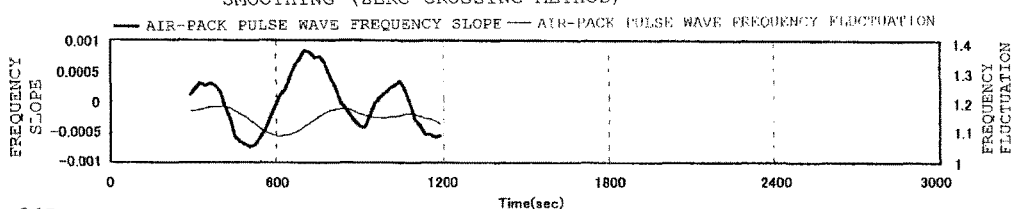
FIGS. 21A to 21G are diagrams showing analysis results of the biological body state estimation device in the test example 2.
Figure 21B:
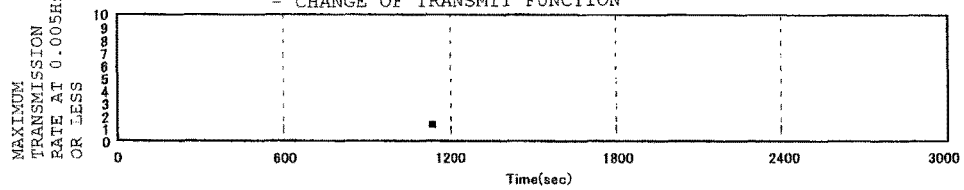
Figure 21C:
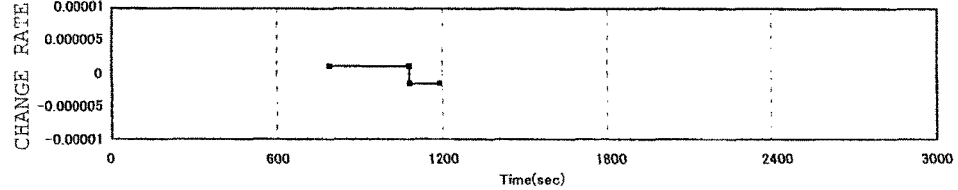
Figure 21D:
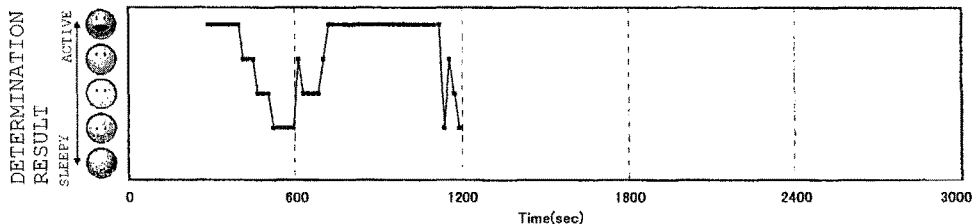
Figure 21E:
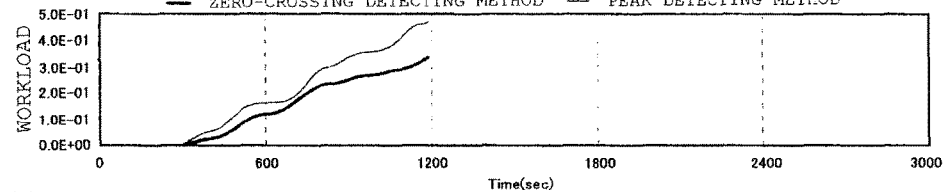
Figure 21F:
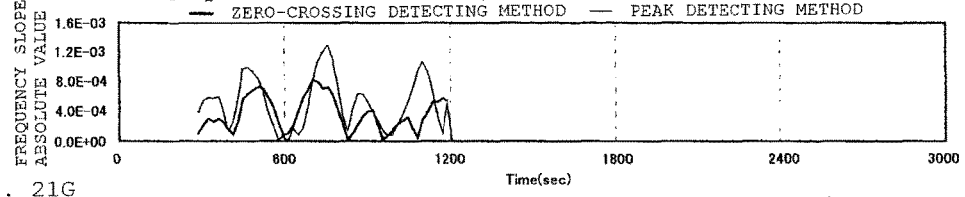
Figure 21G:
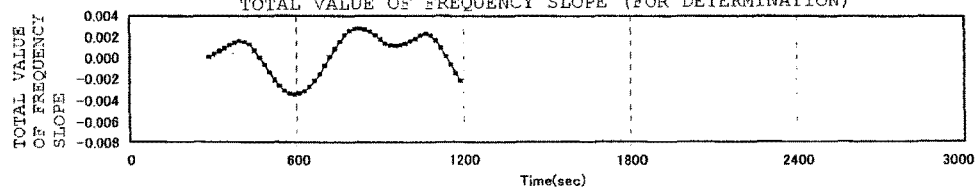
Figure 22A:
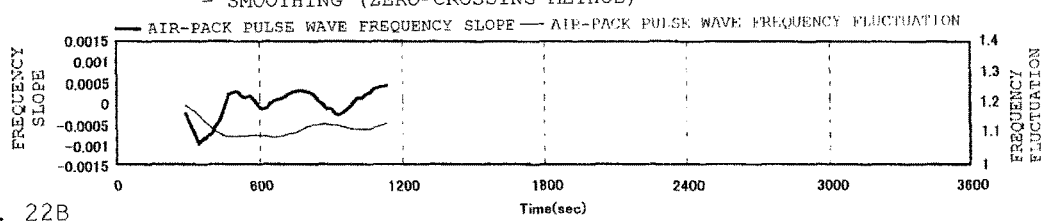
FIGS. 22A to 22G are diagrams showing analysis results of the biological body state estimation device in the test example 2.
Figure 22B:
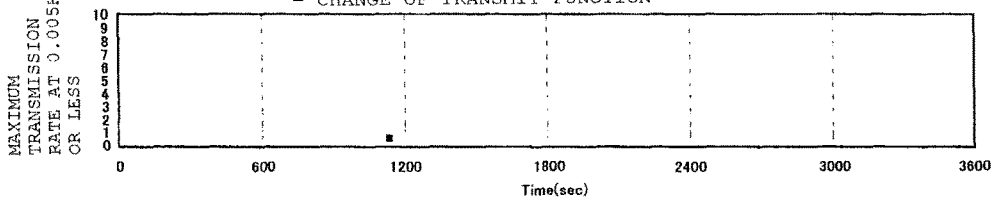
Figure 22C:
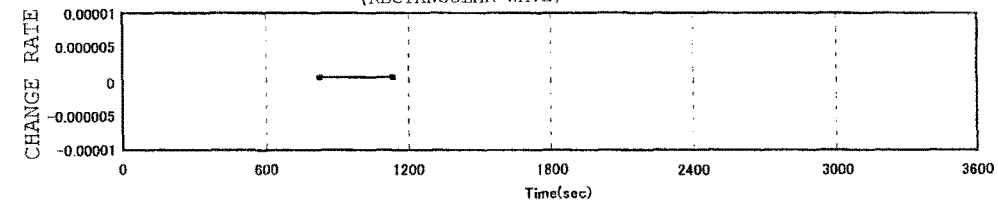
Figure 22D:
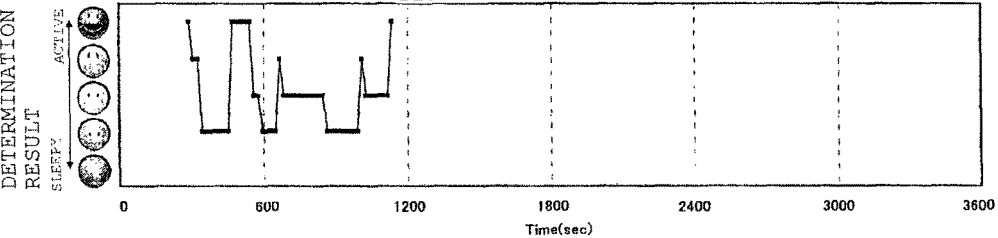
Figure 22E:
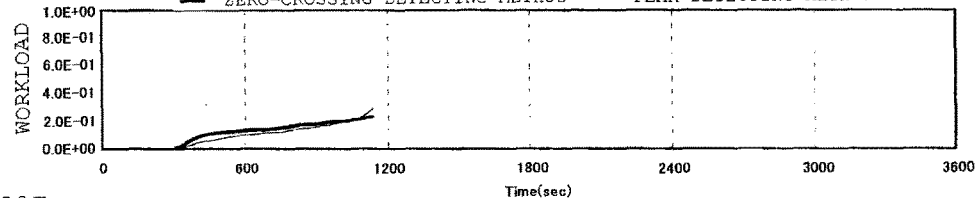
Figure 22F:
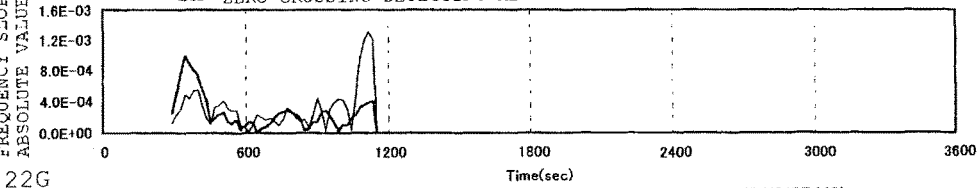
Figure 22G:
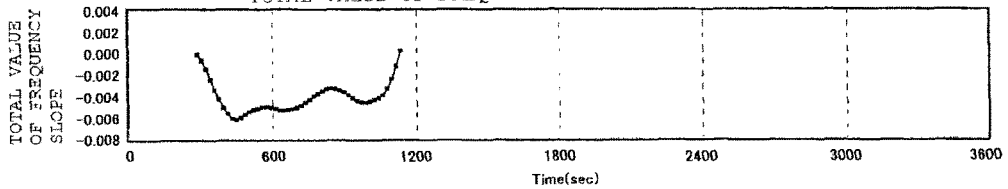
Figure 23A:
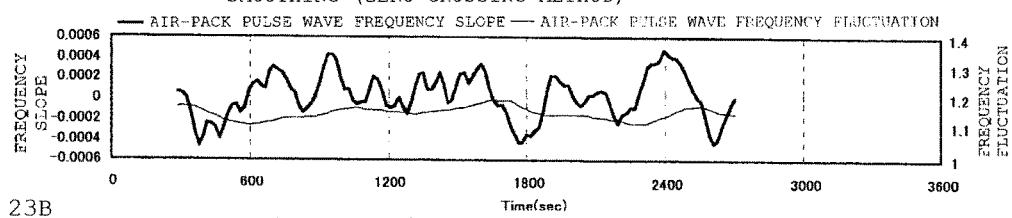
FIGS. 23A to 23G are diagrams showing analysis results of the biological body state estimation device in the test example 2.
Figure 23B:
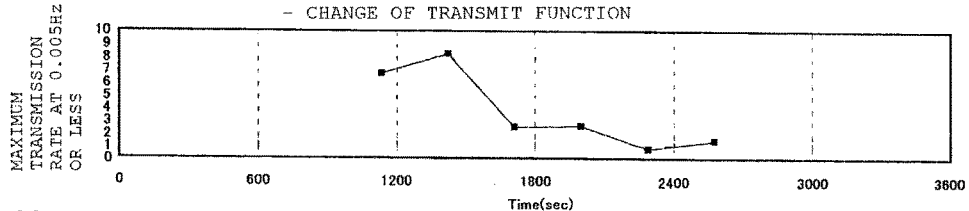
Figure 23C:
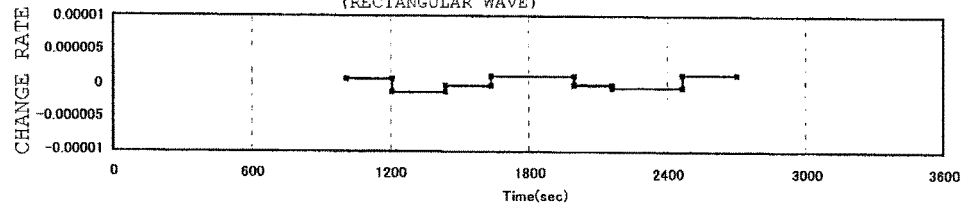
Figure 23D:
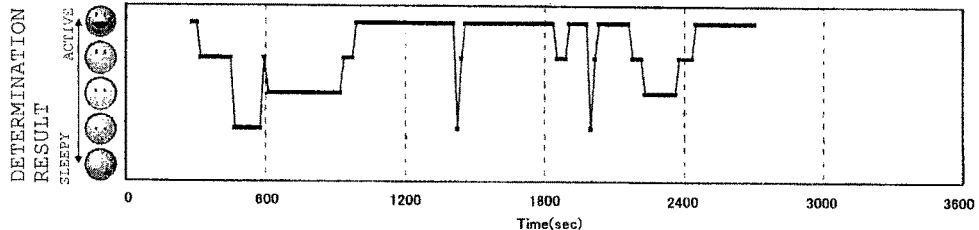
Figure 23E:
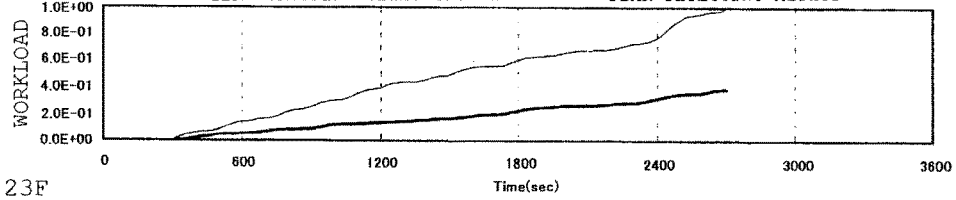
Figure 23F:
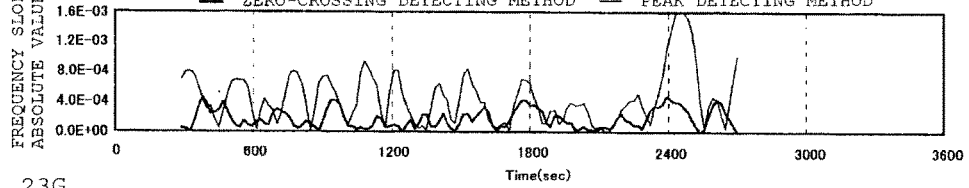
Figure 23G:
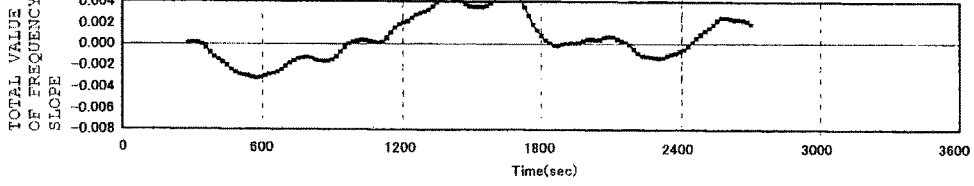
Figure 24A:
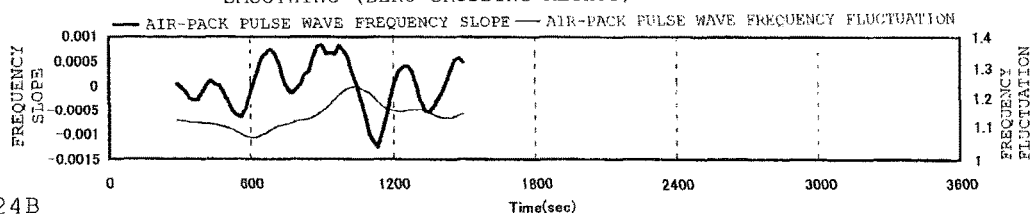
FIGS. 24A to 24G are diagrams showing analysis results of the biological body state estimation device in the test example 2.
Figure 24B:
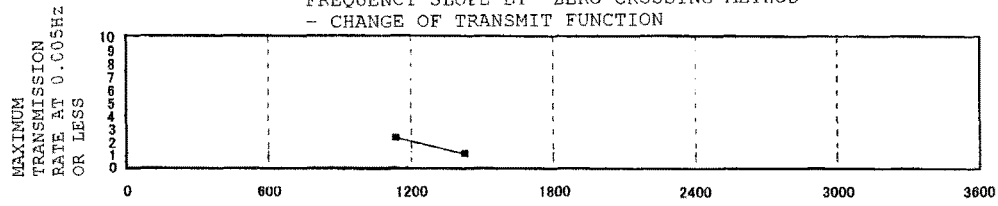
Figure 24C:
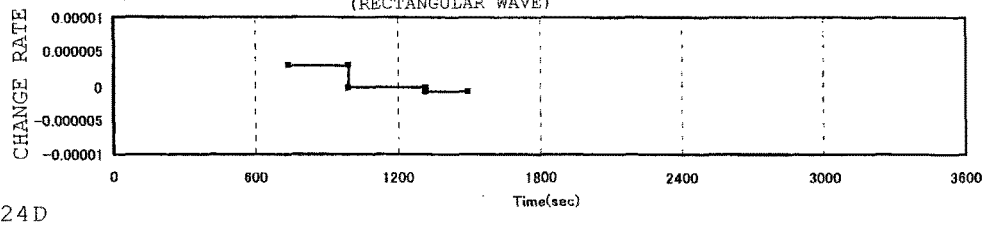
Figure 24D:
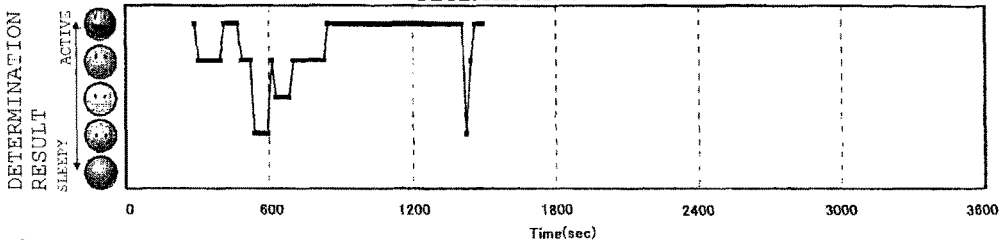
Figure 24E:
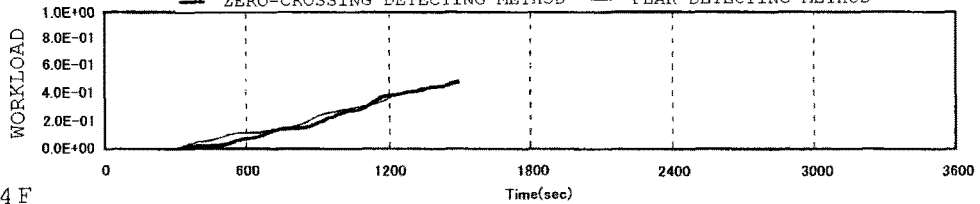
Figure 24F:
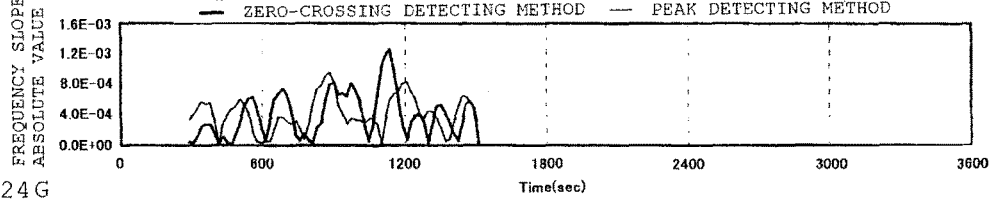
Figure 24G:
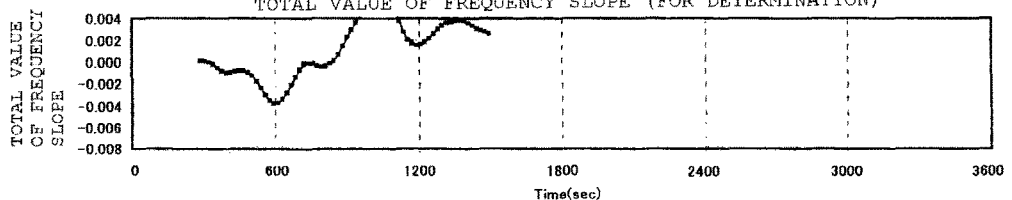
Figure 25A:
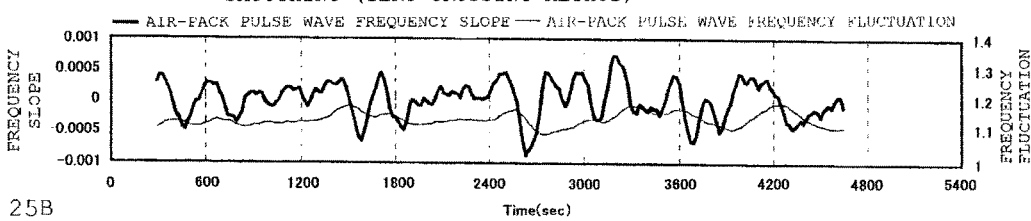
FIGS. 25A to 25G are diagrams showing analysis results of the biological body state estimation device in the test example 2.
Figure 25B:
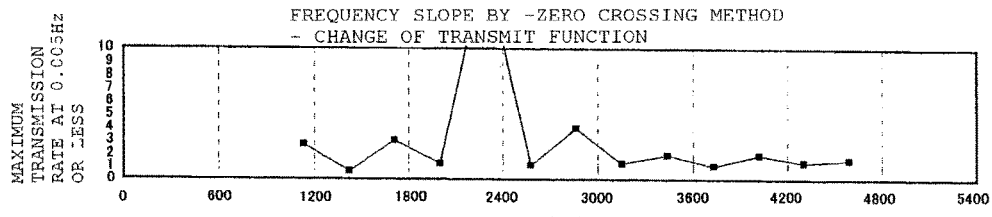
Figure 25C:
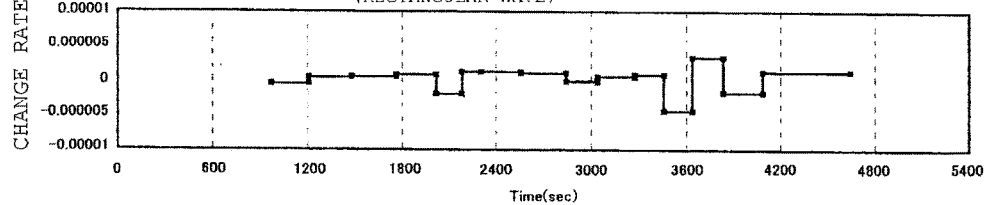
Figure 25D:
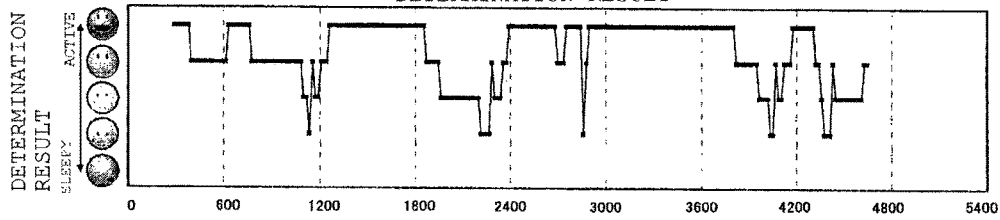
Figure 25E:
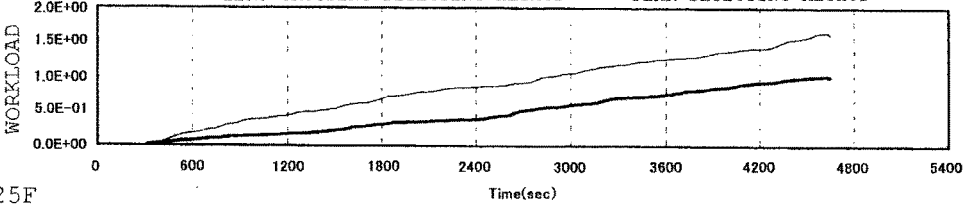
Figure 25F:
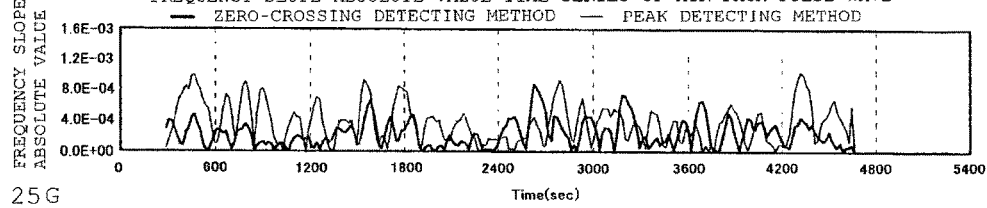
Figure 25G:
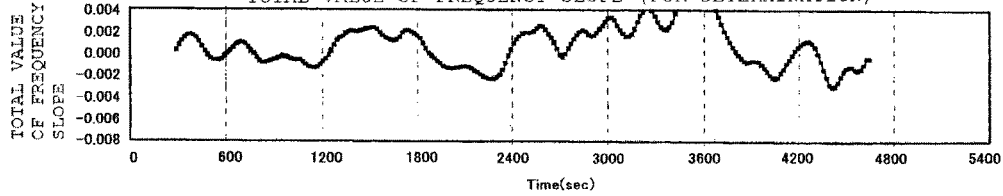
Figure 26A:
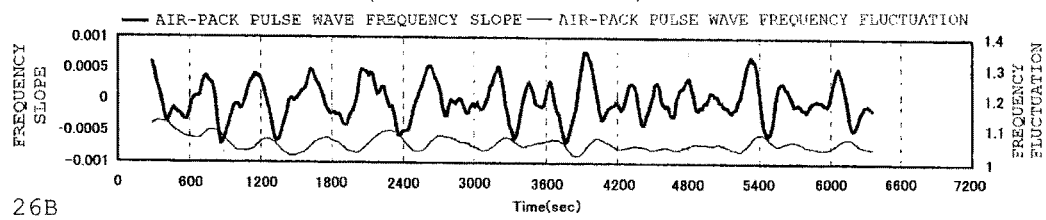
FIGS. 26A to 26G are diagrams showing analysis results of the biological body state estimation device in the test example 2.
Figure 26B:
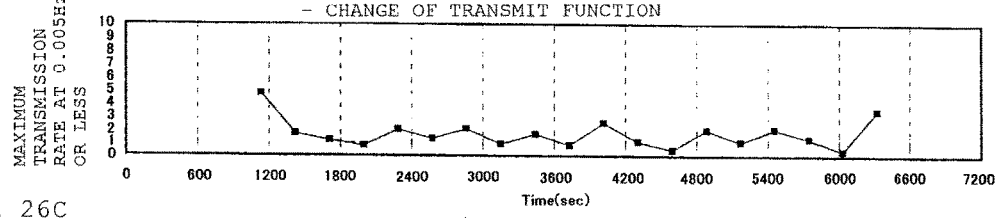
Figure 26C:
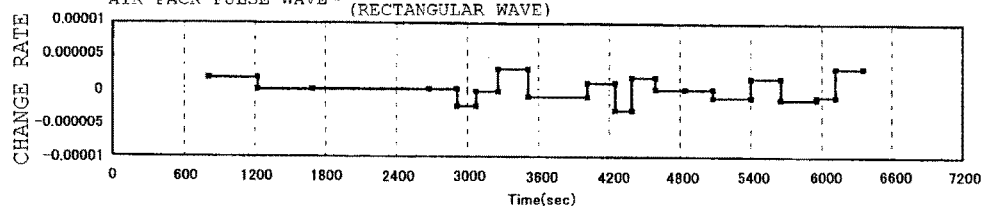
Figure 26D:
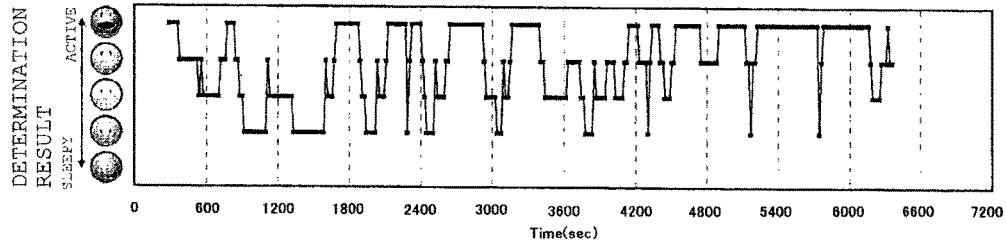
Figure 26E:
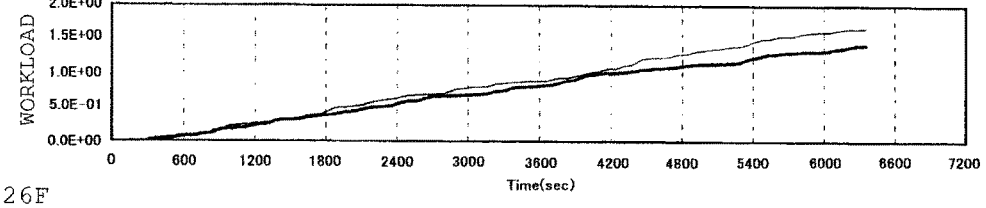
Figure 26F:
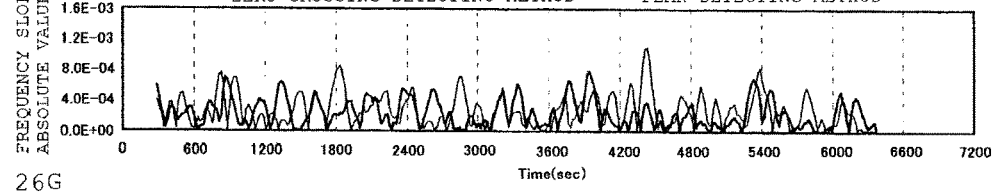
Figure 26G:
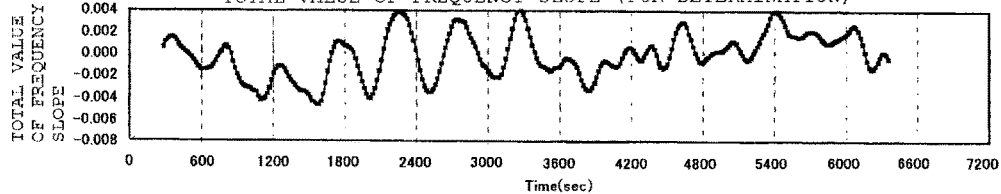
Figure 27A:
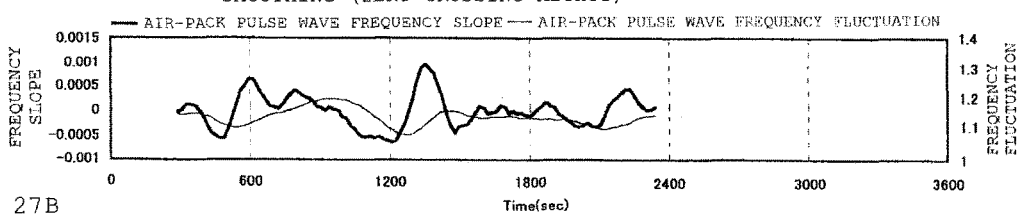
FIGS. 27A to 27G are diagrams showing analysis results of the biological body state estimation device in the test example 2.
Figure 27B:
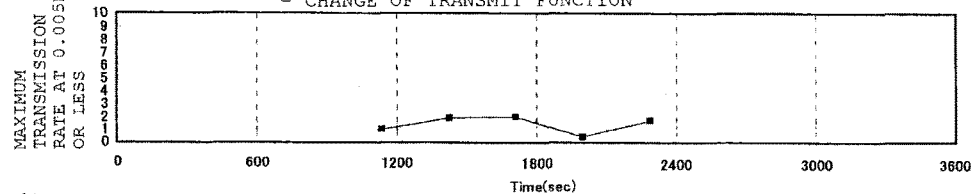
Figure 27C:
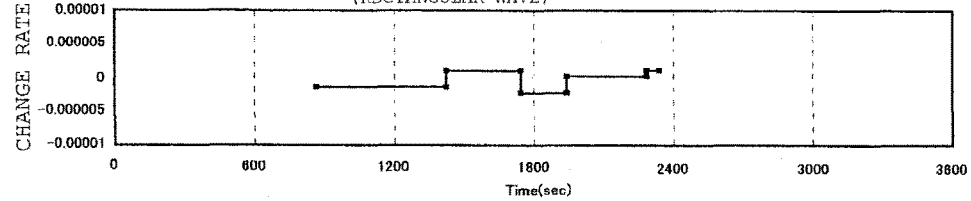
Figure 27D:
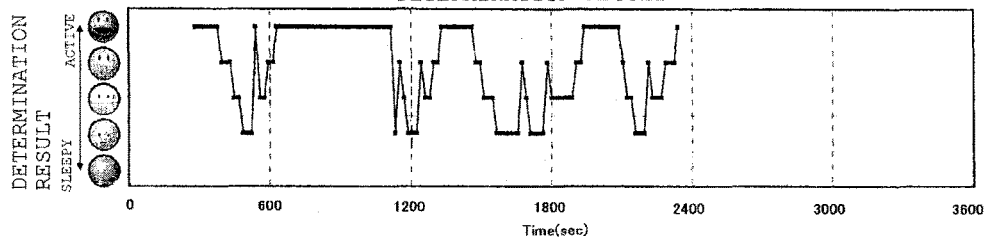
Figure 27E:
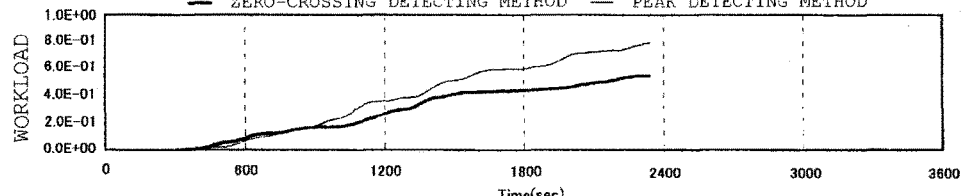
Figure 27F:
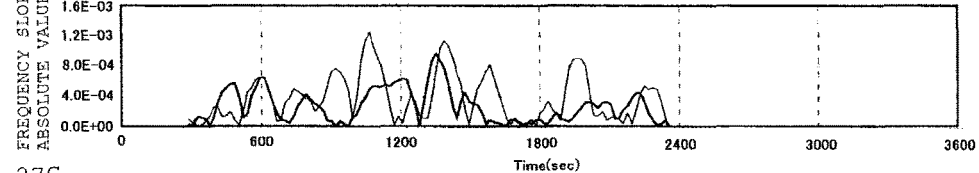
Figure 27G:
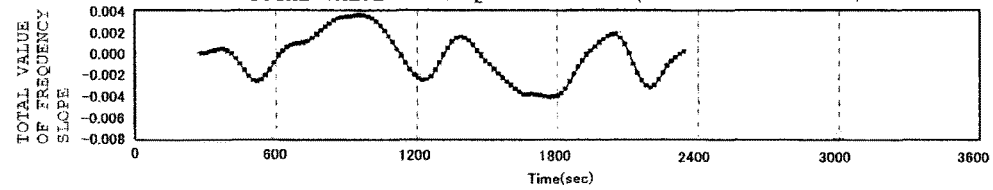
Figure 28A:
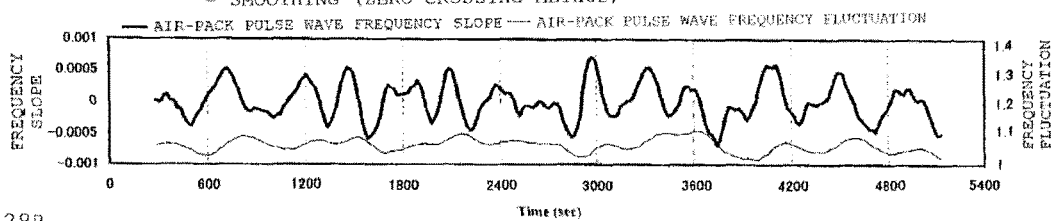
FIGS. 28A to 28G are diagrams showing analysis results of the biological body state estimation device in the test example 2.
Figure 28B:
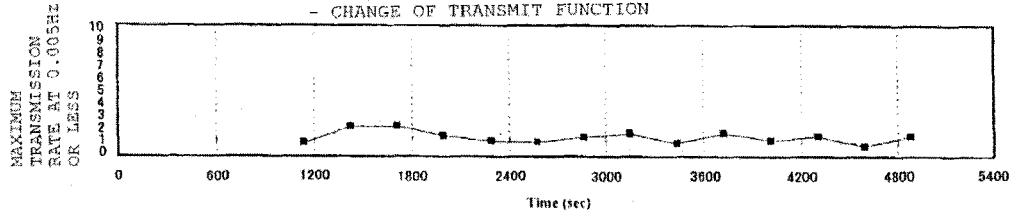
Figure 28C:
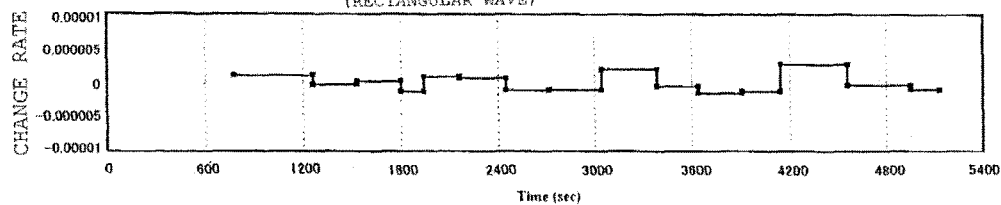
Figure 28D:
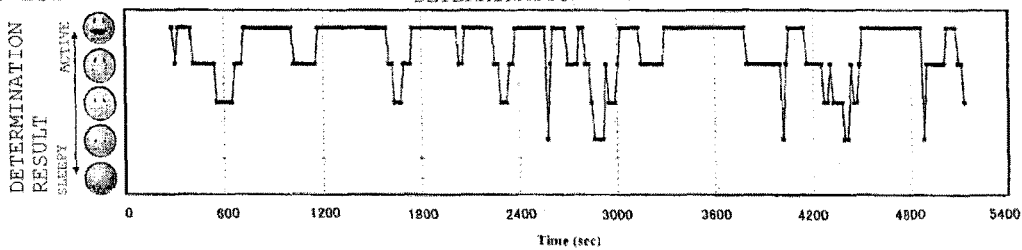
Figure 28E:
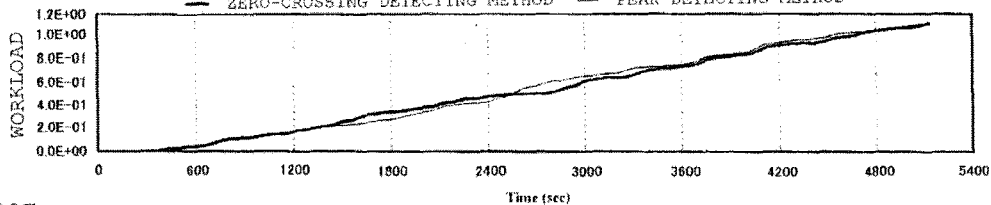
Figure 28F:
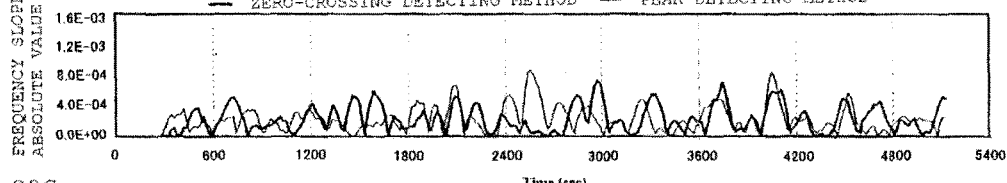
Figure 28G:
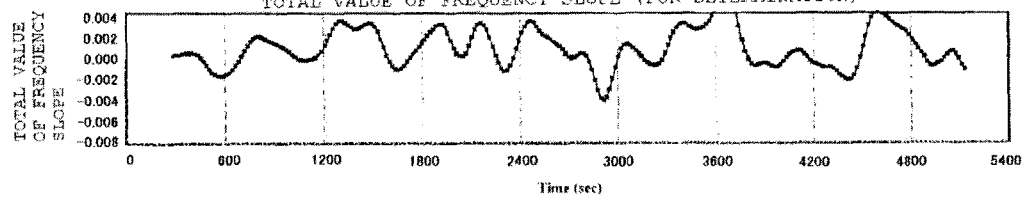
Figure 29A:
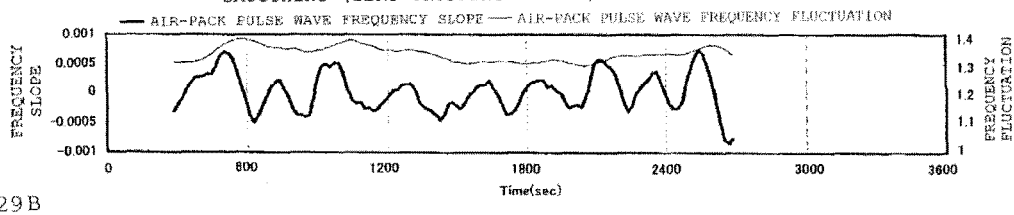
FIGS. 29A to 29G are diagrams showing analysis results of the biological body state estimation device in the test example 2.
Figure 29B:
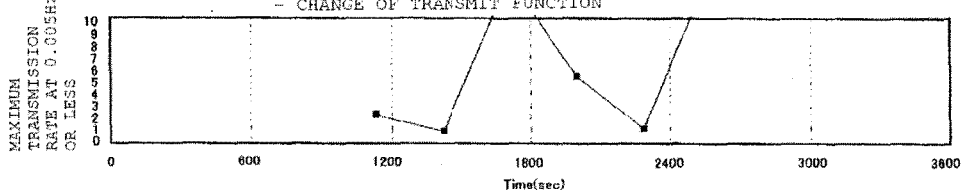
Figure 29C:
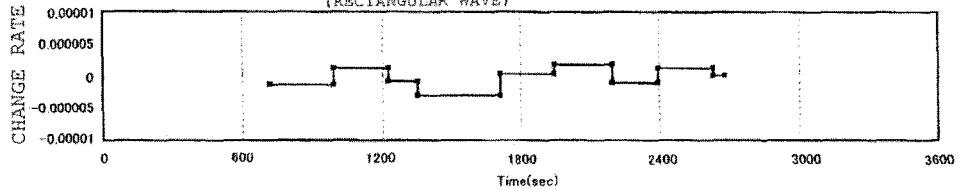
Figure 29D:
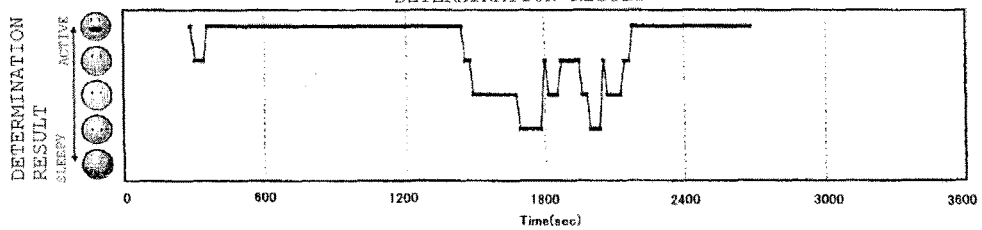
Figure 29E:
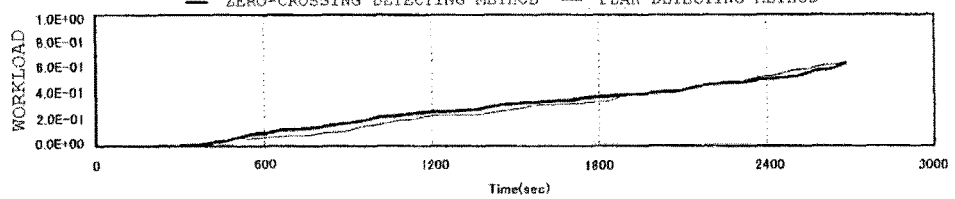
Figure 29F:
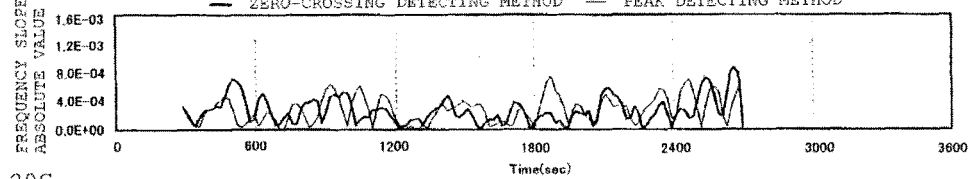
Figure 29G:
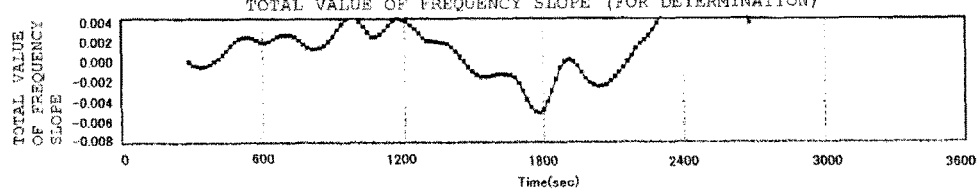
Figure 30A:
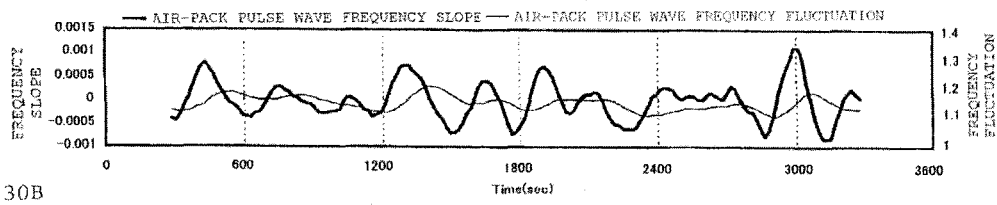
FIGS. 30A to 30G are diagrams showing analysis results of the biological body state estimation device in the test example 2.
Figure 30B:
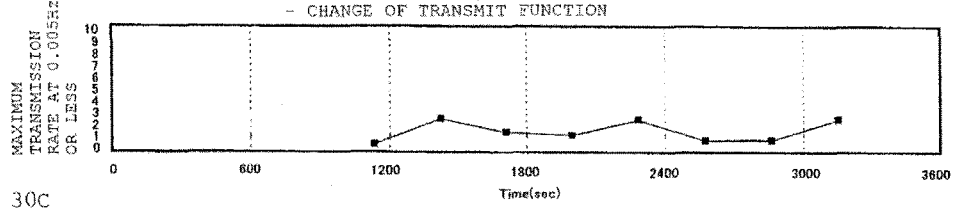
Figure 30C:
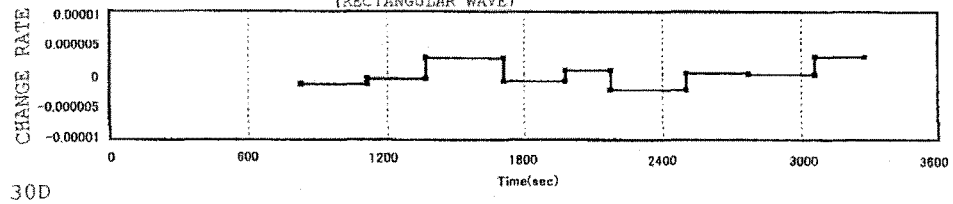
Figure 30D:
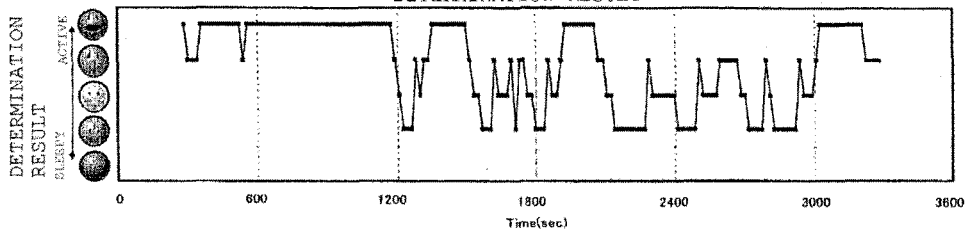
Figure 30E:
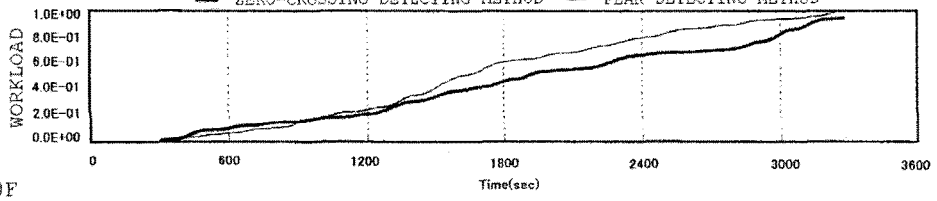
Figure 30F:
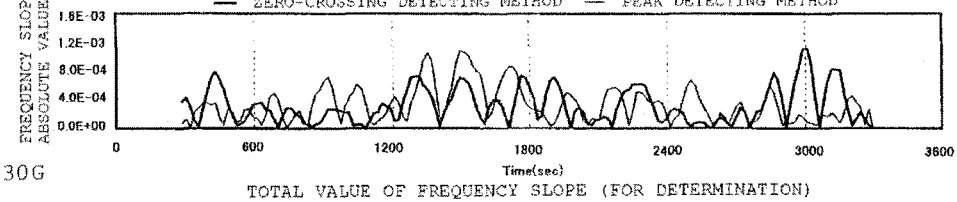
Figure 30G:
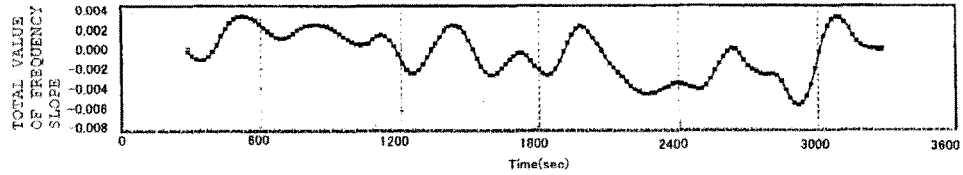

A screen displayed by the separate screen output means 621 displays, as a typical example shown in an enlarged manner in FIG. 13, a first image portion 622 showing a state of a face of an androgynous person (the same face as that in an image diagram of the face on the vertical axis on the line graph) in an image corresponding to the homeostatic function stages 1 to 5 and a second image portion 623 including time-series graphs in this embodiment. The first image portion 622 has a face image display portion 622a at the center, a heartbeat display portion 622b below that, a character display portion 622c above that, and a sleep prediction signal display portion 622d displayed on the right side. In the face image display portion 622a, the separate screen output means 621 displays an image of a face corresponding to one of the homeostatic function stages in accordance with the homeostatic function stage acquired by the homeostatic function level computing means 61. In the character display portion 622c, characters set by the separate screen output means 621 in accordance with each of the homeostatic function stages, that is, "feeling good", "OK", "ordinary state", "drive carefully", "fatigued state" and the like, for example, are displayed. The sleep prediction signal display portion 622d has five display lamps, and if the sleep prediction signal as shown in FIG. 11E occurs, the number of occurrences is indicated by lighting of the display lamps. As a result, a person can become aware of timing when a rest is required by looking at lighting of the display lamps.

On the second image portion 623, a graph of a time-series waveform of a signal of pressure fluctuation (air-pack signal) caused by movement of the aorta on the back part detected by the biological signal measuring means 1 is displayed on the upper display portion 623a, and a graph of a time-series waveform of a slope of the frequency is displayed on the lower display portion 623b.

Each of the first image portion 622 and the second image portion 623 displayed by the separate screen output means 621 is not limited to these displays, and when a driver visually recognizes particularly the face image display portion 622a, the character display portion 622c, and the sleep prediction signal display portion 622d of the first image portion 622, the driver can easily grasp the current situation. Since the display of the first image portion 622 only shows a state at a given moment, the driver can grasp a change in his/her state over time by looking at the screen and predict a future change in his/her state, thereby becoming strongly aware of necessity to rest. Therefore, a screen of a line graph as shown in FIG. 11 is preferably displayed so that the driver can visually recognize it.

Whether the screen of the line graph in FIG. 11 is displayed or the screen with the first image portion 622 and the second image portion 623 in FIG. 12 is displayed at start can be arbitrarily set. This embodiment is set such that a screen with the first image portion 622 and the second image portion 623 shown in FIG. 12 and FIG. 13 is displayed as an initial screen, and by pressing a "START" button, measurement is started, and computing by the homeostatic function level computing means 61 is started. It is set so that, pressing a "history" button will display the screen with the line graph in FIG. 11. That is, a change at the moment is displayed by the screen composed of the first image portion 622 and the second image portion 623 shown in FIG. 12 and FIG. 13, and a change in a time series including a past history is displayed by a screen of the line graph shown in FIG. 11. Moreover, in this embodiment, in order to display the screen with the line graph in FIG. 11 during driving, each of the "START" button and the "history" button need to be operated, and that gives an advantage that activation of the brain is promoted by movement of fingers. Moreover, according to this embodiment, the screen with the line graph in FIG. 11, the first image portion 622 (particularly the portion of the heartbeat) and the second image portion 623 in FIG. 12, that is, three screens in total are visually recognized, but the driver trying to comprehensively grasp his/her own state from the three screens by looking at the three screens also leads to activation of the brain. If the number of screens is smaller than 3, the brain activation effect is lower, while if it is larger than 3, it is too complicated. It is needless to say that the "START" and "history" buttons are preferably provided close to a steering wheel so that the operation thereof does not disturb driving.

Subsequently, a specific computing method set in the homeostatic function level computing means (homeostatic function level computing step) 61 will be described. That is, the homeostatic function level computing means 61 includes frequency computing means (frequency computing step) 611, frequency slope time-series analyzing and computing means (frequency slope time-series analyzing and computing step) 612, frequency fluctuation time-series analyzing and computing means (frequency fluctuation time-series analyzing and computing step) 613, differentiating means (differentiating step) 614, integrating means (integrating step) 615, rectangular wave calculating means (rectangular wave calculating step) 616, describing function calculating means (describing function calculating step) 617, absolute value processing means (absolute value processing step) 618, and homeostatic function stage calculating means (homeostatic function stage calculating step) 619.

The frequency computing means 611 acquires a time-series waveform of a frequency in time-series data of an air pack signal obtained from the biological signal measuring means 1 (preferably an air-pack signal filter waveform of a predetermined frequency area subjected to filtering process as will be described later). There are two methods for obtaining this time-series waveform, the first one of which relates to HF used as an index of a parasympathetic nerve function, while the second one of which relates to LF/HF (LF is a frequency component at 0.05 to 0.20 Hz and HF is a frequency component at 0.20 to 0.35 Hz) used as an index of a sympathetic nerve function.

The first method is a method of acquiring a time-series waveform by using a maximum value (peak) through smoothing-differentiation of a time-series waveform of an air-pack signal (hereinafter referred to as a "peak detecting method"). The peak detecting method is basically a time-series waveform corresponding to the function of HF and a time-series waveform on which a waveform corresponding to a compensating function of LF/HF might be superimposed. The maximum value is acquired by the smoothing-differentiation by Savitzky and Golay, for example. Subsequently, the maximum value is obtained for every 5 seconds, for example, and reciprocals of time intervals between the maximum values of the time-series waveforms (peak side top portion of the waveform) included in the 5 seconds are acquired as individual frequencies f, and a mean value of the individual frequencies f in the 5 seconds is employed as the value of a frequency F in the 5 seconds (Step [1] in FIG. 9). Then, the time-series waveform of the frequency is acquired by plotting the frequencies F obtained for every 5 seconds (Step [2] in FIG. 9).

The second method is a method of acquiring a time-series waveform by using a point where a positive value changes to a negative value (hereinafter referred to as "zero-crossing point") in a time-series waveform of the air pack signal (hereinafter referred to as a "zero-crossing method"). This zero-crossing method captures a basic component of the frequency of a pulse wave and corresponds to LF/HF. In this method, first, the zero-crossing point is acquired and then, that is obtained for every 5 seconds, for example, and reciprocals of time intervals between the zero-crossing points of time-series waveforms included in the 5 seconds are acquired as individual frequencies f, and a mean value of the individual frequencies f in the 5 seconds is adopted as the value of the frequency F for the five seconds (Step [1] in FIG. 9). Then, the time-series waveform of the frequency is acquired by plotting the frequencies F obtained for every 5 seconds (Step [2] in FIG. 9).

The frequency time-series analyzing slope and computing means (frequency slope time-series analyzing and computing step) 612 sets a time window having a predetermined time width from the time-series waveform of the frequency of the air-pack pulse wave obtained from the frequency computing means 611 using peak detecting method or zero-crossing method, and obtains the slope of the frequency of the air-pack pulse wave for each time window by least-square method to output a time series wave thereof. The frequency slope time-series waveform obtained by the frequency slope time-series analyzing and computing means 612 is outputted as the waveform indicating fluctuation of a biological body capturing balance of occurrence between the sympathetic nerve and parasympathetic nerve. Specifically, first, a slope of a frequency in a certain time window Tw1 is obtained by least-square method to be plotted (Steps [3] and [5] in FIG. 9). Next, the next time window Tw2 is set in an overlapped time T1 (Step [6] in FIG. 9) and a slope of a frequency in this time window Tw2 is similarly obtained by least-square method to be plotted. This calculation (movement calculation) is repeated sequentially to output a slope time-series waveform of the frequency of the air-pack pulse wave as a frequency slope time-series waveform (Step [8] in FIG. 9). Incidentally, it is preferred that the time width of the time window Tw is set to 180 seconds, and it is preferred that the overlapped time T1 is set to 162 seconds. These values were selected as values at which a characteristic signal emerged with the best sensitivity from sleep experiments performed while changing the time width of the time window Tw and the overlapped time T1 variously, as shown in the above-described Patent Literature 3 (WO 2005/092193A1) of the present applicant.

Figure 9:
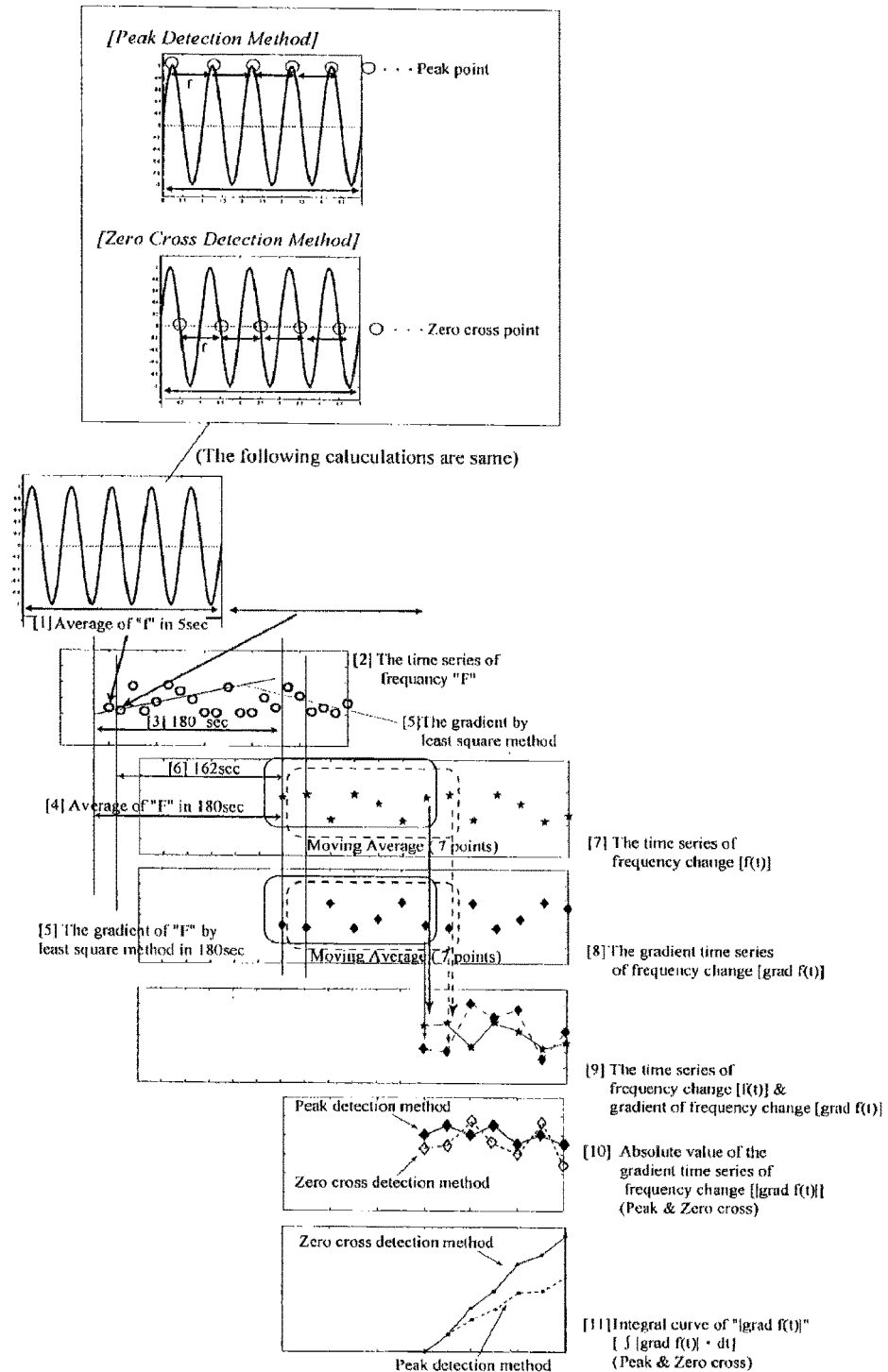
FIG. 9 is a diagram for explaining a method for obtaining a frequency fluctuation time-series waveform, a base line of the frequency fluctuation time-series waveform, a frequency slope time-series waveform which is a slope time series of a frequency fluctuation, and an integral curve using a peak value of a pulse wave (heartbeat fluctuation) detected by the biological signal measuring means or a zero-crossing point.

The frequency fluctuation time-series analyzing and computing means (frequency fluctuation time-series analyzing and computing step) 613 sets a time window with a predetermined time width (preferably, 180 seconds) to the time-series waveform of the frequency of the air-pack pulse wave obtained by the frequency computing means 611 (Step [2] in FIG. 9) to obtain a mean value of the frequency (Steps [3] and [4] in FIG. 9). Next, movement calculation for obtaining a mean value of the frequency of the air-pack pulse wave for each predetermined time window (preferably, 180 seconds) set in the predetermined overlapped time (preferably, 162 seconds) is performed so that the mean value is plotted. Then, the time series change of the mean value of the frequency plotted for each time window is outputted as a frequency fluctuation time-series waveform (Step [7] in FIG. 9). Then, when the frequency slope time-series waveform and the frequency fluctuation time-series waveform are outputted at the same time, it is as shown at Step [9] in FIG. 9. The heartbeat can be acquired from the frequency fluctuation time-series waveform.

Here, the peak detecting method detects disturbance in a waveform of a biological signal or a state of a waveform, while the zero-crossing method detects a frequency component. That is, if they both match, it means proximity to a periodic function, while if they both differ from each other, it means that a plurality of components are superimposed on the waveform. The disturbance in the waveform indicates a state in which a high frequency component is superimposed on a low frequency component or a low frequency component is further superimposed on a low frequency component, the amplitude increases or decreases, which corresponds to sthenia or decline in the sympathetic nerve and relates to each state of over-tension/endurance, absent-mindedness, relaxation, looming, and activation. Therefore, by applying absolute value processing to the frequency slope time-series waveform obtained by the peak detecting method and the zero-crossing method, respectively, and comparing them, the state can be roughly determined on whether it is in an over-tensed state or in an endured state with enhanced sympathetic nerve, or in a relaxed state with predominance on the parasympathetic nerve. On the other hand, if a describing function is obtained from the frequency slope time-series waveform and if increase/decrease of the heartbeat or the like is obtained from the frequency fluctuation time-series waveform, a time-series waveform of the frequency obtained by the zero-crossing method is preferable. That is because the object of calculating the describing function is to know whether the state is activity metabolism or a change in resting metabolism or to know a degree of activeness/function decline in each metabolism by examining a degree of a change in the waveform.

The differentiating means (differentiating step) 614 differentiates a time-series waveform of a frequency slope obtained by the frequency slope time-series analyzing and computing means 612 and examines a momentary fluctuation rate of the frequency slope time-series waveform.

The integrating means (integrating step) 615 integrates the time-series waveform of the frequency slope obtained by the frequency slope time-series analyzing and computing means 612 and examines accumulation of the frequency slope time-series waveform by elapsing of time.

The rectangular wave calculating means (rectangular wave calculating step) 616 acquires a peak of the time-series waveform of the frequency slope obtained by the frequency slope time-series analyzing and computing means 612, creates an envelope curve and draws a rectangular wave by obtaining an increasing/decreasing tendency from the slope of the envelope curve. That is, a rectangular wave is drawn such that a section with the slope of the envelope curve having an increasing tendency as positive and a section with a decreasing tendency as negative.

The describing function calculating means (describing function calculating step) 617 is means that applies fast Fourier transform to the frequency slope time-series waveform in the first time zone set arbitrarily and also applies fast Fourier transform to the frequency slope time-series waveform in the second time zone after the first time zone and obtains the describing function (equivalent transfer function) between the both by "fast Fourier transform in the second time zone ($a_2+(a_2$ is a real number part, $b_2$ is an imaginary number part)/fast Fourier transform in the first time zone ($a_1+i \cdot b_1$ . . . ($a_1$ is a real number part, $b_1$ is an imaginary number part)". That is, by obtaining the describing function between the both by having the frequency slope time-series waveform in the first time zone as an input function and the frequency slope time-series waveform in the second time zone as an output function, a basic state is offset, the state of a change remains, and a change in the homeostatic function of a person in the first time zone and the second time zone is captured. The first time zone and the second time zone are not limited as long as they are time widths from which a function of a frequency slope time-series waveform in each time zone can be obtained and can be set within a range of a half period to three periods (approximately 3 minutes to approximately 20 minutes, for example). It may be set statistically within a predetermined range or the time widths of the first time zone and the second time zone may be set for each individual.

The obtained described function is expressed as "$(a_1a_2+b_1b_2)/(a_1{}^2+b_1{}^2)+i\ (a_1b_2-a_2b_1)/(a_1{}^2b_1{}^2)$". It is set to "$(a_1a_2+b_1b_2)/(a_1{}^2+b_f{}^2)$"=A and "$i\ (a_1b_2-a_2b_1)/(a_1{}^2\ b_1{}^2)$"=B, and a square root of "$A^2+B^2$" is acquired as a describing function amplitude value. By this describing function amplitude value, state changes in the two time zones are captured. The value can be set arbitrarily and may be set for each individual or may be statistically set to a predetermined value. That is, such setting can be made that the state is a resting state or a looming state or the state in which sympathetic nerve compensation action is operating or the like if the value is a predetermined value or within a range of values.

The absolute value processing means (absolute value processing step) 618 applies absolute value processing to the frequency slope time-series waveform obtained by the frequency slope time-series analyzing and computing means 612 and outputs the result. At this time, the absolute value processing means 618 applies the absolute value processing to the frequency slope time-series waveforms obtained by using both the peak detecting method and the zero-crossing method and outputs the results. Specifically, the frequency computing means 611 acquires the time-series waveform of the frequency of a biological signal using the peak detecting method and also acquires the time-series waveform of the frequency of the biological signal using the zero-crossing method. Then, the frequency slope time-series analyzing and computing means 612 acquires the frequency slope time-series waveform for each of the time series waveforms of the frequencies by the peak detecting method and the zero-crossing method, and the absolute value processing means 618 applies the absolute value processing to each of the frequency slope time-series waveforms (Step [10] in FIG. 9).

As described above, the peak detecting method detects disturbance in the waveform of the biological signal in which a high frequency component is added to a low frequency component, while the zero-crossing method detects a low frequency component of the biological signal having less disturbance in the waveform. That is, if they match each other, it means that less superimposed component is contained, while if they differ from each other, it means that more superimposed component is contained. Therefore, by comparing the two pieces of data obtained by the absolute value processing means 618, state determination can be made on whether the state is the over-tensed state or in the endured state in which the sympathetic nerve system is enhanced, the parasympathetic nerves predominate due to decline of the sympathetic nerves, the relaxed state is induced with predominance of the parasympathetic nerve without decline of the sympathetic nerve, a function decline state caused by decline of both the sympathetic/parasympathetic nerve or a state requiring a rest. That is, if the absolute value calculated by using the zero-crossing method is higher than the absolute value calculated by using the peak detecting method by the absolute value processing means 618, the state is enhanced sympathetic nerve, while if not, the state can be determined to be a state with predominance on the parasympathetic nerve (See FIG. 8A).

The homeostatic function stage calculating means (homeostatic function stage calculating step) 619 acquires a stage of the homeostatic function level by using at least one or more of the frequency slope acquired by the frequency slope time-series analyzing and computing means 612, the differential value acquired by the differentiating means 614, the integral value acquired by the integrating means 615, the sign of the rectangular wave acquired by the rectangular wave calculating means 617, the describing function amplitude value acquired by the describing function calculating means 618, and two absolute values of the frequency slope time-series waveform acquired by the absolute value processing means 619. Applicability to which one of the above-described homeostatic function stages 1 to 5 is determined by these combinations. For example, if the frequency slope and the integral value are not less than the predetermined value, it is determined as the "homeostatic function stage 1" or if the differential value is not more than a predetermined value, the sign of the rectangular wave is "negative", the describing function amplitude value is not less than a predetermined value, and are the "peak predominates" in the two absolute values, it is determined to be the "homeostatic function stage 4". These combinations, threshold values in determination and the like are not limiting but can be determined through statistic processing of data of a plurality of subjects or can be set for each individual.

The state determination by the homeostatic function stage calculating means 619 is preferably made by combining the indexes as follows:

(1) The state is determined to be a homeostatic function stage 1:
   if the frequency slope time-series waveform by the zero-crossing method is positive, or
   if an integral waveform of the frequency slope time-series waveform by the zero-crossing method is positive
since, if these waveforms are positive, the sympathetic nerve activities of a person predominate, and it is suitable to be determined as a highly active state.

(2) The state is determined to be homeostatic function stage 2:
   if the frequency slope time-series waveform by the zero-crossing method is negative and if a ratio of the slope this time to the slope the previous time is a predetermined value or more and this ratio occurs a predetermined number of times or less, or
   if the integral waveform is within a range of a predetermined value,
since, even if the frequency slope time-series waveform is negative, if it is not less than a predetermined value or if the integral waveform is within a range of a predetermined value, a certain degree of active state is maintained.

(3) The state is determined to be homeostatic function stage 3:
   if the frequency slope time-series waveform by the zero-crossing method is negative, the ratio of the slope this time to the slope the previous time is a predetermined value or more and this ratio occurs a predetermined number of times or more, or
   if the integral waveform is within a range of a predetermined value (a range lower than that of the homeostatic function stage 2), or
   if the differential waveform is not more than a predetermined value,
since the balance between the sympathetic nerve and the parasympathetic nerve shows a good state within these ranges.

(4) The state is determined to be homeostatic function stage 4:
 if the differential waveform is not more than a predetermined value (value lower than that of the homeostatic function stage 3), or
 if the integral waveform is within a range of a predetermined value (value lower than that of the homeostatic function stage 3), or
 if the describing function amplitude value of the slope time-series waveform is not less than a predetermined value, the rectangular wave is negative, and the absolute value calculated by the peak detecting method becomes more predominant than the absolute value by the zero-crossing method,
since the parasympathetic nerve activities tend to gradually become predominant in these ranges.

(5) The state is determined to be homeostatic function stage 5:
 if the differential waveform is not more than a predetermined value (value lower than that of the homeostatic function stage 4), or
 if the integral waveform is not more than a predetermined value (value lower than the lower limit value in the case of the homeostatic function stage 4), or
 if the describing function amplitude value of the slope time-series waveform is not less than a predetermined value (value higher than that of the homeostatic function stage 4), the rectangular wave is negative, and the absolute value calculated by the peak detecting method is more predominant than the absolute value by the zero-crossing method,
since the parasympathetic nerve activities become predominant and fatigue is felt due to functional decline in these ranges.

(6) The state is determined to be sleeping prediction:
 if the absolute value calculated by the zero-crossing method is more predominant than the absolute value calculated by the peak detecting method, the rectangular wave is positive, and the graph indicating the homeostatic function stage drops over 2 stages or more,
since it is large movement departing from the range of fluctuation and microsleep occurs after this phenomenon occurs.

Here, the conventional determination having been made by the applicant by using the frequency slope time-series waveform and the frequency fluctuation time-series waveform is made mainly on a state caused by a metabolic change of a person called a sleep prediction signal. That is, a process in which a human body is getting tired one-sidedly as time elapses is mainly examined. However, the display by the line graphs as in FIGS. 11A to 11E displayed by the homeostatic function stage calculating means 619 in this embodiment is made by combining a plurality of indexes, that is, the frequency slope, the differential value, the integral value, the sign of the rectangular wave, the describing function amplitude value, and the absolute value as described above. Thus, not only the state change of a person caused by the metabolic action but a recovering performance and an attenuation performance of the homeostatic function in each state are also suggested, and activation caused by the stimulation of the brain and the state change can be also examined. The mechanism is as follows:

First, in the sleep state, the metabolic energy is at the lowest level, while in the normal/motion state, the energy level is at a high level, and the resting state is located inbetween. The steady driving state in the relaxed state has an energy level close to the resting state. On the other hand, struggle against sleep, consideration/attention to the peripheral situation, dangerous driving and the like raises the heartbeat and brings the state close to the normal/motion state. Maintenance of homeostasis in each state is adjusted so that a fluctuation width determined by the physical/mental capabilities of an individual is not departed.

It is known that characteristics of the state change of a person can be extracted by low-dimensional chaos. The fluctuation of the homeostatic function in the sleep state fluctuates chaotically and it fluctuates at random or periodically (hereinafter this is called as non-chaotically) in the normal/active state. In the state indicating this non-chaotic fluctuation, adaptability to an environmental change such as an external stress becomes poor. Under the situation in which a chaotic fluctuation is shown while a driver is driving a car, the driver cannot perceive external vibration easily and is easily subjected to an influence of fluctuation of respiration and heartbeat. That is, the chaotic fluctuation minimizes an energy consumption amount for maintaining homeostasis and suppresses progress of fatigue. The driver in this state is induced into the relaxed state, and over-tension of sympathetic nerve is alleviated. On the other hand, in the non-chaotic fluctuation state, the external vibration can easily transmit to the driver, influencing respiration and heartbeat, wasteful force is raised in the organs, and a resistant feeling of fatigue is generated. This feeling of fatigue increases the energy consumption amount, and the gradient of progress of fatigue becomes larger. Here, the person enters a state with enhanced sympathetic nerves.

The homeostatic function of a human body was considered by replacing it with a spring-mass-damper system. The spring system is a function for accumulating energy and converting it to a force, and this was supposed as the sympathetic nerve system. On the other hand, the damper system is a function for damping the energy, and this was supposed as the parasympathetic nerve system. The mass is supposed as a cardiocirculatory organ system which is a life-sustaining function. A biological body was controlled by two functions of the homeostatic function, that is, a central system in charge of homeostasis of the life-sustaining function and a periphery system relaxing stimulation from the external world. Since the characteristics of these two functions include non-linearity, they are expressed as the describing functions. An air-pack sensor placed on the back part mainly captures the state close to the central system. A signal captured by the air-pack sensor is fluctuation in aorta caused by movement of the heart.

A human being controls maintenance of homeostasis by the autonomous nerve system. The parasympathetic nerve does not cause large fluctuation. Therefore, predominance of the parasympathetic nerve is generated by function decline of the sympathetic nerve. That is, stability of the heartbeat is controlled by the balance of the sympathetic nerve to the parasympathetic nerve. An excessive rise of the heartbeat is suppressed by the parasympathetic nerve (as a result, vagovagal reflex occurs and infrequency pulse develops.). A human being has a natural state in which the sympathetic nerve and the parasympathetic nerve are balanced, a tensed state with enhanced sympathetic nerve, a fatigued state in which functions of both the sympathetic nerve and the parasympathetic nerve decline, and a relaxed state corresponding to a recovery period with predominance on the parasympathetic nerve, and combination of them produces flexibility to deal with a change and helps maintenance of homeostasis.

Figure 8A:
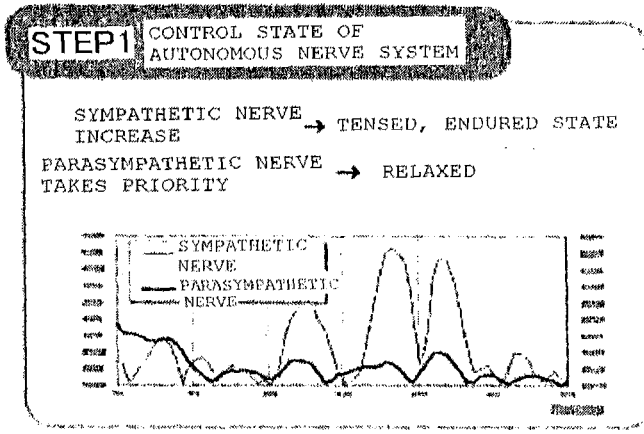
FIGS. 8A to 8C are conceptual diagrams for explaining a mechanism of the state estimation.
Figure 8B:
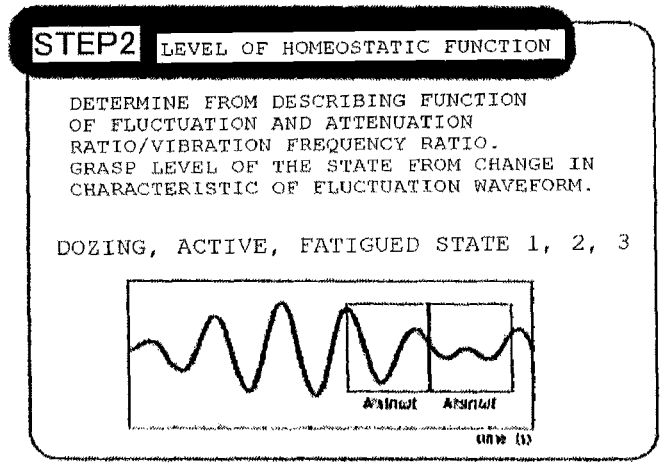
Figure 8C:
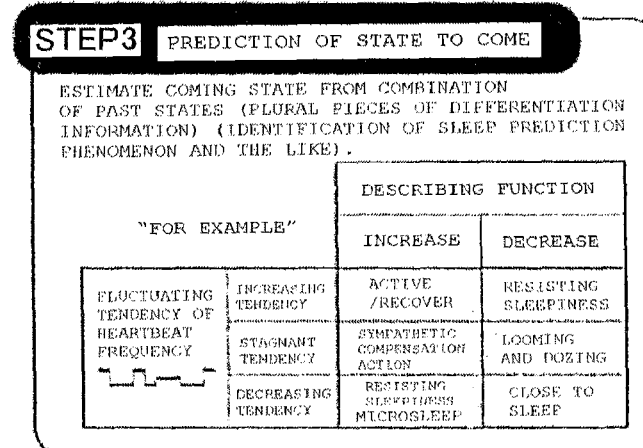

From the above, estimation of a human state is to find out a change in the autonomous nerve system as an inverse problem. First, it is determined whether the human state is in a tensed state or a relaxed state from differential information of fluctuation of a biological body and degree of occurrence of fluctuation in the sympathetic nerve and the parasympathetic nerve (FIG. 8A). Then, it is determined whether the state is an active state, a resting state, a function decline state or a transitional state thereof by examining a characteristic change in the fluctuation waveform (FIG. 8B). Subsequently, the state after that is estimated from the combination of the past states (FIG. 8C). The combination of the past states is information on the state protrusion of the fluctuation waveform indicating enhanced sympathetic nerve and the number of occurrences thereof, the state of rapid progress of fatigue (rapid change in the homeostatic function), the number of the rapid changes, and a rectangular wave indicating the tendency of fluctuation in the frequency of heartbeat. They are helpful in estimation of a sleeping prediction phenomenon.

On the other hand, considering a process of fatigue according to contribution rates of mental fatigue and physical fatigue, natural progress of fatigue has been said to have three stages, that is, a stage in which fatigue is not felt, a stage in which the feeling of fatigue is compensated for by the compensating action of the sympathetic nerve and the feeling of fatigue is not felt, and a stage in which the feeling of fatigue is felt and a human error occurs.

However, it is considered that the contribution rate of mental fatigue is high in the tensed state, while the physical fatigue governs the progress of fatigue in the relaxed state. However, in the prior-art idea on the progress of fatigue does not consider suppression of fatigue by activation of the brain function. Under a general driving environment, the brain function is activated regardless of the progress degree of fatigue. This activation of the brain function includes creativity, curiosity and the like, and they induce awakening.

This is known from the fact, as shown in FIGS. 11A to 11E, that not only an increase/decrease by the biological fluctuation (metabolic action) but also a process in which the homeostatic function stage rapidly returns to the original stage occurs or a process in which the homeostatic function stage rarely progresses even if time elapses. That is, it is considered that the graph shows not only the state in which a human body is tired but also an enlarging process of an allowance for the fatigue. The enlargement of the allowance for the fatigue is based on an instruction from the brain, that is, activation caused by activation of the brain, and this graph can be considered to capture not only the state change of a person by the metabolic action but also a change in the state of the person caused by the brain action (particularly, the "state of mind"). Therefore, in the present invention, the estimation of the "state of a person (biological body)" includes not only inference of the state change caused by the metabolic action but also an inference of the progress of fatigue from the state of performance decline through the fluctuation state of the homeostatic function and estimation of the state change by reactivation caused by activation of the brain.

The state estimation process by the biological body state estimation device 60 will be described on the basis of a flowchart in FIG. 7. First, an air-pack signal by movement of an aorta on the back part is obtained by the biological signal measuring means 1 (S101). The air-pack signal at S101 is not the signal itself of pressure fluctuation of the air pack but a signal after being subjected to predetermined filtering (analog filtering process to reduce a noise signal other than the biological signal). This air-pack signal can be also processed by the frequency computing means 611, but in order to improve accuracy, the filtering means is further applied to this air-pack signal (S102), and a signal waveform (air-pack signal digital filter waveform) of a frequency area required for analysis is obtained (S103). This further filtering means (hereinafter referred to as "digital filtering means") removes vibration (noise) inputted from a car-body floor during running of an automobile as much as possible. Thus, this digital filtering means is configured such that, under a static environment (the phrase "under a static environment" referred to in this description also means under a measuring environment in an idling state (a state in which vibration caused by irregularity on the road surface such as during running is not inputted) that can be considered to be a substantially static environment (that is, a static equivalent environment) in addition to the measuring environment in which the engine is not started and vibration is not inputted at all), a biological signal is measured by the biological signal measuring means 1 for several seconds to several tens of seconds, its mean frequency is obtained, and a frequency band (a lower-limit frequency and an upper-limit frequency) to be filtered is set with the mean frequency as a reference value. As a result, mixing of vibration waveform inputted through the car-body floor from the road surface during running becomes less, and an air-pack signal filter waveform obtained under the static environment to which the digital filtering means is applied and an air-pack signal digital filter waveform obtained during running form substantially the same waveform supposing that the homeostatic function stage of the person is the same.

Figure 10A:
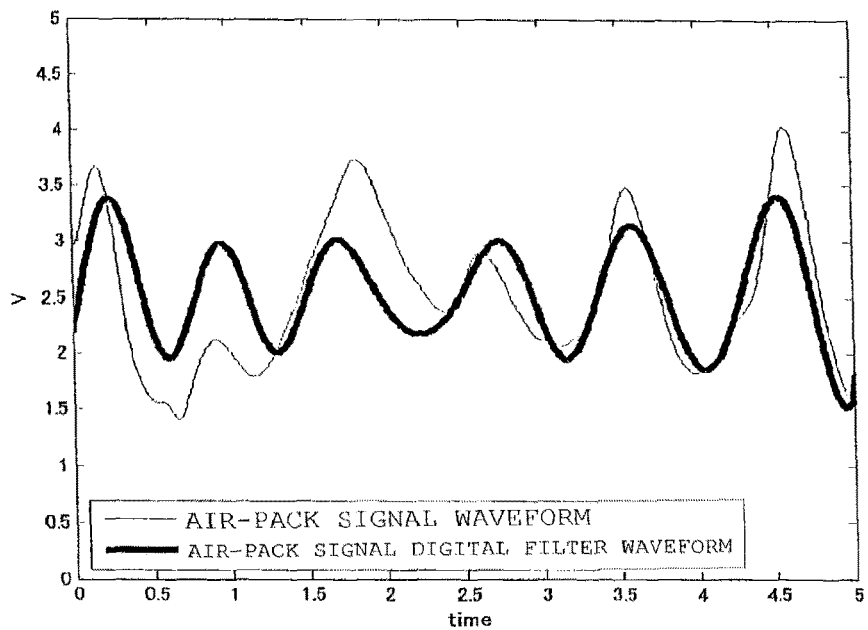
FIG. 10 shows a waveform to which filtering means is applied and a waveform to which the filtering means is not applied in the biological body state estimation device according to the embodiment, FIG. 10A showing a measurement result obtained in an idling state of an automobile, and FIG. 10B showing a measurement result in a running state.
Figure 10B:
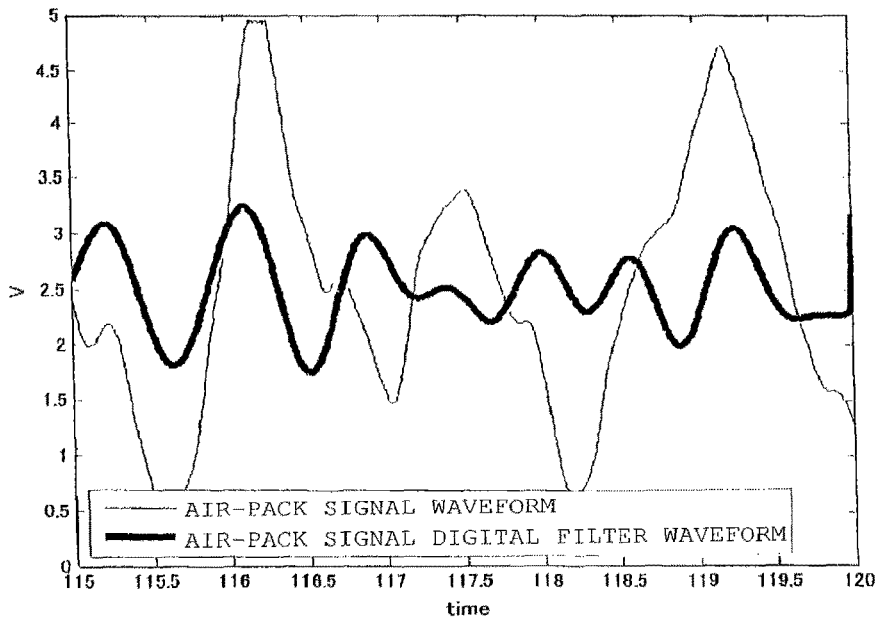

A method of acquiring the mean frequency to be a reference in the digital filtering means is not limited, but in this embodiment, a waveform of the biological signal itself obtained by the biological signal measuring means 1 (that is, the pressure waveform) is differentiated (or preferably, second-order differentiation), full-wave rectification is applied to the differential waveform, and moreover, a low-pass filter is applied. The filtering frequency of the low-pass filter is set as appropriate within a range of 1 to 3 Hz which is a general frequency of the biological signal caused by movement of an aorta on the back part. A peak is acquired from the waveform subjected to the low-pass filter, and moreover, a mean frequency is acquired from a time interval of the peaks. The waveforms obtained by applying filtering by this method are shown in FIGS. 10A and 10B. FIG. 10A shows comparison between the air-pack signal waveform and the air-pack signal digital filter waveform in the idling state under the static equivalent environment, while FIG. 10B shows comparison between the air-pack signal waveform and the air-pack signal digital filter waveform during driving (during running). From these figures, the air-pack signal waveform shows a vertically protruding disturbed waveform during driving (running), different from that in the idling state under the static equivalent environment, while the air-pack signal digital filter waveform is substantially the same waveform both in the static idling state and during driving (running). Therefore, to measure the biological signal in advance in the idling state (static equivalent environment) before running and performing filtering by using it as a reference is extremely preferable in obtaining a measurement result with high accuracy.

The air-pack signal filter waveform obtained at S103 is processed by the frequency computing means 611 and the time-series waveform of the frequency of the air-pack signal filter waveform is acquired by the zero-crossing method and the peak detecting method (S104). Subsequently, the frequency slope time-series waveform, its differential waveform (differential value), the integral waveform (integral value), the rectangular wave, and the describing function (describing function amplitude value) are acquired by using the time-series waveform of the frequency of the air-pack signal filter waveform by the zero-crossing method, and the waveforms obtained by applying the absolute value processing to the frequency slope time-series waveform of the zero-crossing method and the frequency slope time-series waveform by the peak detecting method are acquired (S105). Subsequently, the homeostatic function stage is determined by the homeostatic function stage calculating means 619 (S106), and the result is outputted to the display means 65 by the output means 62 (S107).

Test Example 1

As a test for verifying effectiveness of a signal of pressure fluctuation caused by movement of an aorta of the back part (air pack signal) detected by the biological signal measuring means 1 provided with the air pack 10 according to this embodiment, comparison with electrocardiograms was made.

Subjects are four people in their 20's to 30's (two men and two women). Measurement items are electrocardiograms and a signal of pressure fluctuation (air pack signal) obtained from the air pack brought into contact with portions in a human body. The air pack signal was sampled from the cervical part, the upper arm, the radius, and the femora by using the automobile seat 500 of the above-described embodiment and a mattress for a bed. The experiment was conducted by measuring for 3 minutes in the sitting position and the supine position, respectively.

FIG. 14 are comparison results of the electrocardiogram and the air pack signal of a 30-year-old female subject, and FIG. 14A shows a part of original waveforms of the air pack signal and the electrocardiogram. By comparing the original waveform of the electrocardiogram with the original waveform of the air pack signal, it can be observed that a peak value (R wave) of the electrocardiogram substantially matches the minimum value of the air pack signal. FIG. 14B shows a result of comparison of the heartbeat frequency time-series waveforms calculated from the air pack signal and the electrocardiogram. Regarding the heartbeat frequency, the waveforms match in the electrocardiogram, the back part, and the cervical part both in the sitting position and the supine position. The other three subjects showed similar results, and particularly the electrocardiogram and the back-part air pack signal stably matched. Moreover, in the state of the supine position, even if temporary disturbance was observed due to a body motion, high correlation with the electrocardiogram was shown, and the disturbance did not lead to collapse.

The back-part air pack signal is a biological signal obtained from the portion closest to the heart and has high correlation with the cardiogram, and thus, the air pack sensor provided on the back part is considered to capture fluctuation in the aorta caused by movement of the heart. Moreover, reversal of polarity of the original waveforms of the electrocardiogram and the air pack signal is considered to correspond to the relation of dilation of the arterial vessel in the systole when the heart contracts and contraction of the arterial vessel in the diastole when the heart is relaxed and dilated by inflow of blood. A large shift between the electrocardiogram and the air pack signal shown at A, B, and C parts in FIG. 14B is caused by a body motion. That is, the air pack signal can be considered to be able to sensitively capture a change by the body motion. A slight body motion of the subject on an automobile seat with high restrictive characteristic cannot be captured as the A, B, and C parts in FIG. 14B, but a body motion by a large driving operation (such that the body is largely arched out to the front and the like) can be captured as the A, B, and C parts in FIG. 14B. These body motions are generated when a person is in an unstable state different from the usual stated or in an abnormal state, and thus, once a signal can no longer be detected by the air pack sensor, it can be determined to be an abnormal state.

Test Example 2

Analysis Example 1

Test Condition

A male subject A in his 50's, a female subject B in her 40's, and a male subject B in his 40's were made to travel back and forth by car between Higashi-Hiroshima city, Hiroshima Prefecture and Kurobe city, Toyama Prefecture. They stayed in Kurobe city on the first night and stayed in Kyoto city on the second night. They headed to Kurobe city from Higashi-Hiroshima city on the first day, from Kurobe city to Kyoto city on the second day, and on the third day travelled from Kyoto city to Osaka city, had a meeting and then, they headed to Higashi-Hiroshima city. The test was conducted while the three subjects took turns as appropriate in driving. The seat 500 in which the air pack 10 of this embodiment was incorporated in the seat back portion 510 was mounted on the driver's seat of the vehicle used for the test. The results are shown in FIG. 15 to 30. In the figures, A shows a frequency slope time-series waveform obtained from the frequency slope time-series analyzing and computing means 612 using the zero-crossing method (displayed by the "air-pack pulse wave frequency slope" in the figures) and a frequency fluctuation waveform obtained from the frequency fluctuation time-series analyzing and computing means 613 (displayed as the "air pack pulse wave frequency fluctuation" in the figures). B shows a change of a describing function (transmission function) obtained by the describing function calculating means 617 by using the frequency slope time-series waveform of A, and C shows a change of the rectangular wave obtained from the rectangular wave calculating means 616 by using the frequency slope time-series waveform of A. D shows a change (determination result) of the homeostatic function stage calculated by the homeostatic function stage calculating means 619 by using each data of A to C and F and the like. E shows a graph obtained by integrating an absolute value by the peak detecting method and an absolute value by the zero-crossing method obtained by the absolute value processing means 618, respectively. F shows a change in the time series of the absolute value by the peak detecting method and the absolute value by the zero-crossing method obtained by the absolute value processing means 618. G shows an integral waveform of the frequency slope time-series waveform.

(Consideration)

The determination result shown in D in each figure and the actual state of each subject will be mainly described.

(1) Male subject A, Kurobe area 1 (outward trip) (FIG. 15)

The subject felt a feeling of fatigue from the start of measurement to approximately 2000 seconds but maintained a relatively good state. Alleviation in the feeling of fatigue was caused by biological fluctuation, and the compensation action of the sympathetic nerve is not considered to take place. After that, a sleep prediction phenomenon occurred, and the fatigue progressed. Then, at some 3000 seconds, sleepiness occurred and gave up driving to someone else.

(2) Female subject B, Kurobe area 2 (outward trip) (FIG. 16)

A good state continued from 1800 to 3000 seconds. During the other time, traffic jam (a slow driving car blocked a fast lane) irritated the subject during driving. Occurrence of sleepiness is found at some 4200 seconds.

(3) Male subject A, Kurobe area 3 (outward trip) (FIG. 17)

A good state continued for the first 600 seconds, but traffic jam occurred after that, and the subject entered the fatigued state. The fatigue during this period was mainly caused by a mental factor, and the first sleep prediction signal occurred at some 5100 seconds. After that, the compensating action of the sympathetic nerve functioned, and the second sleep prediction signal occurred at some 9600 seconds. Due to the fatigue caused by irritation caused by traffic jam, driving at night, and tension, the driver had supper at occurrence of the second sleep prediction signal.

(4) Male subject A, Kurobe area 4 (outward trip) (FIG. 18)

After the supper, the subject regained energy but that did not last long, and the sympathetic compensation action against sleepiness occurred at some 1200 seconds. After that, a good state with enhanced sympathetic nerve lasted till 2000 seconds. In the middle, the level of the sympathetic nerve lowered to a state with predominance on the parasympathetic, and the first sleep prediction signal occurred. At 2300 seconds and after, natural progress of fatigue was found with drop of tension.

(5) Female subject B, Kurobe area 5 (outward trip), (FIG. 19)

The sympathetic compensation action occurred at the start of measurement, and the subject was in the fatigued state with tension. A section in which the brain function was considered to be activated in the relaxed state was found from some 1000 to 1850 seconds, and after that, the fatigue tended to recover, and the highly active state was induced though with some feeling of fatigue. This is considered that the activation of the brain function induced the relaxed state and promoted recovery from fatigue.

(6) Male subject A, Kurobe area 6 (outward trip) (FIG. 20)

Sleeping in the seat next to the driver was effective, and a state in which a feeling of fatigue was not felt was found till some 1200 seconds. After that, wakefulness naturally lowered, but this is considered to have been caused in conjunction with drop in circadian rhythm.

(7) Male subject A, Kyoto area 1 (return trip) (FIG. 21)

From the start to 700 seconds, an influence of fatigue from the previous day was found. After that, the subject lost his way and thus had to think. The activation of the brain function is considered to be induced by the effect of this thinking. When the activation of the brain function subsided, fatigue progressed as a counteraction.

(8) Male subject A, Kyoto area 2 (return trip) (FIG. 22)

The feeling of fatigue after the meeting increased the biological fluctuation, and the subject fell into the fatigued state all at once. The male subject A felt hungry, but discovery of a bakery around 1100 seconds raised the degree of arousal all at once.

(9) Male subject A, Kyoto area 3 (return trip) (FIG. 23)

The subject ate bread and that made him discursive, and the notice of "drive carefully" was displayed. After that, the feeling of fatigue was gently alleviated in the relaxed state. In the middle, the level of the sympathetic nerve lowered, and sleepiness occurred approximately twice. After that, biological fluctuation occurred, and the state got close to awakening again.

(10) Female subject A, Kyoto area 4 (return trip) (FIG. 24)

The feeling of fatigue was felt immediately after the start of driving, and enhancement of the sympathetic nerve was found. The tensed state continued and sleepiness occurred immediately before the subject finished driving.

(11) Male subject A, Kyoto area 5 (return trip) (FIG. 25)

Fatigue was felt from the beginning, and the subject tried to maintain homeostasis while fluctuating. The function decline was found, and the sympathetic compensation action occurred at approximately 2400 seconds. After that, sleepiness occurred but recovered by the sympathetic compensation action. After that, the tension relieved and entered the relaxed state, which is considered to have raised the feeling of fatigue.

(12) Male subject A, Kyoto area 6 (return trip) (FIG. 26)

After the rest, the subject resumed driving but he received a phone call on business during the rest. Immediately after the start of driving, the state quickly returned to that before the rest. After that, irritation seeming to be caused by the phone call continued. At 4600 seconds and after, rapid function decline and sleepiness occurred once each while the sympathetic nerve kept enhanced.

(13) Male subject A, Kyoto area 7 (return trip) (FIG. 27)

After the rest, the subject resumed driving. After the rest, tension and enhanced sympathetic nerve were relieved, and the feeling of fatigue occurred all at once. In order to solve the feeling of fatigue, the subject had an energy drink in the relaxed state and temporarily recovered but amplitude of the biological fluctuation became large after that, and the feeling of fatigue was alleviated. The energy drink is considered to promote recovery by biological fluctuation while inducing the subject to become relaxed.

(14) Male subject B, Higashi-Hiroshima area 1 (return trip) (FIG. 28)

No accumulation of fatigue. This subject dealt with a feeling of fatigue in a tensed state while dexterously using fluctuation. Sleepiness occurred after 2550 seconds. The function decline after that was caused by irritation due to a slow driving car blocking the lane.

(15) Male subject B, Higashi-Hiroshima area 2 (return trip) (FIG. 29)

Meal and rest solved the feeling of fatigue and recovered a good condition. Sleepiness and large fluctuation occurred as a counteraction to the tension, but the tensed state by the sympathetic compensation action recovered the state without feeling of fatigue.

(16) Male subject B, Higashi-Hiroshima area 3 (return trip) (FIG. 30)

At slightly after 1200 seconds, the feeling of fatigue suddenly appeared. It temporarily recovered due to the sympathetic compensation action but the recovery did not last long. At the end, expectation for arrival induced the tensed state, and the feeling of fatigue reduced.

From the above, the actual state of each of the subjects can be considered to match well with the state determined from the determination result shown in each figure D.

Test Example 3

Analysis Example 2

Test Condition

A cushion incorporating the air pack 10 of the above-described embodiment was attached to the seat back portion of a driver's seat of a large-sized truck, and an experiment on state estimation of a driver in long-distance driving at night was conducted. The experiment was conducted for a round trip on an express way for approximately 500 km between Tokyo and Osaka. The driver left Tokyo around 10 pm, took a rest for approximately 1 hour at a service station close to the middle point and then, resumed the experiment and headed for Osaka. After the driver arrived at Osaka around 5 am, he slept for approximately 6 to 8 hours and started the return trip experiment for Tokyo around 10 pm. In the return trip, too, as in the outward trip, the driver took a rest for approximately 1 hour at a service station close to the middle point. The subjects were four healthy men in their 30 to 40's. Biological signals used for the measurement were pressure waveforms sampled from the back parts.

(Consideration)

Figures 31A, 31B, 31C, 31D:
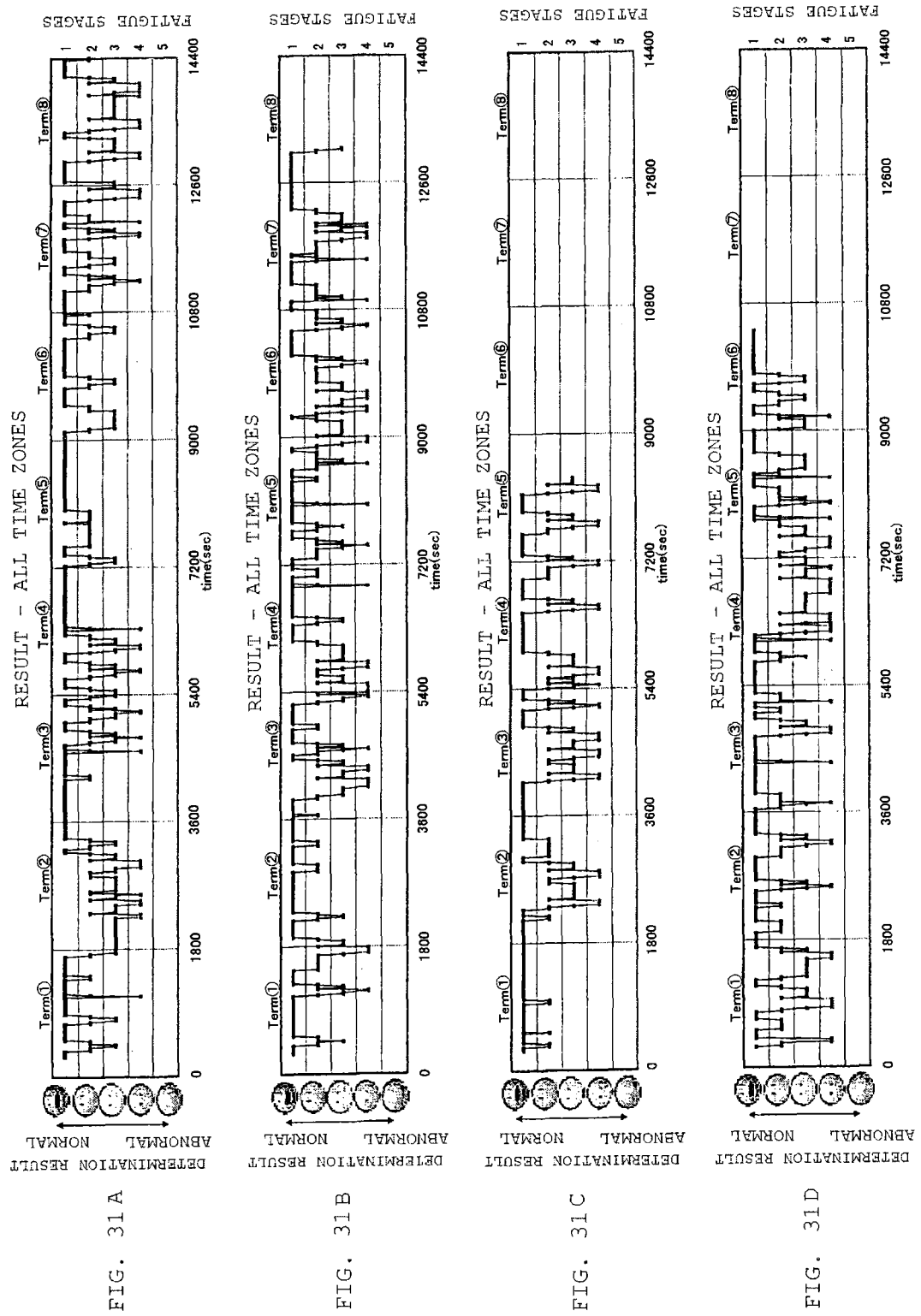
FIGS. 31A to 31D are diagrams showing results of fatigue experiments of a subject A conducted in a round trip between Tokyo and Osaka in a test example 3.

FIGS. 31A to 31D show results of the fatigue experiment conducted in the round trip between Tokyo and Osaka of a subject A. The vertical axis indicates the homeostatic function stages 1 to 5 (from the normal (highly active state) to abnormal (function decline state) in the figures), and the lateral axis indicates the time axis. FIG. 31A shows the state of a change in the homeostatic function between Tokyo and Miai of the subject A on the outward trip. The center axis of fluctuation is located in the homeostatic function stage 2 or 3, and the fluctuation occurs on the basis of that. Moreover, the ratio of the homeostatic function stage 1 amounted to 52.5% of the entire route, and it can be observed that the subject was taking efforts in driving in the tensed state with predominance on the sympathetic nerve.

FIG. 31B shows a degree of progress of fatigue of the subject A on the return trip from Osaka to Ogasa. Similarly to FIG. 31A, in the subject A in FIG. 31B, fluctuation occurred on the basis of the homeostatic function stage 2 or 3. A difference is that the time zone staying in the homeostatic function stage 1 is shorter. The progress of fatigue certainly becomes quicker, and it seems that the fatigue cannot be fully relieved even after the long-time sleep.

FIG. 31C shows a degree of progress of fatigue of the subject A on the outward trip from Miai to Oasaka after a rest. In this process, the state substantially the same as that before the rest was shown. Therefore, the rest can be considered to be effective for relieving fatigue. FIG. 31D shows the state of a change in the homeostatic function of the subject A on the return trip from Ogasa to Tokyo after the rest. In this process, since a phenomenon different from that in the outward trip in FIG. 31C is shown, it is assumed that the rest is temporarily effective in relieving fatigue but does not have an improvement effect for the accumulated fatigue. From these four examples, it is suggested that activation of the homeostatic function can be expected by having a rest during the outward trip, even though the effect is temporary. Regarding the rest on the return trip, the improvement effect is not found due to accumulation of fatigue, but there seems to be a fatigue suppression effect. Similar results were obtained for the other three subjects.

Figure 32A:
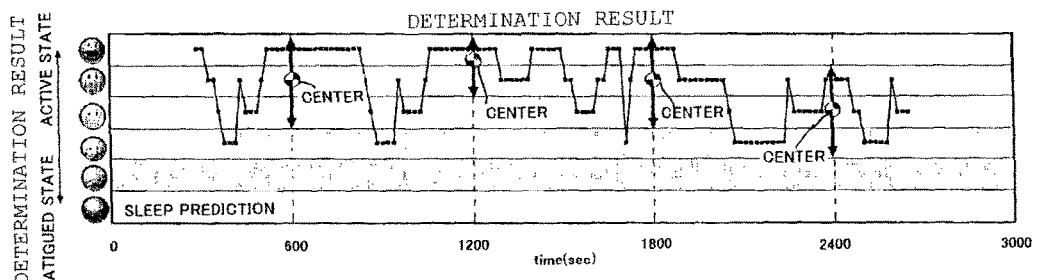
FIGS. 32A to 32C are diagrams showing other display examples of graphs showing the homeostatic function level by plotting in a time series.
Figure 32B:
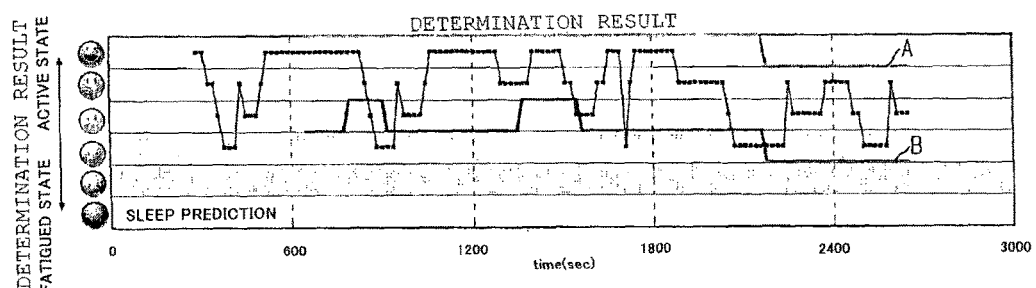

Even if fatigue progresses as time elapses, when the graph obtained by plotting the homeostatic function level in a time series is within a range of fluctuation corresponding to biological fluctuation (in a range of one to two stages of the homeostatic function level with respect to the substantially center position of the fluctuation at that point), there is no problem. Thus, in order to facilitate visual grasping on whether or not the graph is within the range, the range of fluctuation is preferably made clear as shown in FIGS. 32A and 32B. In FIG. 32A, the range of the fluctuation with respect to the center is indicated by vertically extending arrows, while in FIG. 32B, the range is surrounded by an A line indicating the upper limit and a B line indicating the lower limit.

Figure 32C:
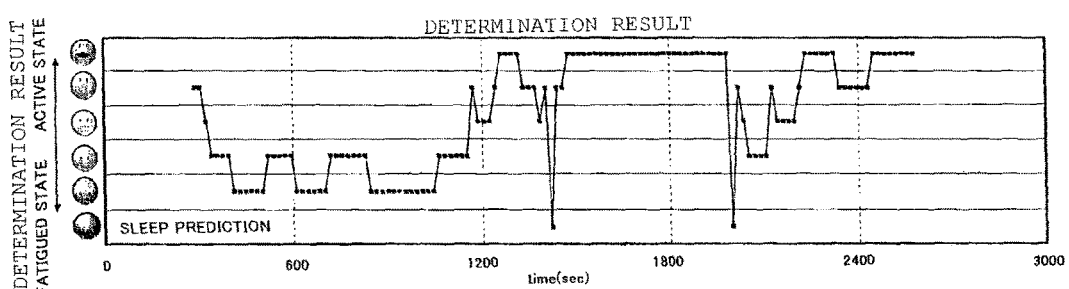

Moreover, as shown in FIG. 32C, in order to clearly display occurrence of the sleep prediction signal in the time-series graph, the graph can be configured to display the stage of the "sleep prediction" under the homeostatic function stages 1 to 5. If the graph rapidly drops and it is determined to be sleep prediction by the abnormal state determining means of the determining means 63, the lower end of the graph at that time is displayed by being extended to the "sleep prediction" stage displayed on the lowermost stage. As a result, timing when the sleep prediction signal occurs can be visually and easily grasped.

Figure 33:
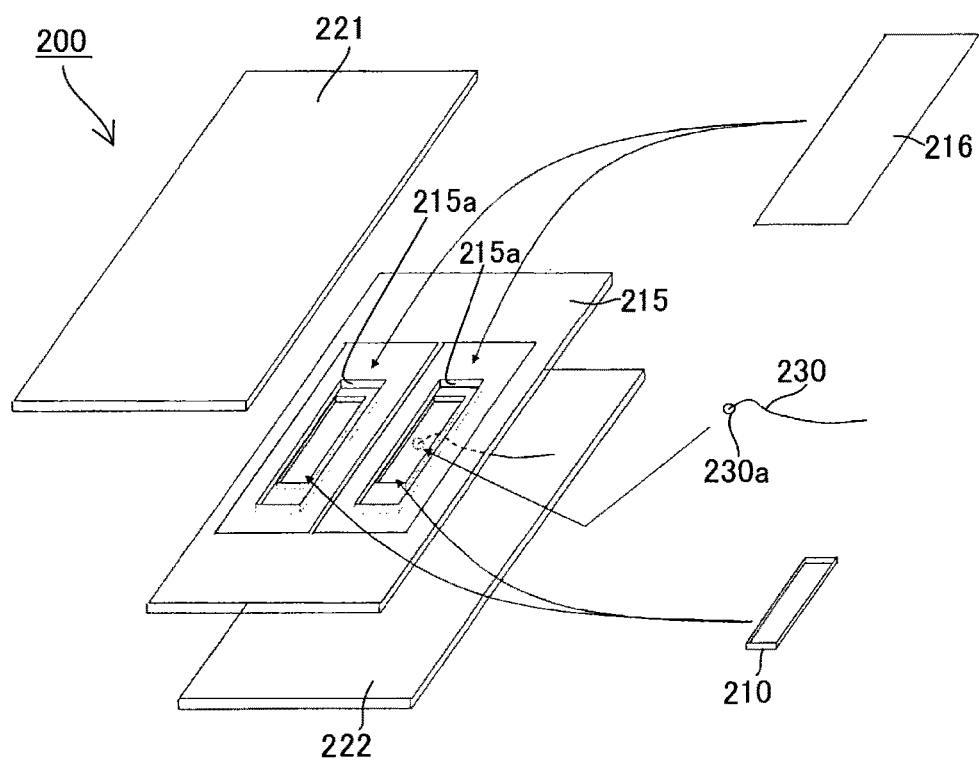
FIG. 33 is a view showing an example of the biological signal measuring means according to another embodiment.

As the biological signal measuring means, not only that using the above-described air pack 10 but also that shown in FIG. 33 can be used. Biological signal measuring means 200 shown in FIG. 33 includes three-dimensional solid knitted fabric 210, a three-dimensional solid knitted fabric support member 215, a film 216, plate-shaped expanded bodies 221 and 222, and a vibration sensor 230.

For the three-dimensional solid knitted fabric 210, that similar to the biological signal measuring means 1 shown in FIG. 1 and the like can be used. The three-dimensional solid knitted fabric 210 preferably has a load-deflection characteristic in the thickness direction within a range up to the load of 100 N when it is placed on a measurement plate and pressurized by a pressurizing plate having a diameter of 30 mm or a diameter of 98 mm and a spring constant approximated to the load-deflection characteristic of muscle of a human breech. Specifically, that with the spring constant within a range of 0.1 to 5 N/mm when being pressurized by a pressurizing plate with a diameter of 30 mm or the spring constant within a range of 1 to 10 N/mm when being pressurized by a pressurizing plate with a diameter of 98 mm is preferably used. By using that approximated to the load-deflection characteristic of the muscle of a human breech, the three-dimensional solid knitted fabric is balanced with the muscle, and when a biological signal is transmitted, the three-dimensional solid knitted fabric generates vibration similar to the human muscle, and the biological signal can be transmitted without large attenuation.

The plate-shaped expanded bodies 221 and 222 are preferably formed of an expanded bead body. As the expanded bead body, a foamed molding by a resin bead method containing at least any one of polystyrene, polypropylene, and polyethylene can be used, for example. The plate-shaped expanded bodies 221 and 222 made of an expanded bead body transmit a biological signal accompanied by slight amplitude as membrane oscillation (lateral wave) due to the characteristic of a spherical resin membrane formed by foams constituting individual micro beads. This membrane oscillation (lateral wave) is transmitted to the three-dimensional solid knitted fabric as string vibration, the membrane oscillation (lateral wave) and the string vibration are superimposed with each other, and the biological signal is detected by a vibration sensor 230, which will be described later, as amplified mechanical vibration by superimposition of the membrane oscillation (lateral wave) and the string vibration. Therefore, detection of the biological signal is facilitated.

If the plate-shaped expanded bodies 221 and 222 are composed of expanded bead bodies, the expansion ratio is preferably within a range of 25 to 50 times and the thickness is preferably not more than a mean diameter of the bead. If the mean diameter of the bead with 30-times foaming is 4 to 6 mm, for example, the thickness of each of the plate-shaped expanded bodies 221 and 222 is subjected to slice cutting to approximately 3 to 5 mm. As a result, soft elasticity is given to the plate-shaped expanded bodies 221 and 222, which makes them resonate with vibration with small amplitude, and a lateral wave transmitting on the film can no longer be attenuated easily. The plate-shaped expanded bodies 221 and 222 may be arranged on the both sides of the three-dimensional solid knitted fabric 210 in a sandwiching manner as in this embodiment, but they can be also arranged only on one side or preferably only on the seat back side.

Here, the three-dimensional solid knitted fabric 210 having a strip shape within a range of width of 40 to 10 mm and a length of 100 to 300 mm is used. The knitting with this size can easily cause pre-compression (state in which tension is generated in connecting yarns) in the three-dimensional solid knitted fabric 210, and an equilibrium state can be easily made between a person and the three-dimensional solid knitted fabric 210. In this embodiment, in order to reduce a sense of discomfort felt by a person when the back part is in contact, two sheets are symmetrically disposed while sandwiching the portion corresponding to the spine. In order to arrange the three-dimensional solid knitted fabric 210 easily at a predetermined position, the three-dimensional solid knitted fabric 210 is preferably configured to be supported by a three-dimensional solid knitted fabric support member 215. The three-dimensional solid knitted fabric support member 215 is molded into a plate shape, and two vertically long arrangement through holes 215a and 215a are formed at symmetrical positions while sandwiching the portion corresponding to the spine. The three-dimensional solid knitted fabric support member 215 is preferably formed of an expanded bead body formed having a plate shape similarly to the above-described plate-shaped expanded bodies 221 and 222. Preferable ranges of an expansion ratio and thickness when the three-dimensional solid knitted fabric support member 215 is formed of an expanded bead body are the same as that of the plate-shaped expanded bodies 221 and 222. However, in order to generate the membrane oscillation (lateral wave) more distinctively by a biological signal, the thicknesses of the plate-shaped expanded bodies 221 and 222 laminated above and below the three-dimensional solid knitted fabrics 210 and 210 are preferably smaller than the thickness of the three-dimensional solid knitted fabric support member 215.

While the two pieces of three-dimensional solid knitted fabrics 210 and 210 are inserted into the arrangement through holes 215a and 215a formed in the three-dimensional solid knitted fabric support member 215, films 216 and 216 are laminated on the front side and the back side of the three-dimensional solid knitted fabrics 210 and 210. The formation positions of the arrangement through holes 215a and 215a (that is, the disposed positions of the three-dimensional solid knitted fabrics 210 and 210) are preferably positions corresponding to regions where fluctuation caused by movement with stroke of atrium and aorta (particularly, the "descending aorta") and movement of an aorta valve (cardiac fluctuation wave) can be detected. As a result, the three-dimensional solid knitted fabrics 210 and 210 are sandwiched by the plate-shaped expanded bodies 221 and 222 on the upper and lower faces and the peripheral edge portion is surrounded by the three-dimensional solid knitted fabric support member 215, so that the plate-shaped expanded bodies 221 and 222 and the three-dimensional solid knitted fabric support member 215 perform the function of a resonant-vibration box (resonant box).

Moreover, the three-dimensional solid knitted fabrics 210 and 210 are preferably thicker than the three-dimensional solid knitted fabric support member 215 in use. That is, if the three-dimensional solid knitted fabrics 210 and 210 are arranged in the arrangement through holes 215a and 215a, they should have a thickness relationship such that the front surface and the back surface of the three-dimensional solid knitted fabrics 210 and 210 protrude from the arrangement through holes 215a and 215a. As a result, when the peripheral edge portions of the films 216 and 216 are bonded to the peripheral edge portions of the arrangement through holes 215a and 215a, the three-dimensional solid knitted fabrics 210 and 210 are pressed in the thickness direction. Thus, a tension caused by a reaction force of the films 216 and 216 is generated, and solid vibration (membrane oscillation (lateral wave)) can easily occur in the films 216 and 216. On the other hand, pre-compression occurs also in the three-dimensional solid knitted fabrics 210 and 210, tension caused by a reaction force is generated also in the connecting yarn holding the thickness form of the three-dimensional solid knitted fabric, and string vibration can easily occur. The films 216 and 216 are preferably provided on the both the front side and the back side of the three-dimensional solid knitted fabrics 210 and 210, but they may be configured to be provided at least on one of them. As the films 216 and 216, a plastic film made of polyurethane elastomer (for example, Product Number "DUS605-CDR" produced by Sheedom Co., Ltd.) and the like can be used, for example.

The vibration sensor 230 is disposed by being fixed to either one of the three-dimensional solid knitted fabric 210 before the above-described films 216 and 216 are laminated. The three-dimensional solid knitted fabric 210 is composed of a pair of ground knitted fabrics and the connecting yarn, but since the string vibration of each connecting yarn is transmitted to the films 216 and 216 and the plate-shaped expanded bodies 221 and 222 through a joint with the ground knitted fabric, a sensing portion 230a of the vibration sensor 230 is preferably fixed to the surface of the three-dimensional solid knitted fabric 210 (the surface of the ground knitted fabric). As the vibration sensor 230, a microphone sensor or particularly a capacitive microphone sensor is preferably used. In this embodiment, since a sealing property of a site where the microphone sensor is disposed (that is, the arrangement through hole 215a in which the three-dimensional solid knitted fabric 210 is disposed) does not have to be considered, lead wires of the microphone sensor can be wired easily. A vibration of a body surface generated by a biological signal via a muscle of a person is transmitted not only to the three-dimensional solid knitted fabric 210 but also to the plate-shaped expanded bodies 221, 222 and the film 216, so that it is amplified due to overlapping of vibrations (string vibration and membrane oscillation (lateral wave)) of these members while attenuation is prevented. Therefore, the vibration sensor 230 is not limited to fixation to the three-dimensional solid knitted fabric 210 and the sensing portion 230a thereof may be fixed to the plate-shaped expanded bodies 221, 222 and the film 216 configuring a vibration transmission route.

Figure 34A:
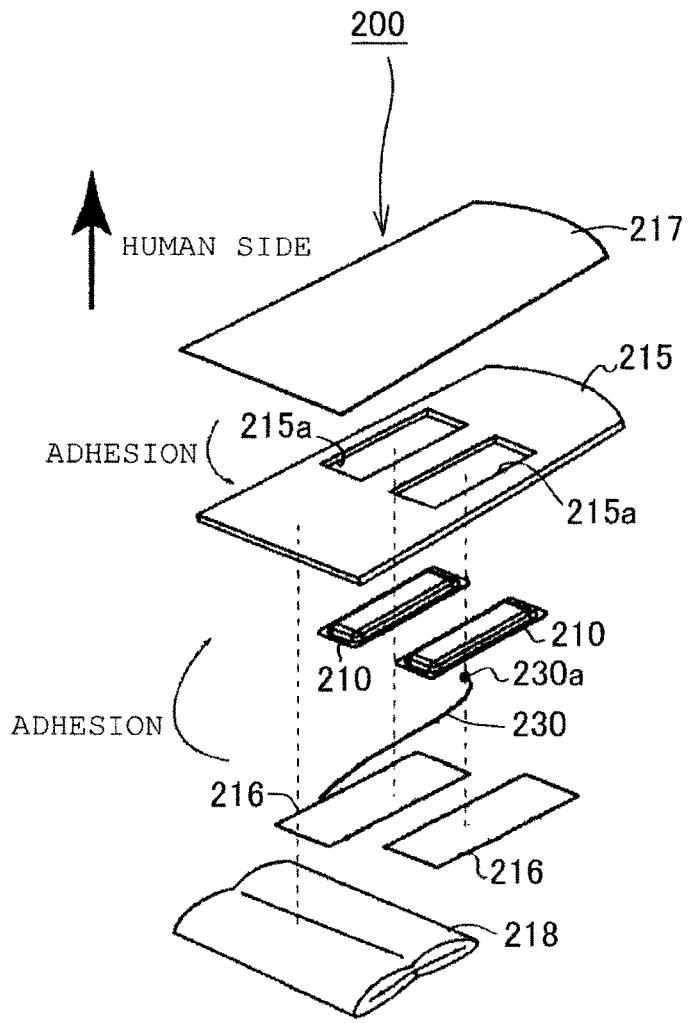
FIG. 34 is a view showing another example of the biological signal measuring means according to another embodiment.
Figure 34B:
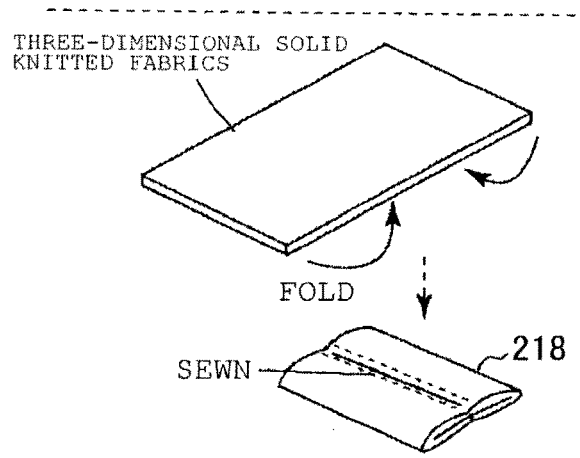

The biological signal measuring means 200 is not limited to that shown in FIG. 33 but a film 217 having the size that can cover both of the two three-dimensional solid knitted fabrics 210 and 210 may be used at least for one of the front side and the back side of the three-dimensional solid knitted fabrics 210 and 210 as illustrated in FIG. 34A, for example. Moreover, as shown in FIG. 34B, a lumber support 218 obtained such that the substantially rectangular three-dimensional solid knitted fabric is bent toward the center part from the both end edges and the overlapped center parts are sewn together may be arranged. The lumber support 218 is fixed to the three-dimensional solid knitted fabric support member 215 by using a planar faster or the like. By providing the lumber support 218 as above, contribution can be made to improve a stroke feeling in a narrow space.

Figure 35:
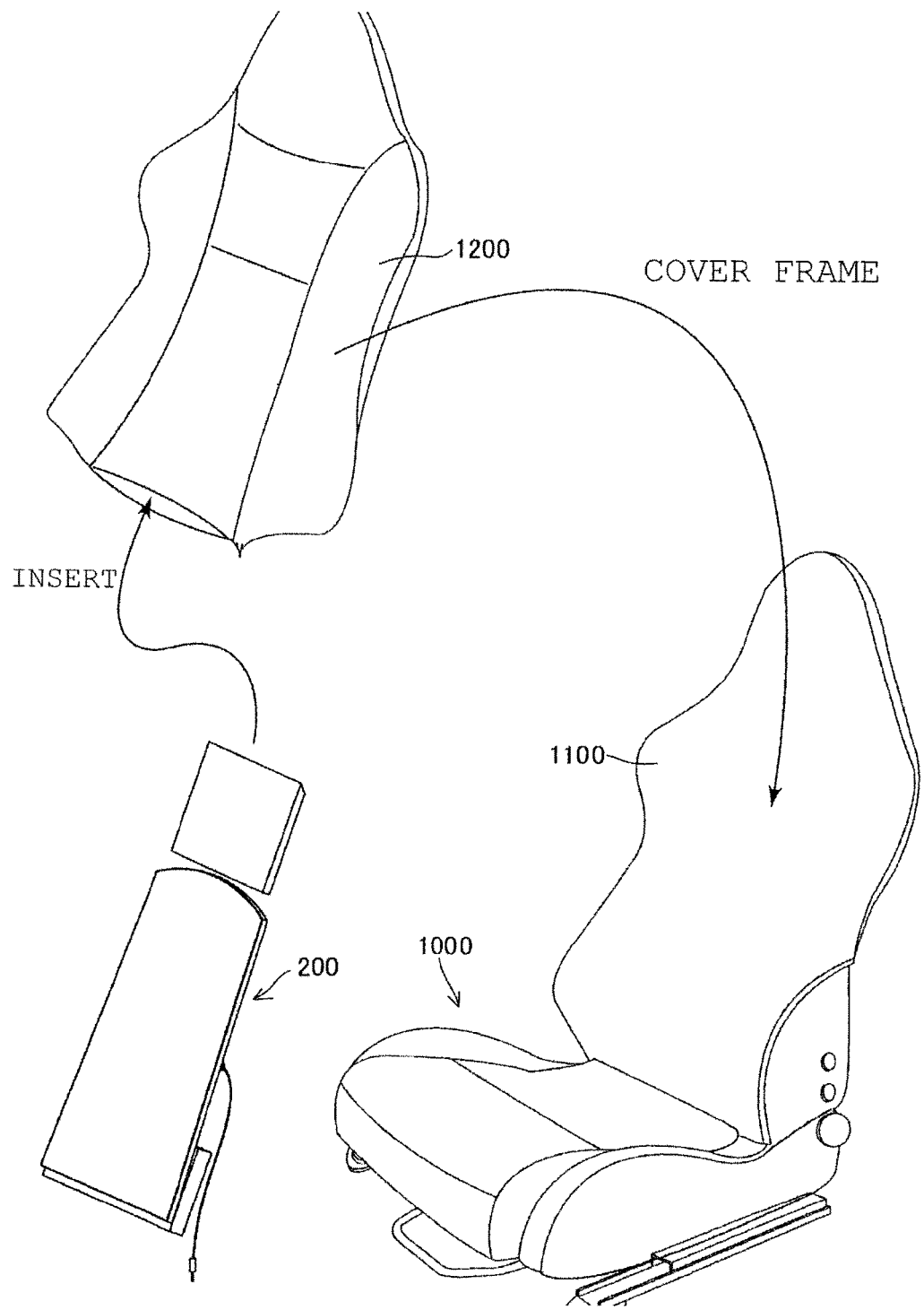
FIG. 35 is a view for explaining a process of incorporating the biological signal measuring means shown in FIG. 33 or FIG. 34 in a seat.

The above-described biological signal measuring means 200 is arranged inside a skin 1200 covering a seatback frame 1100 of an automobile seat 1000, for example, as shown in FIG. 35. In order to facilitate an arrangement work, it is preferable that the three-dimensional solid knitted fabric 210, the three-dimensional solid knitted fabric supporting member 215, the film 216, the plate-shaped expanded bodies 221, 222, the vibration sensor 230 and the like configuring the biological signal measuring means 200 are unitized in advance.

According to the above-described biological signal measuring means 200, membrane oscillation (lateral wave) occurs in the plate-shaped expanded bodies 221, 222 and the film 216 having the load-deflection characteristic similar to the load-deflection characteristic of a muscle and a string vibration occurs in the three-dimensional solid knitted fabric 210 having the load-deflection characteristic similar to the load-deflection characteristic of a muscle of a person by a biological signal. Then, the string vibration of the three-dimensional knitted fabric 210 affects the membrane oscillation (lateral wave) of the film 216 and the like again, and the vibration and oscillation serve in a superimposed state. As a result, vibration inputted from the body surface with occurrence of a biological signal is directly detected by the vibration sensor 230 as a solid vibration amplified by superimposition of the string vibration and the membrane oscillation (lateral wave) without attenuation.

In the case of the biological signal measuring means 1 which detects air pressure fluctuation within the air pack 10, shown in FIG. 1 and the like, since a volume and pressure are inversely proportional to each other, it is difficult to detect pressure fluctuation unless the volume of a sealing bag is made small. On the other hand, according to the biological signal measuring means 200 shown in FIGS. 33 to 35, since an amplified solid vibration transmitted to the mechanical amplifying device (the three-dimensional solid knitted fabric 210, the plate-shaped expanded bodies 221, 222, the film 216 or the film 217) is detected, as described above, instead of the air pressure fluctuation, the volume (cubic volume) is hardly limited from the viewpoint of detection sensitivity, so that a vibration with small amplitude as a cardiac oscillation wave can be detected with a high sensitivity. Therefore, the biological signal measuring means 200 can accommodate persons having various physical builds. Accordingly, the biological signal measuring means 200 shown in FIG. 33 to 35 can detect a biological signal with a high sensitivity even under such an environment where the means is utilized by persons having various physical builds and various external vibrations are inputted like an vehicle seat.

INDUSTRIAL APPLICABILITY

The present invention can be applied to estimation of a state of a person by arranging a biological signal measuring means on bedding such as a bed, capturing oscillation of an aorta on the back part, and analyzing the result by the above-described biological body state estimation device. As a result, a health state of a lying person (particularly, patients and those requiring care) can be easily grasped from a screen displayed on a monitor of the display means. Similarly, the present invention can be also applied to state estimation by arranging the biological signal measuring means on chairs disposed at home, office chairs and the like. As a result, heath states in a daily life can be easily grasped.

REFERENCE SIGNS LIST

1: biological signal measuring means
10: air pack
15: receiving body
100: air-pack unit
20: elastic member made of expanded resin beads
40, 45: three-dimensional solid knitted fabric
500: seat
510: seatback section
511: skin member
512: cushion supporting member
520: seat cushion section
60: biological body state estimation device
61: homeostatic function level computing means
611: frequency computing means (frequency computing step)
612: frequency slope time-series analyzing and computing means (frequency slope time-series analyzing and computing step)
613: frequency fluctuation time-series analyzing and computing means (frequency fluctuation time-series analyzing and computing step)
614: differentiating means (differentiating step)
615: integrating means (integrating step)
616: rectangular wave calculating means (rectangular wave calculating step)
617: describing function calculating means (describing function calculating step)
618: absolute value processing means (absolute value processing step)
619: homeostatic function stage calculating means (homeostatic function stage calculating step)
62: output means
63: determining means
65: display means

The invention claimed is:

1. A biological body state estimation device for estimating a state of fatigue of a person using a biological signal obtained from an upper body of the person, comprising:
an air pack configured to be brought into contact with a back part of the person and whose pressure has a pressure fluctuation that fluctuates with fluctuation in the aorta caused by movement of the heart, the air pack being further configured to output the pressure fluctuation as the biological signal; and
circuitry in electronic communication with the air pack and configured to
receive the biological signal from the air pack;
analyze the biological signal, and acquire and sort a homeostatic function level of the person at a predetermined point of time into a plurality of stages;
plot the homeostatic function level in a time series by taking each stage of the homeostatic function level on a vertical axis and time on a lateral axis and display a fluctuation degree of the homeostatic function level on a display circuit as a graph; and
determine the state of fatigue from the homeostatic function level;
wherein the circuitry is configured to analyze the biological signal and acquire and sort the homeostatic function by:

acquiring a frequency of the biological signal;

conducting a movement calculation to acquire a slope of the frequency for each predetermined time window set with a predetermined overlapped time from the frequency of the biological signal and acquiring a time-series waveform of the slope of the frequency obtained for each time window;

differentiating the time-series waveform of the slope of the frequency;

integrating the time-series waveform of the slope of the frequency;

acquiring a rectangular wave from an increase/decrease of the time-series waveform of the slope of the frequency;

acquiring a describing function and a describing function amplitude value between the time-series waveform of the slope of the frequency in an arbitrarily set first time zone and the time-series waveform of the slope of the frequency in a second time zone after the first time zone;

applying absolute value processing to the time-series waveform of the respective slopes of the frequency by using a time-series waveform of the frequency of the biological signal using a maximum value of the time-series waveform of the biological signal and a time-series waveform of the frequency of the biological signal using a zero-crossing point where the sign of the time-series waveform of the biological signal is switched; and acquiring the stage of the homeostatic function level by determining whether at least two indices indicate a characteristic change, wherein the at least two indices have the characteristic change according to said each stage of the homeostatic function level and are chosen independently for said each stage of the homeostatic function level, the at least two indices comprising at least two of the slope of the frequency, the differential value, the integral value, the sign of the rectangular wave, the describing function amplitude value, and two absolute values of the time-series waveform of the slope of the frequency.

2. The biological body state estimation device according to claim 1, wherein
the circuitry is configured to acquire and sort the homeostatic function level into a range of 3 to 10 stages from a highly active state to a functional decline state, and to sort and display the level in a range of 3 to 10 stages on the vertical axis with the highly active state as the highest part and the functional decline state as the lowest part.

3. The biological body state estimation device according to claim 2, wherein the circuitry is configured to
acquire and sort the homeostatic function level into five stages from the highly active state to the functional decline state; and
sort and display the level into five stages on the vertical axis with the highly active state as the highest part and the functional decline state as the lowest part.

4. The biological body state estimation device according to claim 1, wherein the circuitry is further configured to
determine a change in the state of a person from a graph displayed on the display circuit.

5. The biological body state estimation device according to claim 4, wherein
the circuitry is configured to determine an abnormal state if a rapid decline over two stages or more of the homeostatic function level occurs a predetermined number of times or more on the graph displayed on the display circuit.

6. The biological body state estimation device according to claim 1, wherein the circuitry is further configured to
filter the biological signal in a predetermined frequency band before being processed to acquire the homeostatic function level, wherein
the circuitry is configured to set a frequency band for filtering by acquiring a mean frequency of the biological signal under a static environment and using the mean frequency as a reference value.

7. The biological body state estimation system according to claim 1, wherein
the air pack is equipped to a seatback section of a vehicle seat.

8. A non-transitory computer-readable medium storing computer-executable instructions that, when executed on a computing device, cause the computing device to perform a method for estimating a state of fatigue of a person by using a biological signal obtained from the upper body of the person, the method comprising:

a receiving step of receiving, as the biological signal, a signal that fluctuates with fluctuation in the aorta caused by movement of the heart;

a homeostatic function level computing step that analyzes the biological signal, and acquires and sorts a homeostatic function level of the person at a predetermined point of time into a plurality of stages;

an output step that plots the homeostatic function level acquired by the homeostatic function level computing step in a time series with each stage of the homeostatic function level on a vertical axis and time on a lateral axis and displays it by a display circuit as a graph; and a fatigue-determining step that determines the state of fatigue from the homeostatic function level;

wherein the homeostatic function level computing step includes:

a frequency computing step that acquires a frequency of the biological signal;

a frequency slope time-series analyzing and computing step that conducts a movement calculation to acquire a slope of the frequency for each predetermined time window set with a predetermined overlapped time from the frequency of the biological signal obtained by the frequency computing step and acquires a time-series waveform of the slope of the frequency obtained for each time window;

a differentiating step that differentiates the time-series waveform of the slope of the frequency acquired by the frequency slope time-series analyzing and computing step;

an integrating step that integrates the time-series waveform of the slope of the frequency acquired by the frequency slope time-series analyzing and computing step;

a rectangular wave calculating step that acquires a rectangular wave from an increase/decrease of the time-series waveform of the slope of the frequency acquired by the frequency slope time-series analyzing and computing step;

a describing function calculating step that acquires a describing function and a describing function amplitude value between the time-series waveform of the slope of the frequency in an arbitrarily set first time zone and the time-series waveform of the slope of the frequency in a second time zone after the first time zone;

an absolute value processing step that applies absolute value processing to the time-series waveform of the respective slopes of the frequency acquired by the frequency slope time-series analyzing and computing step by using a time-series waveform of the frequency of the biological signal using a maximum value of the time-series waveform of the biological signal obtained by the frequency computing step and a time-series waveform of the frequency of the biological signal using a zero-crossing point where the sign of the time-series waveform of the biological signal is switched; and a homeostatic function stage calculating step that acquires the stage of the homeostatic function level by determining whether at least two indices indicate a characteristic change, wherein the at least two indices have the characteristic change according to said each stage of the homeostatic function level and are chosen independently for said each stage of the homeostatic function level, the at least two indices comprising at least two of the slope of the frequency acquired by the frequency slope time-series analyzing and computing step, the differential value acquired by the differentiating step, the integral value acquired by the integrating step, the sign of the rectangular wave acquired by the rectangular wave calculating step, the describing function amplitude value acquired by the describing function calculating step, and two absolute values of the time-series waveform of the slope of the frequency acquired by the absolute value processing step.

9. The medium according to claim 8, wherein the graph displayed by the display circuit by the output step is a line graph.

10. The medium according to claim 8, wherein the homeostatic function level computing step acquires and sorts the homeostatic function level into five stages from the highly active state to the functional decline state; and the output step sorts and displays the homeostatic function level in five stages with the highly active state as the highest part and the functional decline state as the lowest part on the vertical axis.

11. The medium according to claim 8, wherein the method further comprises:

a determining step that determines a change in the state of a person from a graph displayed on the display means by the output step.

12. The medium according to claim 11, wherein the determining step has an abnormal state determining step that determines an abnormal state if a decline over two stages or more of the homeostatic function level occurs a predetermined number of times or more on the graph displayed on the display circuit by the output step.

* * * * *